United States Patent
Wiener et al.

(10) Patent No.: US 11,051,873 B2
(45) Date of Patent: Jul. 6, 2021

(54) SURGICAL SYSTEM WITH USER ADAPTABLE TECHNIQUES EMPLOYING MULTIPLE ENERGY MODALITIES BASED ON TISSUE PARAMETERS

(71) Applicant: Ethicon Endo-Surgery, LLC, Guaynabo, PR (US)

(72) Inventors: Eitan T. Wiener, Cincinnati, OH (US); Benjamin J. Danziger, Cincinnati, OH (US); David C. Yates, West Chester, OH (US); Kevin L. Houser, Springboro, OH (US); Ryan M. Asher, Cincinnati, OH (US); Frederick E. Shelton, IV, Hillsboro, OH (US); Jeffrey D. Messerly, Cincinnati, OH (US); Geoffrey S. Strobl, Williamsburg, OH (US); Kristen G. Denzinger, Cincinnati, OH (US)

(73) Assignee: Cilag GmbH International, Zug (CH)

(*) Notice: Subject to any disclaimer, the term of this patent is extended or adjusted under 35 U.S.C. 154(b) by 1034 days.

(21) Appl. No.: 15/177,449

(22) Filed: Jun. 9, 2016

(65) Prior Publication Data

US 2017/0000553 A1  Jan. 5, 2017

Related U.S. Application Data

(60) Provisional application No. 62/186,984, filed on Jun. 30, 2015, provisional application No. 62/235,260, (Continued)

(51) Int. Cl.
*A61B 18/14* (2006.01)
*A61B 18/12* (2006.01)
(Continued)

(52) U.S. Cl.
CPC ...... *A61B 18/1445* (2013.01); *A61B 18/1233* (2013.01); *A61B 2017/00017* (2013.01);
(Continued)

(58) Field of Classification Search
CPC ............ A61B 18/1445; A61B 18/1233; A61B 18/1442; A61B 18/1452;
(Continued)

(56) References Cited

U.S. PATENT DOCUMENTS

| 969,528 A | 9/1910 | Disbrow |
|---|---|---|
| 1,570,025 A | 1/1926 | Young |

(Continued)

FOREIGN PATENT DOCUMENTS

| CA | 2535467 A1 | 4/1993 |
|---|---|---|
| CN | 2460047 Y | 11/2001 |

(Continued)

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

(Continued)

*Primary Examiner* — Linda C Dvorak
*Assistant Examiner* — Christine A Dedoulis

(57) ABSTRACT

Various forms are directed to systems and methods for dissection and coagulation of tissue. A method for detecting a short circuit in a surgical system configured to apply radio frequency energy and ultrasonic energy to a target surgical site that includes delivering radio frequency (RF) energy to an electrode of a surgical instrument, transitioning from delivering the RF energy to delivering ultrasonic energy to an ultrasonic blade of the surgical instrument, delivering an exploratory ultrasonic pulse to the ultrasonic blade, measuring an ultrasonic property of tissue engaged by the surgical (Continued)

instrument, wherein the ultrasonic property is associated with the exploratory ultrasonic pulse, determining whether the measured ultrasonic property is consistent with a behavior of low impedance tissue, and delivering ultrasonic energy to the ultrasonic blade to cut the tissue upon determining that the measured ultrasonic property is consistent with ultrasonic energy being applied to low impedance tissue.

12 Claims, 51 Drawing Sheets

Related U.S. Application Data filed on Sep. 30, 2015, provisional application No. 62/235,368, filed on Sep. 30, 2015, provisional application No. 62/235,466, filed on Sep. 30, 2015, provisional application No. 62/279,635, filed on Jan. 15, 2016, provisional application No. 62/330,669, filed on May 2, 2016.

(51) Int. Cl.
 *A61B 17/32* (2006.01)
 *A61B 18/00* (2006.01)
 *A61B 17/00* (2006.01)

(52) U.S. Cl.
 CPC .......... *A61B 2017/00026* (2013.01); *A61B 2017/320094* (2017.08); *A61B 2017/320095* (2017.08); *A61B 2018/00589* (2013.01); *A61B 2018/00601* (2013.01); *A61B 2018/00607* (2013.01); *A61B 2018/00642* (2013.01); *A61B 2018/00708* (2013.01); *A61B 2018/00875* (2013.01); *A61B 2018/00886* (2013.01); *A61B 2018/00994* (2013.01); *A61B 2018/1452* (2013.01)

(58) Field of Classification Search
 CPC .... A61B 17/320068; A61B 17/320092; A61B 2018/00589; A61B 2018/00601; A61B 2018/00607; A61B 2018/00642; A61B 2018/00708; A61B 2018/00875; A61B 2018/00886; A61B 2018/00994; A61B 2017/320094; A61B 2017/320095; A61B 2017/00017–0003; A61B 2017/00026; A61B 2017/00106; A61B 2017/0011; A61B 2017/00132; A61B 2017/00137; A61B 2017/00154; A61B 8/4272–429
 See application file for complete search history.

(56) References Cited

U.S. PATENT DOCUMENTS

| | | | |
|---|---|---|---|
| 1,813,902 | A | 7/1931 | Bovie |
| 2,188,497 | A | 1/1940 | Calva |
| 2,366,274 | A | 1/1945 | Luth et al. |
| 2,425,245 | A | 8/1947 | Johnson |
| 2,442,966 | A | 6/1948 | Wallace |
| 2,458,152 | A | 1/1949 | Eakins |
| 2,510,693 | A | 6/1950 | Green |
| 2,597,564 | A | 5/1952 | Bugg |
| 2,704,333 | A | 3/1955 | Calosi et al. |
| 2,736,960 | A | 3/1956 | Armstrong |
| 2,748,967 | A | 6/1956 | Roach |
| 2,845,072 | A | 7/1958 | Shafer |
| 2,849,788 | A | 9/1958 | Creek |
| 2,867,039 | A | 1/1959 | Zach |
| 2,874,470 | A | 2/1959 | Richards |
| 2,990,616 | A | 7/1961 | Balamuth et al. |
| RE25,033 | E | 8/1961 | Balamuth et al. |
| 3,015,961 | A | 1/1962 | Roney |
| 3,033,407 | A | 5/1962 | Alfons |
| 3,053,124 | A | 9/1962 | Balamuth et al. |
| 3,082,805 | A | 3/1963 | Royce |
| 3,166,971 | A | 1/1965 | Stoecker |
| 3,322,403 | A | 5/1967 | Murphy |
| 3,432,691 | A | 3/1969 | Shoh |
| 3,433,226 | A | 3/1969 | Boyd |
| 3,489,930 | A | 1/1970 | Shoh |
| 3,513,848 | A | 5/1970 | Winston et al. |
| 3,514,856 | A | 6/1970 | Camp et al. |
| 3,525,912 | A | 8/1970 | Wallin |
| 3,526,219 | A | 9/1970 | Balamuth |
| 3,554,198 | A | 1/1971 | Tatoian et al. |
| 3,580,841 | A | 5/1971 | Cadotte et al. |
| 3,606,682 | A | 9/1971 | Camp et al. |
| 3,614,484 | A | 10/1971 | Shoh |
| 3,616,375 | A | 10/1971 | Inoue |
| 3,629,726 | A | 12/1971 | Popescu |
| 3,636,943 | A | 1/1972 | Balamuth |
| 3,668,486 | A | 6/1972 | Silver |
| 3,702,948 | A | 11/1972 | Balamuth |
| 3,703,651 | A | 11/1972 | Blowers |
| 3,776,238 | A | 12/1973 | Peyman et al. |
| 3,777,760 | A | 12/1973 | Essner |
| 3,805,787 | A | 4/1974 | Banko |
| 3,809,977 | A | 5/1974 | Balamuth et al. |
| 3,830,098 | A | 8/1974 | Antonevich |
| 3,854,737 | A | 12/1974 | Gilliam, Sr. |
| 3,862,630 | A | 1/1975 | Balamuth |
| 3,875,945 | A | 4/1975 | Friedman |
| 3,885,438 | A | 5/1975 | Harris, Sr. et al. |
| 3,900,823 | A | 8/1975 | Sokal et al. |
| 3,918,442 | A | 11/1975 | Nikolaev et al. |
| 3,924,335 | A | 12/1975 | Balamuth et al. |
| 3,946,738 | A | 3/1976 | Newton et al. |
| 3,955,859 | A | 5/1976 | Stella et al. |
| 3,956,826 | A | 5/1976 | Perdreaux, Jr. |
| 3,989,952 | A | 11/1976 | Hohmann |
| 4,005,714 | A | 2/1977 | Hiltebrandt |
| 4,012,647 | A | 3/1977 | Balamuth et al. |
| 4,034,762 | A | 7/1977 | Cosens et al. |
| 4,058,126 | A | 11/1977 | Leveen |
| 4,074,719 | A | 2/1978 | Semm |
| 4,156,187 | A | 5/1979 | Murry et al. |
| 4,167,944 | A | 9/1979 | Banko |
| 4,188,927 | A | 2/1980 | Harris |
| 4,200,106 | A | 4/1980 | Douvas et al. |
| 4,203,430 | A | 5/1980 | Takahashi |
| 4,203,444 | A | 5/1980 | Bonnell et al. |
| 4,220,154 | A | 9/1980 | Semm |
| 4,237,441 | A | 12/1980 | van Konynenburg et al. |
| 4,244,371 | A | 1/1981 | Farin |
| 4,281,785 | A | 8/1981 | Brooks |
| 4,300,083 | A | 11/1981 | Heiges |
| 4,302,728 | A | 11/1981 | Nakamura |
| 4,304,987 | A | 12/1981 | van Konynenburg |
| 4,306,570 | A | 12/1981 | Matthews |
| 4,314,559 | A | 2/1982 | Allen |
| 4,353,371 | A | 10/1982 | Cosman |
| 4,409,981 | A | 10/1983 | Lundberg |
| 4,445,063 | A | 4/1984 | Smith |
| 4,463,759 | A | 8/1984 | Garito et al. |
| 4,491,132 | A | 1/1985 | Aikins |
| 4,492,231 | A | 1/1985 | Auth |
| 4,494,759 | A | 1/1985 | Kieffer |
| 4,504,264 | A | 3/1985 | Kelman |
| 4,512,344 | A | 4/1985 | Barber |
| 4,526,571 | A | 7/1985 | Wuchinich |
| 4,535,773 | A | 8/1985 | Yoon |
| 4,541,638 | A | 9/1985 | Ogawa et al. |
| 4,545,374 | A | 10/1985 | Jacobson |
| 4,545,926 | A | 10/1985 | Fouts, Jr. et al. |
| 4,549,147 | A | 10/1985 | Kondo |
| 4,550,870 | A | 11/1985 | Krumme et al. |
| 4,553,544 | A | 11/1985 | Nomoto et al. |
| 4,562,838 | A | 1/1986 | Walker |
| 4,574,615 | A | 3/1986 | Bower et al. |

(56) References Cited

U.S. PATENT DOCUMENTS

| | | |
|---|---|---|
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |

(56) References Cited

U.S. PATENT DOCUMENTS

| | | |
|---|---|---|
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |

(56) References Cited

U.S. PATENT DOCUMENTS

| | | |
|---|---|---|
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H001904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |

(56) References Cited

U.S. PATENT DOCUMENTS

| | | |
|---|---|---|
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H002037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |

(56) References Cited

U.S. PATENT DOCUMENTS

| | | |
|---|---|---|
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,602,262 B2 | 8/2003 | Griego et al. |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,632,221 B1 | 10/2003 | Edwards et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |

(56) References Cited

U.S. PATENT DOCUMENTS

| | | |
|---|---|---|
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckai et al. |
| 7,357,287 B2 | 4/2008 | Shelton, IV et al. |

(56) References Cited

U.S. PATENT DOCUMENTS

| | | |
|---|---|---|
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |

(56) References Cited

U.S. PATENT DOCUMENTS

| | | |
|---|---|---|
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |

(56) References Cited

U.S. PATENT DOCUMENTS

| | | |
|---|---|---|
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |
| 8,357,149 B2 | 1/2013 | Govari et al. |
| 8,357,158 B2 | 1/2013 | McKenna et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |

(56) References Cited

U.S. PATENT DOCUMENTS

| | | |
|---|---|---|
| 8,435,257 B2 | 5/2013 | Smith et al. |
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Homer |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,521,331 B2 | 8/2013 | Itkowitz |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Homer et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |

(56) References Cited

U.S. PATENT DOCUMENTS

| | | | |
|---|---|---|---|
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,060,778 B2 | 6/2015 | Condie et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,538 B2 | 7/2015 | Suzuki et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |

(56) References Cited

U.S. PATENT DOCUMENTS

| | | |
|---|---|---|
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,718 B2 | 12/2015 | Marczyk et al. |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,364,171 B2 | 6/2016 | Harris et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,393,070 B2 | 7/2016 | Gelfand et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,474,568 B2 | 10/2016 | Akagane |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,572,592 B2 | 2/2017 | Price et al. |
| 9,574,644 B2 | 2/2017 | Parihar |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,636,135 B2 | 5/2017 | Stulen |
| 9,636,165 B2 | 5/2017 | Larson et al. |

(56) References Cited

U.S. PATENT DOCUMENTS

| | | |
|---|---|---|
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,687,290 B2 | 6/2017 | Keller |
| 9,690,362 B2 | 6/2017 | Leimbach et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,730,695 B2 | 8/2017 | Leimbach et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,802,033 B2 | 10/2017 | Hibner et al. |
| 9,808,246 B2 | 11/2017 | Shelton, IV et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,839,443 B2 | 12/2017 | Brockman et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,878,184 B2 | 1/2018 | Beaupre |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,656 B2 | 3/2018 | Stulen |
| 9,913,680 B2 | 3/2018 | Voegele et al. |
| 9,918,730 B2 | 3/2018 | Trees et al. |
| 9,925,003 B2 | 3/2018 | Parihar et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,974,539 B2 | 5/2018 | Yates et al. |
| 9,987,033 B2 | 6/2018 | Neurohr et al. |
| 10,004,526 B2 | 6/2018 | Dycus et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,070,916 B2 | 9/2018 | Artale |
| 10,080,609 B2 | 9/2018 | Hancock et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,699 B2 | 10/2018 | Boudreaux |
| 10,111,703 B2 | 10/2018 | Cosman, Jr. et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,410 B2 | 11/2018 | Strobl et al. |
| 10,130,412 B2 | 11/2018 | Wham |
| 10,154,848 B2 | 12/2018 | Chernov et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,179,022 B2 | 1/2019 | Yates et al. |
| 10,188,455 B2 | 1/2019 | Hancock et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,238,391 B2 | 3/2019 | Leimbach et al. |
| 10,245,095 B2 | 4/2019 | Boudreaux |
| 10,245,104 B2 | 4/2019 | McKenna et al. |
| 10,251,664 B2 | 4/2019 | Shelton, IV et al. |
| 10,263,171 B2 | 4/2019 | Wiener et al. |
| 10,265,117 B2 | 4/2019 | Wiener et al. |
| 10,265,118 B2 | 4/2019 | Gerhardt |
| 10,271,840 B2 | 4/2019 | Sapre |
| 10,278,721 B2 | 5/2019 | Dietz et al. |
| 10,285,724 B2 | 5/2019 | Faller et al. |
| 10,285,750 B2 | 5/2019 | Coulson et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,602 B2 | 7/2019 | Strobl et al. |
| 10,342,606 B2 | 7/2019 | Cosman et al. |
| 10,349,999 B2 | 7/2019 | Yates et al. |
| 10,357,303 B2 | 7/2019 | Conlon et al. |
| 10,363,084 B2 | 7/2019 | Friedrichs |

(56) References Cited

U.S. PATENT DOCUMENTS

| | | |
|---|---|---|
| 10,376,305 B2 | 8/2019 | Yates et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,420,579 B2 | 9/2019 | Wiener et al. |
| 10,420,607 B2 | 9/2019 | Woloszko et al. |
| 10,426,507 B2 | 10/2019 | Wiener et al. |
| 10,426,978 B2 | 10/2019 | Akagane |
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,448,986 B2 | 10/2019 | Zikorus et al. |
| 10,456,193 B2 | 10/2019 | Yates et al. |
| 10,463,421 B2 | 11/2019 | Boudreaux et al. |
| 10,463,887 B2 | 11/2019 | Witt et al. |
| 10,485,607 B2 | 11/2019 | Strobl et al. |
| 10,492,849 B2 | 12/2019 | Juergens et al. |
| 10,512,795 B2 | 12/2019 | Voegele et al. |
| 10,517,627 B2 | 12/2019 | Timm et al. |
| 10,561,560 B2 | 2/2020 | Boutoussov et al. |
| 10,617,420 B2 | 4/2020 | Shelton, IV et al. |
| RE47,996 E | 5/2020 | Turner et al. |
| 10,677,764 B2 | 6/2020 | Ross et al. |
| 10,874,465 B2 | 12/2020 | Weir et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0177862 A1 | 11/2002 | Aranyi et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0109778 A1 | 6/2003 | Rashidi |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0193153 A1 | 9/2004 | Sartor et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1* | 3/2005 | Takahashi ...... A61B 17/320092 600/459 |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iljima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |

(56) References Cited

U.S. PATENT DOCUMENTS

| | | |
|---|---|---|
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0065565 A1 | 3/2009 | Cao |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0090763 A1 | 4/2009 | Zemlok et al. |
| 2009/0118751 A1 | 5/2009 | Wiener et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0198272 A1 | 8/2009 | Kerver et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042093 A9 | 2/2010 | Wham et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |

(56) References Cited

U.S. PATENT DOCUMENTS

| | | |
|---|---|---|
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228250 A1 | 9/2010 | Brogna |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0331742 A1 | 12/2010 | Masuda |
| 2011/0004233 A1 | 1/2011 | Muir et al. |
| 2011/0015650 A1 | 1/2011 | Choi et al. |
| 2011/0028964 A1 | 2/2011 | Edwards |
| 2011/0071523 A1 | 3/2011 | Dickhans |
| 2011/0106141 A1 | 5/2011 | Nakamura |
| 2011/0112400 A1 | 5/2011 | Emery et al. |
| 2011/0125149 A1 | 5/2011 | El-Galley et al. |
| 2011/0125151 A1 | 5/2011 | Strauss et al. |
| 2011/0160725 A1 | 6/2011 | Kabaya et al. |
| 2011/0238010 A1 | 9/2011 | Kirschenman et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136279 A1 | 5/2012 | Tanaka et al. |
| 2012/0136354 A1* | 5/2012 | Rupp ............... A61B 18/1206 606/51 |
| 2012/0136386 A1 | 5/2012 | Kishida et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0211542 A1 | 8/2012 | Racenet |
| 2012/0253328 A1 | 10/2012 | Cunningham et al. |
| 2012/0265241 A1 | 10/2012 | Hart et al. |
| 2012/0296325 A1 | 11/2012 | Takashino |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0085510 A1 | 4/2013 | Stefanchik et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0277410 A1 | 10/2013 | Fernandez et al. |
| 2013/0282003 A1* | 10/2013 | Messerly ............. A61B 18/1206 606/37 |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0121569 A1 | 5/2014 | Schafer et al. |
| 2014/0135804 A1 | 5/2014 | Weisenburgh, II et al. |
| 2014/0180274 A1 | 6/2014 | Kabaya et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0246475 A1 | 9/2014 | Hall et al. |
| 2014/0263541 A1 | 9/2014 | Leimbach et al. |
| 2014/0263552 A1 | 9/2014 | Hall et al. |
| 2014/0276754 A1 | 9/2014 | Gilbert et al. |
| 2014/0276797 A1 | 9/2014 | Batchelor et al. |
| 2014/0276806 A1 | 9/2014 | Heim |
| 2015/0032150 A1 | 1/2015 | Ishida et al. |
| 2015/0080876 A1 | 3/2015 | Worrell et al. |
| 2015/0080887 A1 | 3/2015 | Sobajima et al. |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0238260 A1 | 8/2015 | Nau, Jr. |
| 2015/0257780 A1 | 9/2015 | Houser |
| 2015/0272659 A1 | 10/2015 | Boudreaux et al. |
| 2015/0282879 A1 | 10/2015 | Ruelas |
| 2015/0313667 A1 | 11/2015 | Allen, IV |
| 2015/0320481 A1 | 11/2015 | Cosman, Jr. et al. |
| 2016/0045248 A1 | 2/2016 | Unger et al. |
| 2016/0051316 A1 | 2/2016 | Boudreaux |
| 2016/0074108 A1 | 3/2016 | Woodruff et al. |
| 2016/0157927 A1 | 6/2016 | Corbett et al. |
| 2016/0175029 A1 | 6/2016 | Witt et al. |
| 2016/0199125 A1 | 7/2016 | Jones |
| 2016/0206342 A1 | 7/2016 | Robertson et al. |
| 2016/0262786 A1 | 9/2016 | Madan et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0324537 A1 | 11/2016 | Green et al. |
| 2016/0346001 A1 | 12/2016 | Vakharia et al. |
| 2016/0367281 A1 | 12/2016 | Gee et al. |
| 2017/0000516 A1 | 1/2017 | Stulen et al. |
| 2017/0000541 A1 | 1/2017 | Yates et al. |
| 2017/0000542 A1 | 1/2017 | Yates et al. |
| 2017/0000554 A1 | 1/2017 | Yates et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0105757 A1 | 4/2017 | Weir et al. |
| 2017/0105782 A1 | 4/2017 | Scheib et al. |
| 2017/0105786 A1 | 4/2017 | Scheib et al. |
| 2017/0105791 A1 | 4/2017 | Yates et al. |
| 2017/0119426 A1 | 5/2017 | Akagane |
| 2017/0135751 A1 | 5/2017 | Rothweiler et al. |
| 2017/0164994 A1 | 6/2017 | Smith |
| 2017/0189095 A1 | 7/2017 | Danziger et al. |
| 2017/0189096 A1 | 7/2017 | Danziger et al. |
| 2017/0196586 A1 | 7/2017 | Witt et al. |
| 2017/0202571 A1 | 7/2017 | Shelton, IV et al. |
| 2017/0202572 A1 | 7/2017 | Shelton, IV et al. |

(56) References Cited

U.S. PATENT DOCUMENTS

| | | |
|---|---|---|
| 2017/0202591 A1 | 7/2017 | Shelton, IV et al. |
| 2017/0202592 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0238991 A1 | 8/2017 | Worrell et al. |
| 2017/0245875 A1 | 8/2017 | Timm et al. |
| 2017/0312014 A1 | 11/2017 | Strobl et al. |
| 2017/0312015 A1 | 11/2017 | Worrell et al. |
| 2017/0312017 A1 | 11/2017 | Trees et al. |
| 2017/0312018 A1 | 11/2017 | Trees et al. |
| 2017/0312019 A1 | 11/2017 | Trees et al. |
| 2017/0325874 A1 | 11/2017 | Noack et al. |
| 2017/0348064 A1 | 12/2017 | Stewart et al. |
| 2017/0360468 A1 | 12/2017 | Eichmann et al. |
| 2018/0014872 A1 | 1/2018 | Dickerson |
| 2018/0028257 A1 | 2/2018 | Yates et al. |
| 2018/0042658 A1 | 2/2018 | Shelton, IV et al. |
| 2018/0064961 A1 | 3/2018 | Wiener et al. |
| 2018/0078277 A1 | 3/2018 | Illizaliturri-Sanchez et al. |
| 2018/0098785 A1 | 4/2018 | Price et al. |
| 2018/0098808 A1 | 4/2018 | Yates et al. |
| 2018/0146976 A1 | 5/2018 | Clauda et al. |
| 2018/0177545 A1 | 6/2018 | Boudreaux et al. |
| 2018/0235691 A1 | 8/2018 | Voegele et al. |
| 2018/0280083 A1 | 10/2018 | Parihar et al. |
| 2019/0021783 A1 | 1/2019 | Asher et al. |
| 2019/0105067 A1 | 4/2019 | Boudreaux et al. |
| 2019/0201048 A1 | 7/2019 | Stulen et al. |
| 2019/0209201 A1 | 7/2019 | Boudreaux et al. |
| 2019/0262030 A1 | 8/2019 | Faller et al. |
| 2019/0274700 A1 | 9/2019 | Robertson et al. |
| 2019/0282288 A1 | 9/2019 | Boudreaux |
| 2019/0282292 A1 | 9/2019 | Wiener et al. |
| 2020/0015883 A1 | 1/2020 | Batross et al. |
| 2020/0022724 A1 | 1/2020 | Worrell et al. |
| 2020/0030021 A1 | 1/2020 | Yates et al. |
| 2020/0054382 A1 | 2/2020 | Yates et al. |
| 2020/0078085 A1 | 3/2020 | Yates et al. |
| 2020/0078609 A1 | 3/2020 | Messerly et al. |
| 2020/0085465 A1 | 3/2020 | Timm et al. |
| 2020/0113624 A1 | 4/2020 | Worrell et al. |
| 2020/0138473 A1 | 5/2020 | Shelton, Iv et al. |
| 2020/0222135 A1 | 7/2020 | Stulen et al. |
| 2020/0229833 A1 | 7/2020 | Vakharia et al. |
| 2020/0229834 A1 | 7/2020 | Olson et al. |
| 2020/0237434 A1 | 7/2020 | Scheib et al. |
| 2020/0261141 A1 | 8/2020 | Wiener et al. |
| 2020/0268433 A1 | 8/2020 | Wiener et al. |

FOREIGN PATENT DOCUMENTS

| | | |
|---|---|---|
| CN | 1634601 A | 7/2005 |
| CN | 1775323 A | 5/2006 |
| CN | 1922563 A | 2/2007 |
| CN | 2868227 Y | 2/2007 |
| CN | 101474081 A | 7/2009 |
| CN | 101516285 A | 8/2009 |
| CN | 102100582 A | 6/2011 |
| CN | 102149312 A | 8/2011 |
| CN | 202027624 U | 11/2011 |
| CN | 103281982 A | 9/2013 |
| CN | 103379853 A | 10/2013 |
| DE | 3904558 A1 | 8/1990 |
| DE | 9210327 U1 | 11/1992 |
| DE | 4300307 A1 | 7/1994 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2668922 A1 | 12/2013 |
| EP | 2076195 B1 | 12/2015 |
| EP | 2510891 B1 | 6/2016 |
| GB | 2032221 A | 4/1980 |
| GB | 2317566 A | 4/1998 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H0541716 A | 2/1993 |
| JP | H0595955 A | 4/1993 |
| JP | H05115490 A | 5/1993 |
| JP | H0670938 A | 3/1994 |
| JP | H06104503 A | 4/1994 |
| JP | H0824266 A | 1/1996 |
| JP | H08229050 A | 9/1996 |
| JP | H08275951 A | 10/1996 |
| JP | H08299351 A | 11/1996 |
| JP | H08336545 A | 12/1996 |
| JP | H09130655 A | 5/1997 |
| JP | H09135553 A | 5/1997 |
| JP | H09140722 A | 6/1997 |
| JP | H105237 A | 1/1998 |
| JP | 10127654 A | 5/1998 |
| JP | H10295700 A | 11/1998 |
| JP | H11128238 A | 5/1999 |
| JP | 2000210299 A | 8/2000 |
| JP | 2000271145 A | 10/2000 |
| JP | 2000287987 A | 10/2000 |
| JP | 2001029353 A | 2/2001 |
| JP | 2002059380 A | 2/2002 |
| JP | 2002186901 A | 7/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2005003496 A | 1/2005 |

(56) References Cited

FOREIGN PATENT DOCUMENTS

| | | | |
|---|---|---|---|
| JP | 2005027026 A | 1/2005 |
| JP | 2005074088 A | 3/2005 |
| JP | 2005337119 A | 12/2005 |
| JP | 2006068396 A | 3/2006 |
| JP | 2006081664 A | 3/2006 |
| JP | 2006114072 A | 4/2006 |
| JP | 2006217716 A | 8/2006 |
| JP | 2006288431 A | 10/2006 |
| JP | 2007037568 A | 2/2007 |
| JP | 200801876 A | 1/2008 |
| JP | 200833644 A | 2/2008 |
| JP | 2008188160 A | 8/2008 |
| JP | D1339835 S | 8/2008 |
| JP | 2010009686 A | 1/2010 |
| JP | 2010121865 A | 6/2010 |
| JP | 2012071186 A | 4/2012 |
| JP | 2012235658 A | 11/2012 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9920213 A1 | 4/1999 |
| WO | WO-9923960 A1 | 5/1999 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0172251 A1 | 10/2001 |
| WO | WO-0195810 A2 | 12/2001 |
| WO | WO-03095028 A1 | 11/2003 |
| WO | WO-2004037095 A2 | 5/2004 |
| WO | WO-2004078051 A2 | 9/2004 |
| WO | WO-2004098426 A1 | 11/2004 |
| WO | WO-2007008710 A2 | 1/2007 |
| WO | WO-2008118709 A1 | 10/2008 |
| WO | WO-2008130793 A1 | 10/2008 |
| WO | WO-2010027109 A1 | 3/2010 |
| WO | WO-2010104755 A1 | 9/2010 |
| WO | WO-2011008672 A2 | 1/2011 |
| WO | WO-2011044343 A2 | 4/2011 |
| WO | WO-2011052939 A2 | 5/2011 |
| WO | WO-2011060031 A1 | 5/2011 |
| WO | WO-2012044606 A2 | 4/2012 |
| WO | WO-2012088535 A1 | 6/2012 |
| WO | WO-2012/150567 A1 | 11/2012 |

OTHER PUBLICATIONS

Hörmann et al., "Reversible and irreversible denaturation of collagen fibers." Biochemistry, 10, pp. 932-937 (1971).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Covidien Brochure, The LigaSure Precise™ Instrument, dated Mar. 2011 (2 pages).
AST Products, Inc., "Principles of Video Contact Angle Analysis," 20 pages, (2006).
Chen et al., "Heat-Induced Changes in the Mechanics of a Collagenous Tissue: Isothermal Free Shrinkage," Transactions of the ASME, vol. 119, pp. 372-378 (Nov. 1997).
Chen Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Heat-induced changes in the mechanics of a collagenous tissue: pseudoelastic behavior at 37° C.," Journal of Biomechanics, 31, pp. 211-216 (1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Leonard I. Malls, M.D., "The Value of Irrigation During Bipolar Coagulation," 1989.
Ethicon UK, "Generator G11, The Ethicon Endo-Surgery Generator", p. 1, (May 30, 2013).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Orr et al., "Overview of Bioheat Transfer," pp. 367-384 in Optical-Thermal Response of Laser-Irradiated Tissue, A. J. Welch and M. J. C. van Gernert, eds., Plenum, New York (1995).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in Physical Properties of Tissue (1990).
Campbell et al, "Thermal Imaging in Surgery," p. 19-3, in Medical Infrared Imaging, N. A. Diakides and J. D. Bronzino, Eds. (2008). http://www.dotmed.com/listing/electrosurical-unit/ethicon/ultracision-g110-/1466724.
4-Traders, "Johnson & Johnson (JNJ) : Ethicon Endo-Surgery Highlights Commitment to Nurse Education, Patient Safety and Key Product Innovations at the Association for Perioperative Registered Nurses (AORN) Conference", p. 1 of 3, (Jan. 15, 2013) (1 page).
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Covidien Brochure, [Value Analysis Brief], LigaSure Advance™ Pistol Grip, dated Rev. Apr. 2010 (7 pages).
Wright, et al., "Time-Temperature Equivalence of Heat-Induced Changes in Cells and Proteins," Feb. 1998. ASME Journal of Biomechanical Engineering, vol. 120, pp. 22-26.

(56) References Cited

OTHER PUBLICATIONS

Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Jang, J. et al. "Neuro-fuzzy and Soft Computing." Prentice Hall, 1997, pp. 13-89, 199-293, 335-393, 453-496, 535-549.
Sullivan, "Optimal Choice for Number of Strands in a Litz-Wire Transformer Winding," IEEE Transactions on Power Electronics, vol. 14, No. 2, Mar. 1999, pp. 283-291.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Wall et al., "Thermal modification of collagen," J Shoulder Elbow Surg, No. 8, pp. 339-344 (Jul./Aug. 1999).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalet.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Douglas, S.C. Introduction to Adaptive Filter. Digital Signal Processing Handbook. Ed. Vijay K. Madisetti and Douglas B. Williams. Boca Raton: CRC Press LLC, 1999.
Kurt Gieck & Reiner Gieck, *Engineering Formulas* § Z.7 (7th ed. 1997).
Glaser and Subak-Sharpe, Integrated Circuit Engineering, Addison-Wesley Publishing, Reading, MA (1979). (book—not attached).
Covidien 501(k) Summary Sonicision, dated Feb. 24, 2011 (7 pages).
http://www.megadyne.com/es_generator.php.
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
http://www.apicalinstr.com/generators.htm.
http://www.medicalexpo.com/medical-manufacturer/electrosurgical-generator-6951.html.
http://www.valleylab.com/product/es/generators/index.html.
Moraleda et al., A Temperature Sensor Based on a Polymer Optical Fiber Macro-Bend, Sensors 2013, 13, 13076-13089, doi: 10.3390/s131013076, ISSN 1424-8220.

* cited by examiner

SURGICAL SYSTEM WITH USER ADAPTABLE TECHNIQUES EMPLOYING MULTIPLE ENERGY MODALITIES BASED ON TISSUE PARAMETERS

PRIORITY

This application claims the benefit of U.S. Provisional Application Ser. No. 62/186,984 filed Jun. 30, 2015, U.S. Provisional Application Ser. No. 62/235,260, filed Sep. 30, 2015, U.S. Provisional Application Ser. No. 62/235,368, filed Sep. 30, 2015, U.S. Provisional Application Ser. No. 62/235,466, filed Sep. 30, 2015, U.S. Provisional Application Ser. No. 62/279,635, filed Jan. 15, 2016, and U.S. Provisional Application Ser. No. 62/330,669, filed May 2, 2016, the contents of which are incorporated herein by reference in their entirety.

TECHNICAL FIELD

The present disclosure generally relates to ultrasonic surgical systems and, more particularly, to ultrasonic and electrosurgical systems that allow surgeons to perform cutting and coagulation and adapt and customize techniques for performing such procedures and employing multiple energy modalities based on tissue parameters.

BACKGROUND

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically realized by an-end effector, or blade tip, at the distal end of the instrument, which transmits ultrasonic energy to tissue brought into contact with the end effector. Ultrasonic instruments of this nature can be configured for open surgical use, laparoscopic, or endoscopic surgical procedures including robotic-assisted procedures.

Some surgical instruments utilize ultrasonic energy for both precise cutting and controlled coagulation. Ultrasonic energy cuts and coagulates by vibrating a blade in contact with tissue. Vibrating at high frequencies (e.g., 55,500 times per second), the ultrasonic blade denatures protein in the tissue to form a sticky coagulum. Pressure exerted on tissue with the blade surface collapses blood vessels and allows the coagulum to form a hemostatic seal. The precision of cutting and coagulation is controlled by the surgeon's technique and adjusting the power level, blade edge, tissue traction, and blade pressure.

Electrosurgical devices for applying electrical energy to tissue in order to treat and/or destroy the tissue are also finding increasingly widespread applications in surgical procedures. An electrosurgical device typically includes a hand piece, an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example. The end effector of an electrosurgical device also may include a cutting member that is movable relative to the tissue and the electrodes to transect the tissue.

Electrical energy applied by an electrosurgical device can be transmitted to the instrument by a generator in communication with the hand piece. The electrical energy may be in the form of radio frequency ("RF") energy. RF energy is a form of electrical energy that may be in the frequency range of 200 kilohertz (kHz) to 1 megahertz (MHz). In application, an electrosurgical device can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

The RF energy may be in a frequency range described in EN 60601-2-2:2009+A11:2011, Definition 201.3.218—HIGH FREQUENCY. For example, the frequency in monopolar RF applications may be typically restricted to less than 5 MHz. However, in bipolar RF applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications. It is generally recognized that 10 mA is the lower threshold of thermal effects on tissue.

A challenge of using these medical devices is the inability to control and customize the power output depending on the type of tissue being treated by the devices. It would be desirable to provide a surgical instrument that overcomes some of the deficiencies of current instruments. The surgical system described herein overcomes those deficiencies.

SUMMARY

In one aspect, a method for detecting a short circuit in a surgical system configured to apply radio frequency energy and ultrasonic energy to a target surgical site is provided. The method comprises applying radio frequency (RF) energy with an end effector to the target surgical site; transitioning from applying the RF energy to applying ultrasonic energy with the end effector to the target surgical site; transmitting an exploratory ultrasonic pulse to the surgical site; measuring an ultrasonic property about the ultrasonic pulse upon transmission to the surgical site; determining whether the ultrasonic property is consistent with a behavior of low impedance tissue when ultrasonic energy is applied to the low impedance tissue; and continuing to apply ultrasonic energy to cut the low impedance tissue if it is determined that the ultrasonic property is consistent with ultrasonic energy being applied to low impedance tissue.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to affect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

Further, it is understood that any one or more of the following-described forms, expressions of forms, examples, can be combined with any one or more of the other following-described forms, expressions of forms, and examples.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the described forms are set forth with particularity in the appended claims. The described forms, however, both as to organization and methods of operation, may be best understood by reference to the following description, taken in conjunction with the accompanying drawings in which:

FIG. 24 illustrates a graph depicting one aspect of adjustment of threshold due to the measurement of a secondary tissue parameter such as continuity, temperature, pressure, and the like;

Figure 43A:
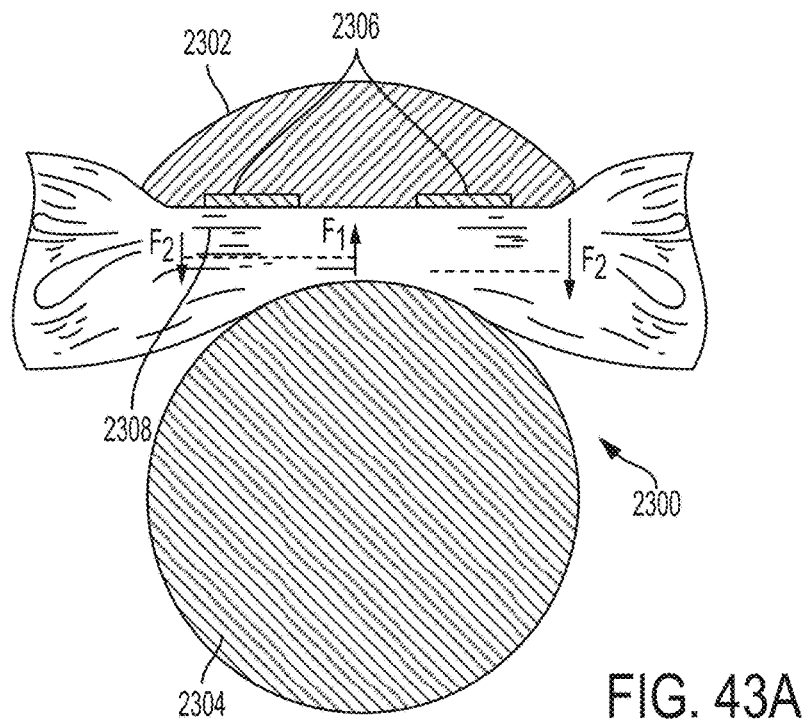
FIG. 43A is a graphical representation of one aspect of a medical device compressing tissue.
Figure 43B:
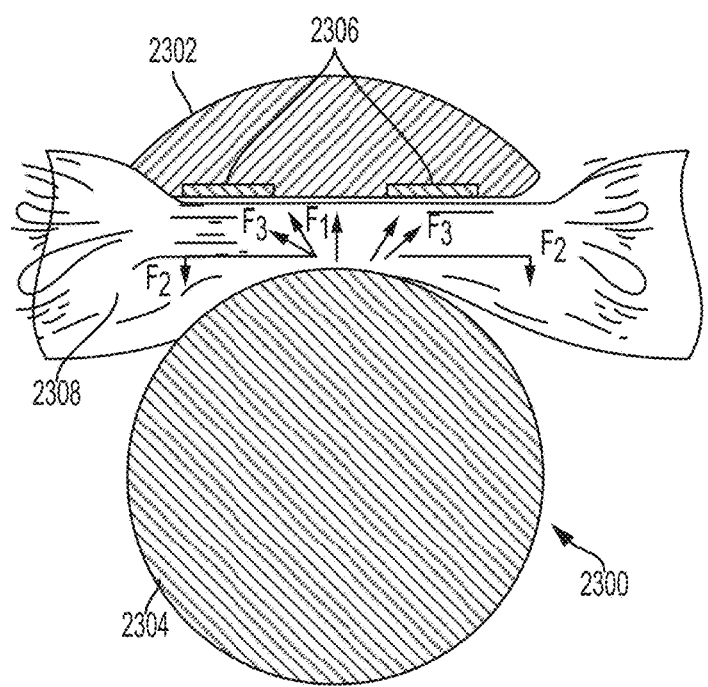
Figure 44:
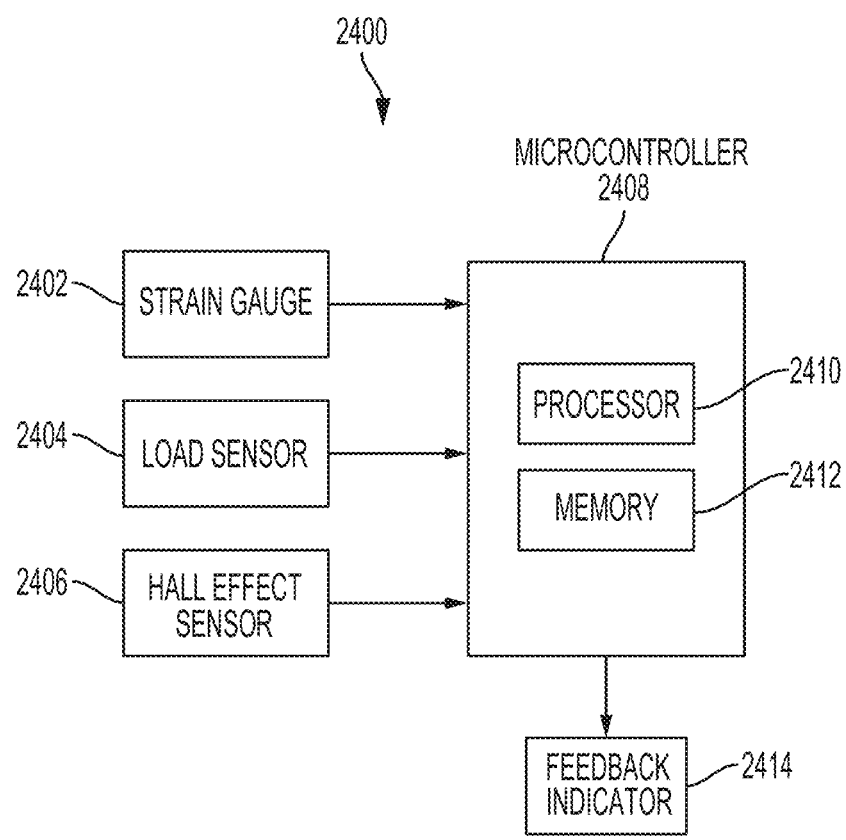
Figure 45:
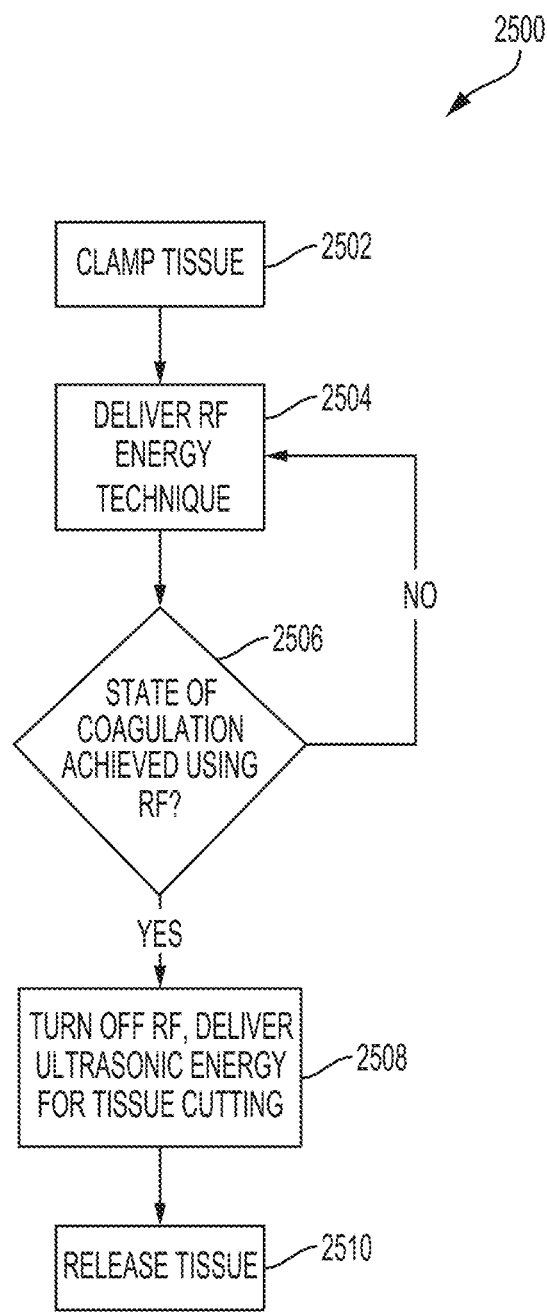
Figure 46:
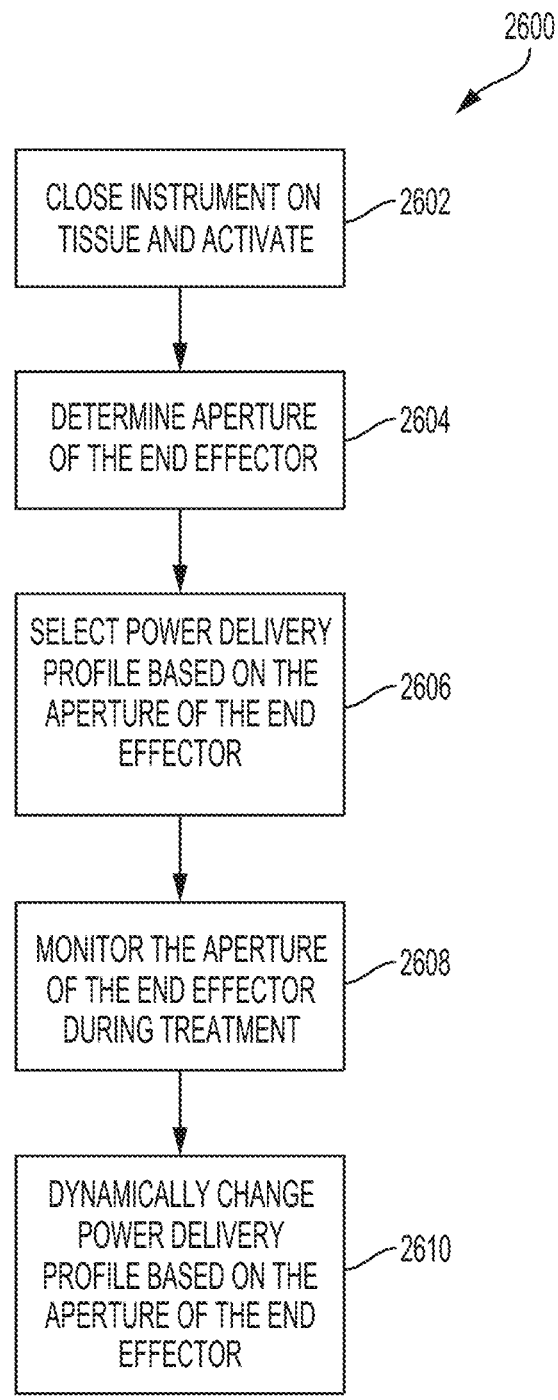
Figure 47:
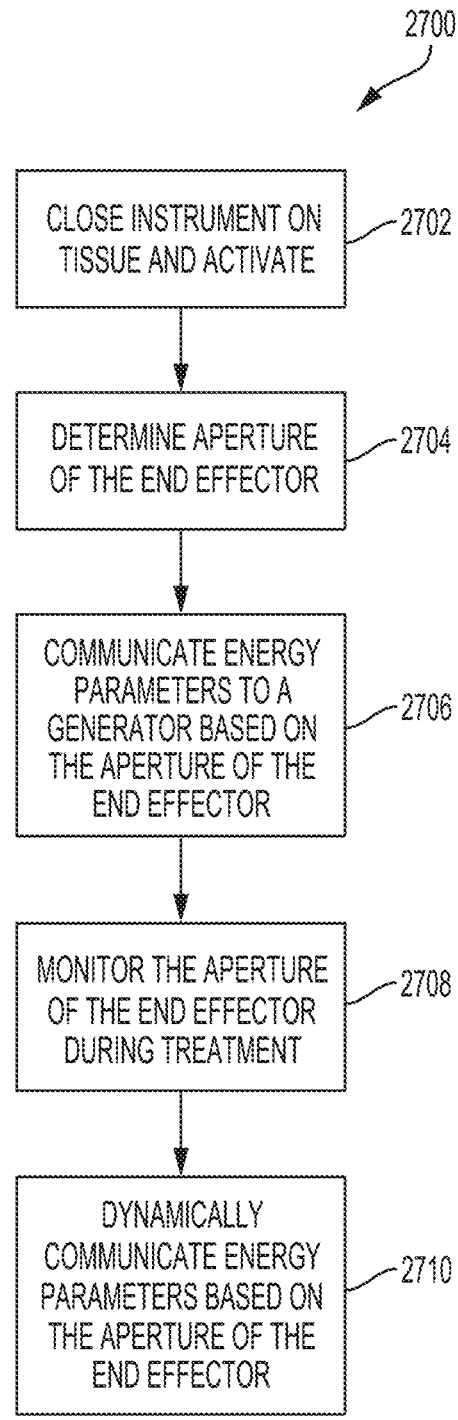
Figure 48:
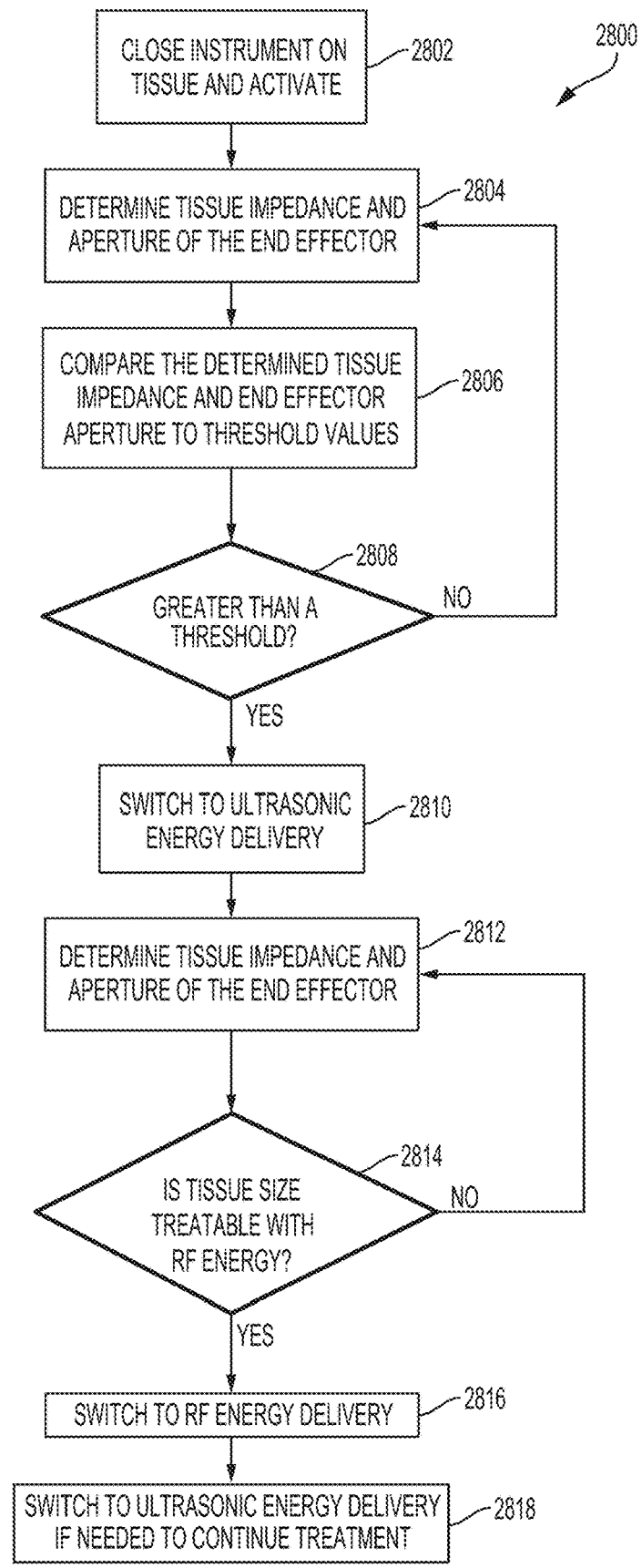
Figure 49:
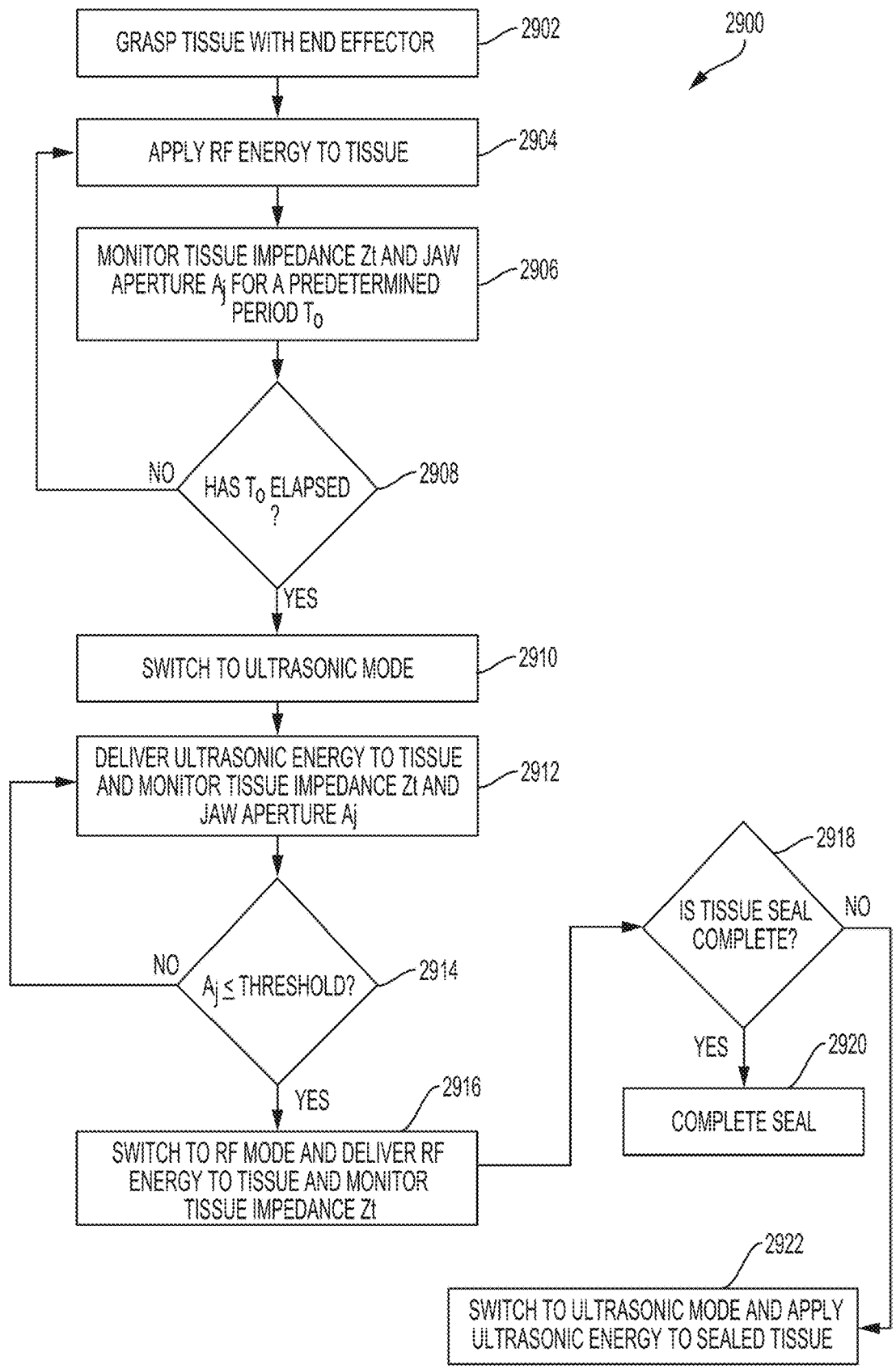
Figure 50:
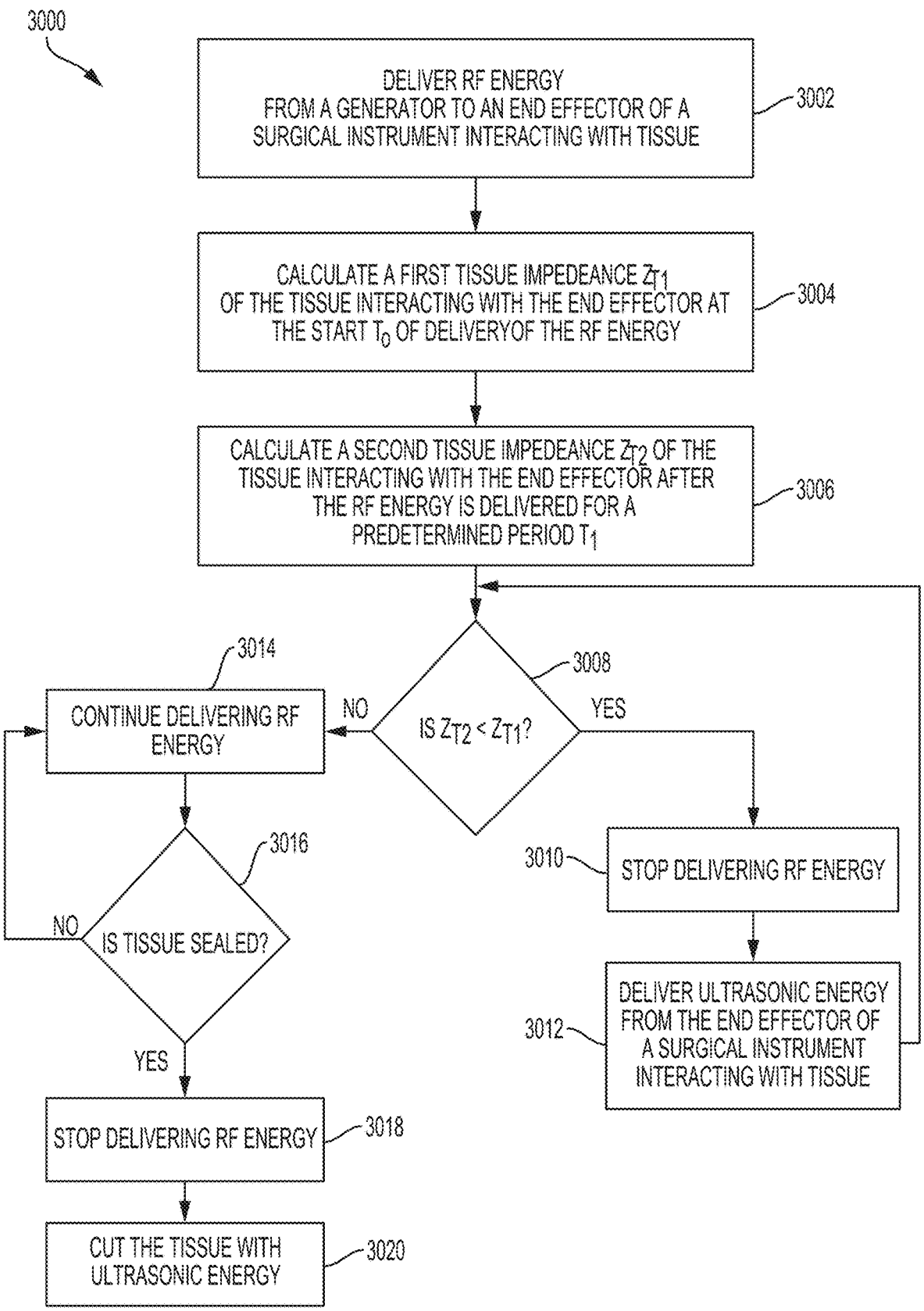
Figure 51:
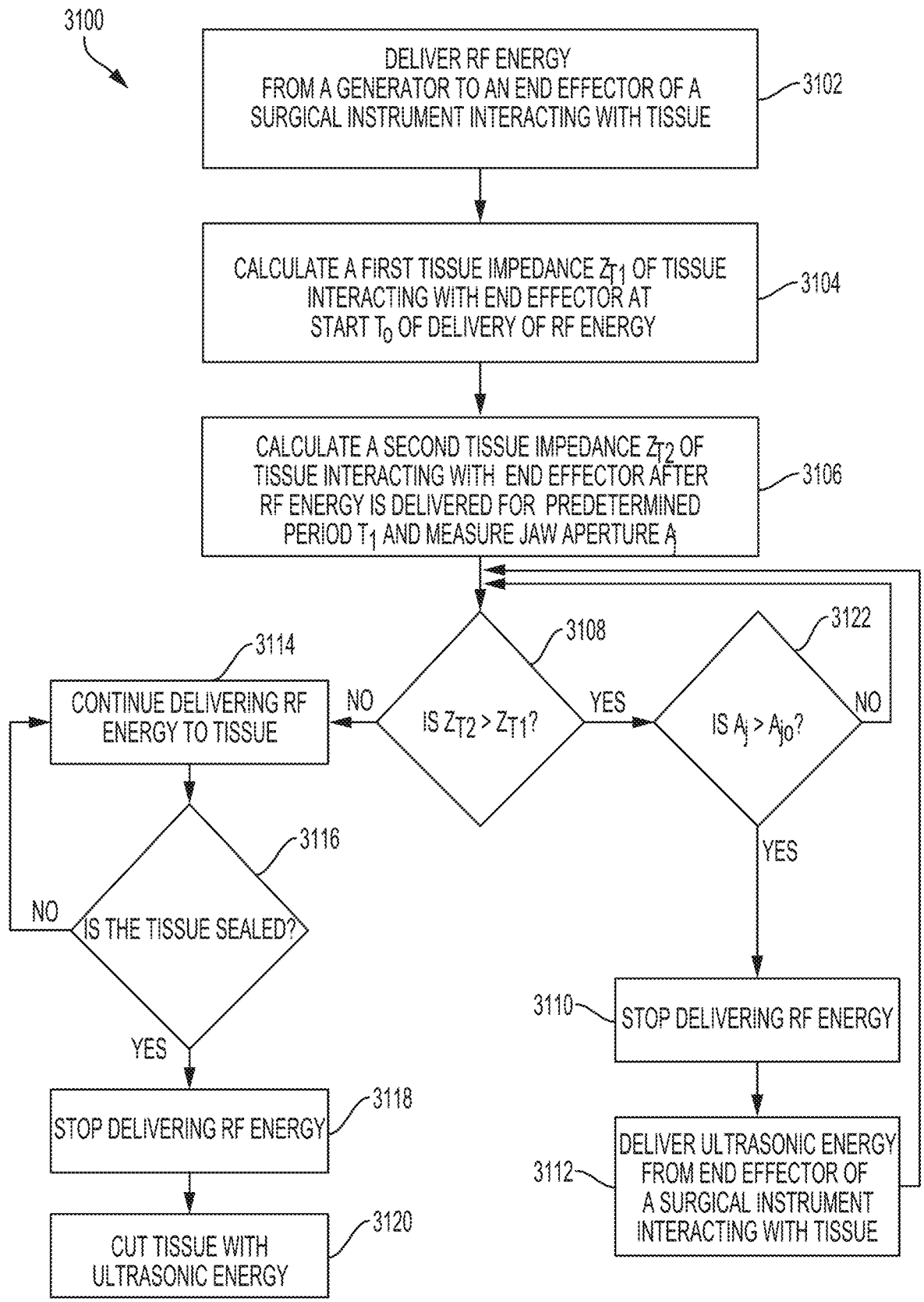
Figure 52:
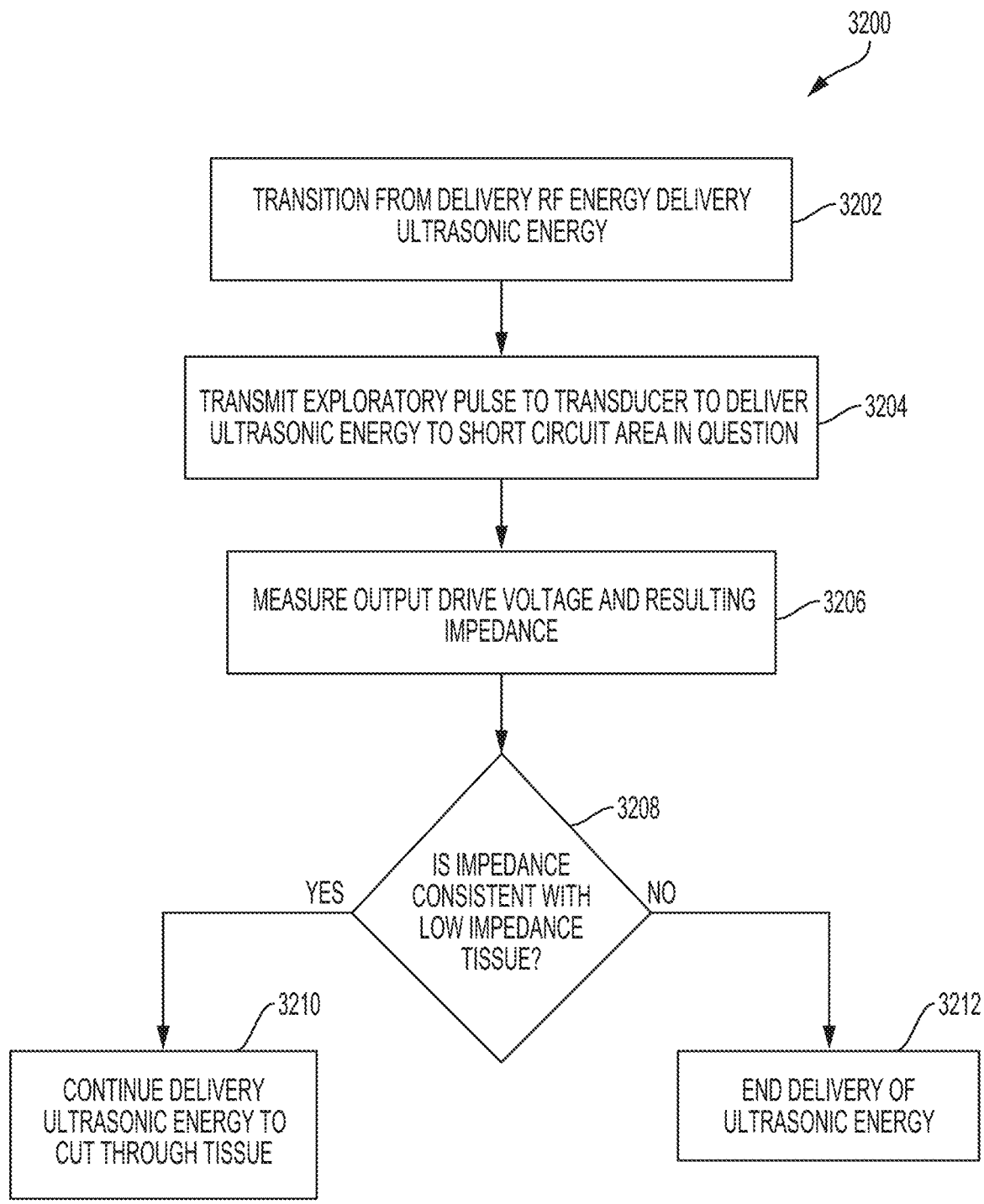
Figure 53:
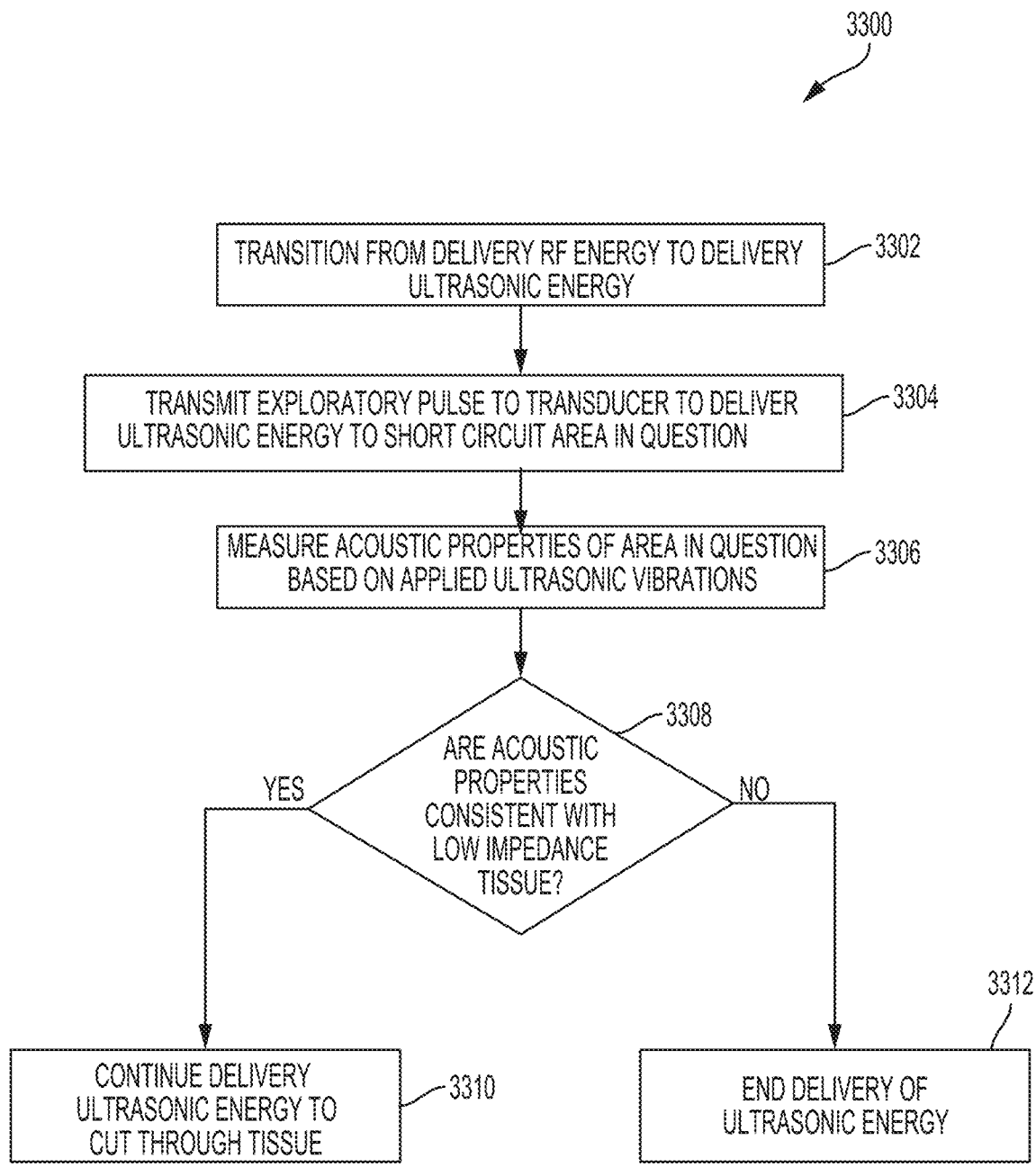
Figure 54:
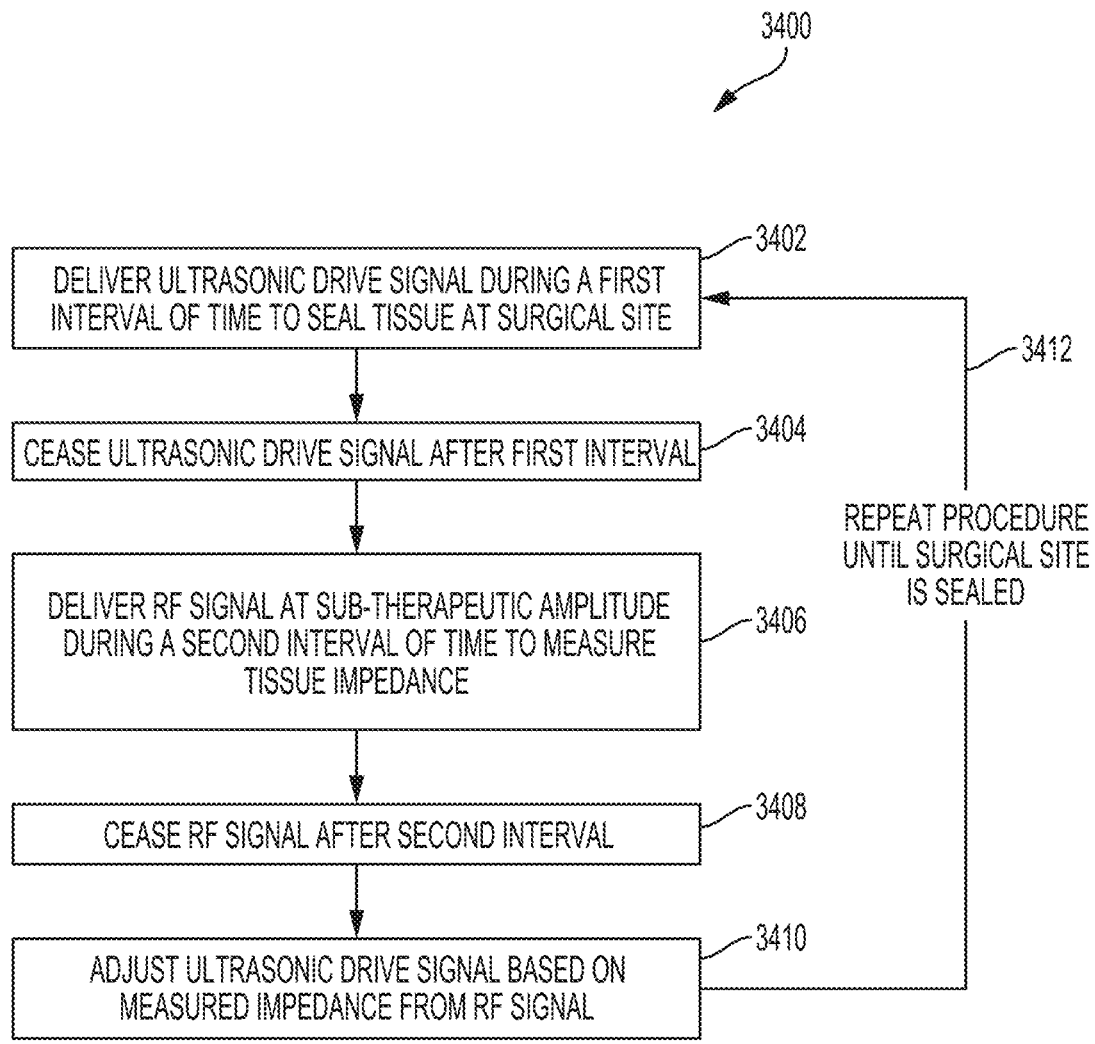
Figure 55:
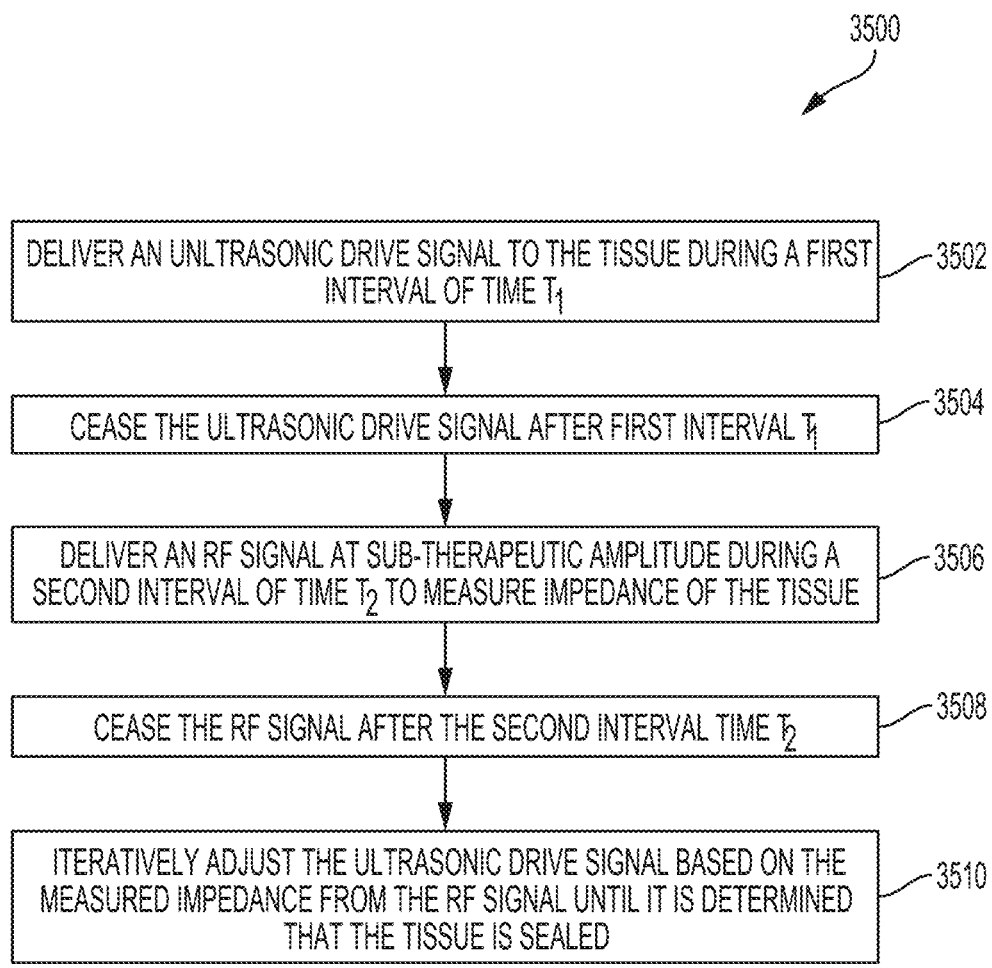
Figure 56:
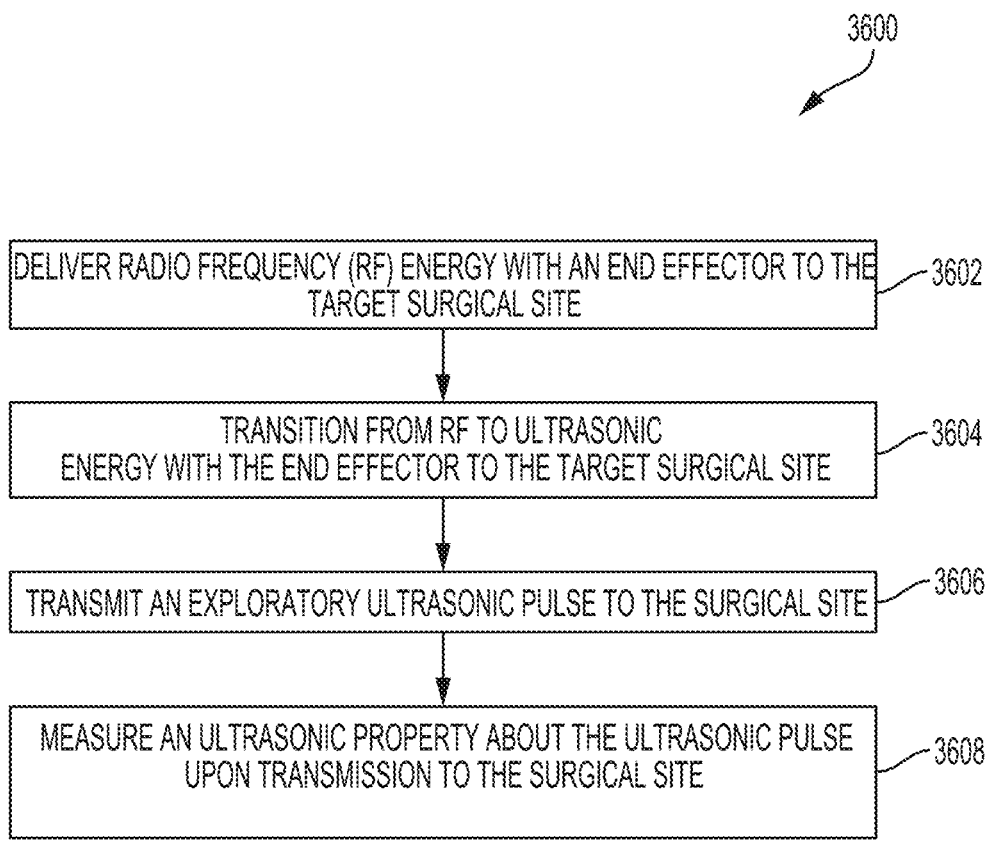
Figure 57:
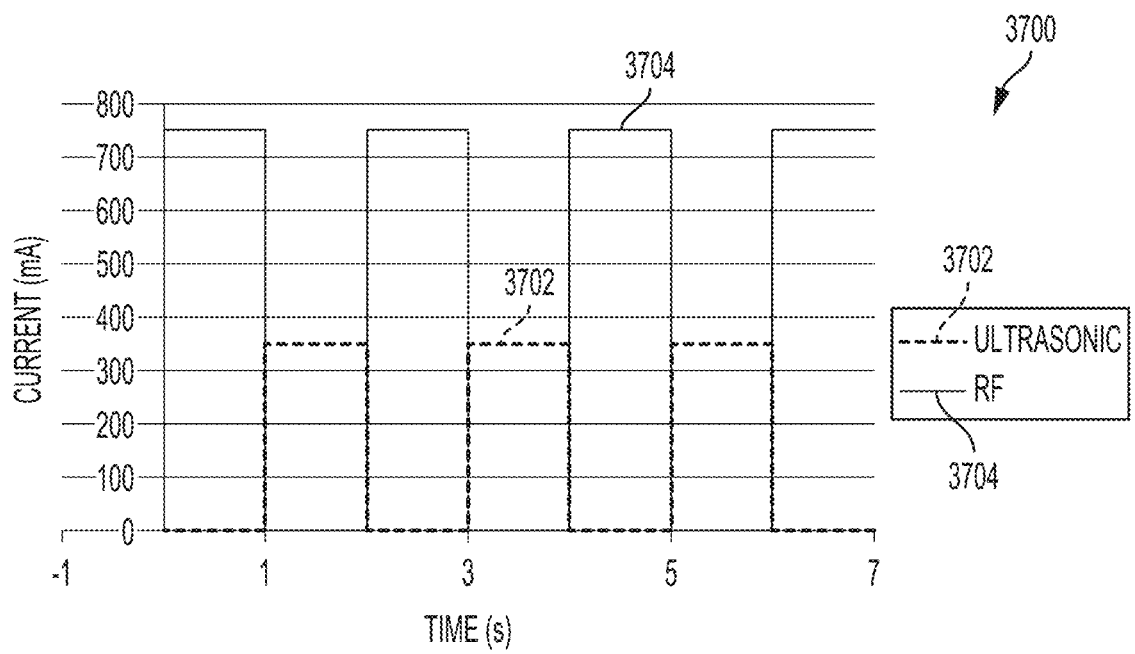
Figure 58:
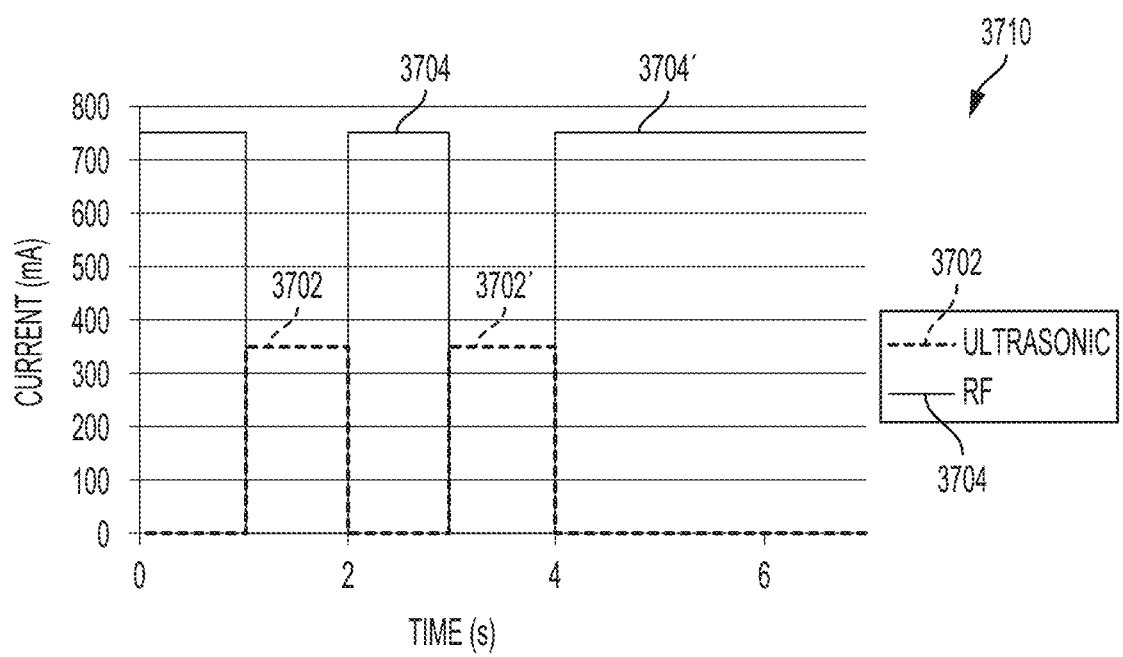
Figure 59:
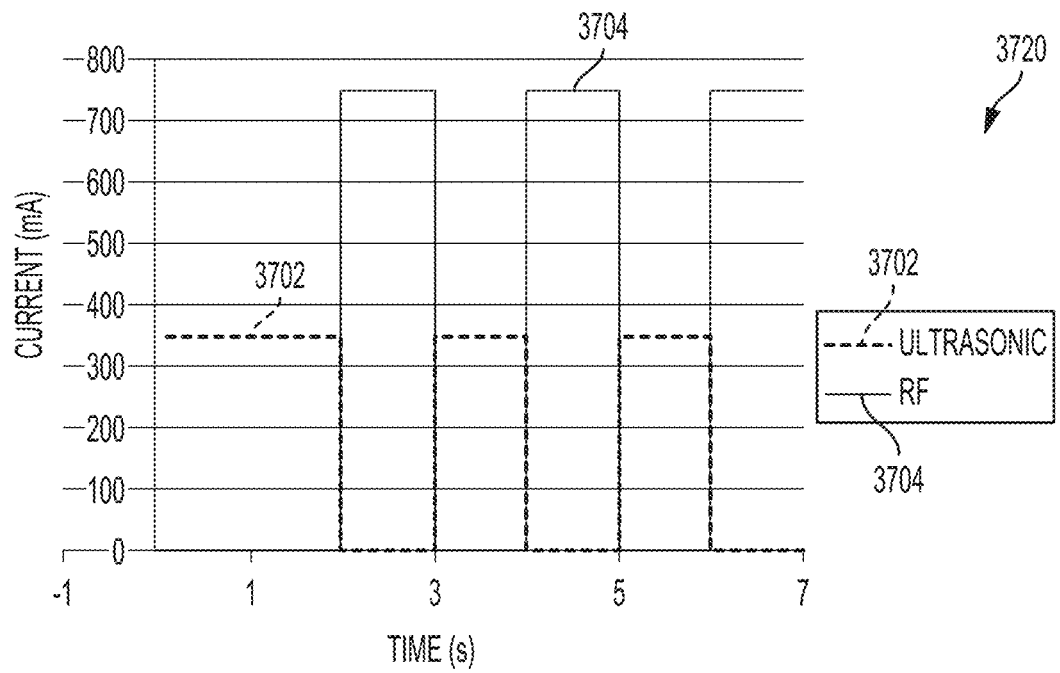
Figure 60:
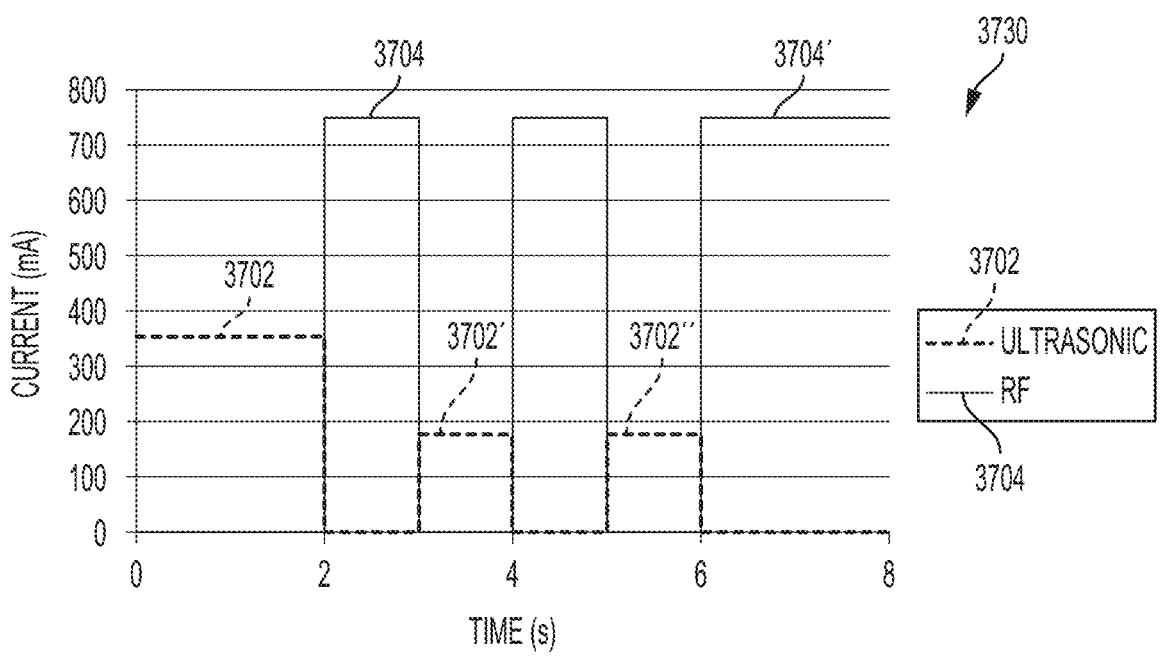
Figure 61:
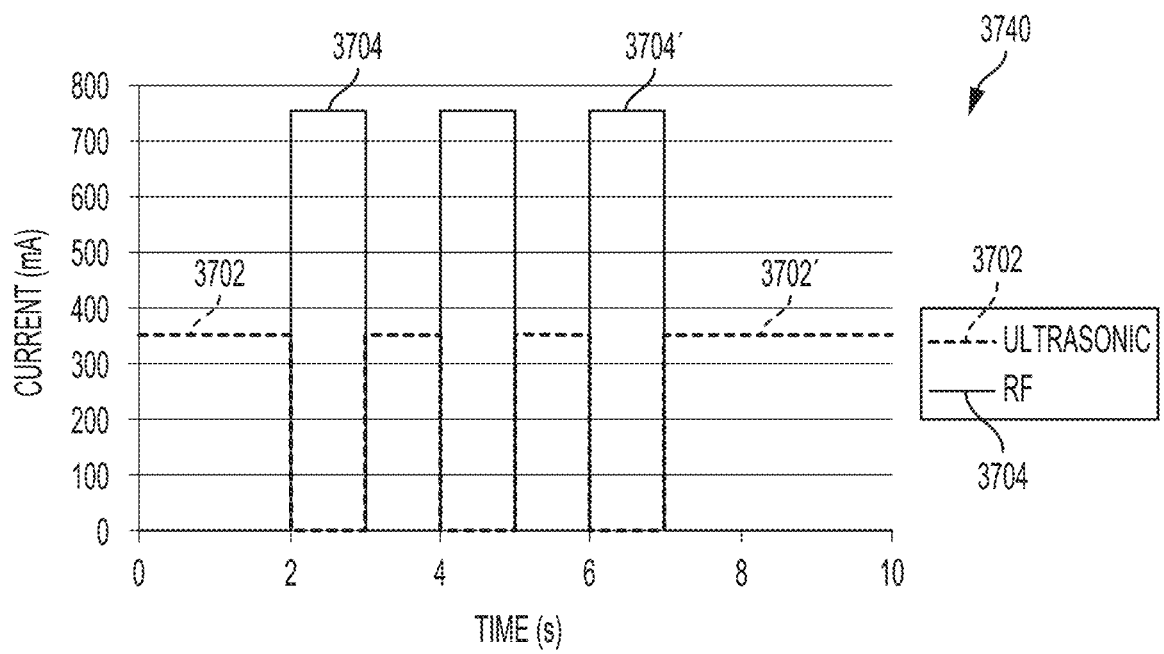
Figure 62:
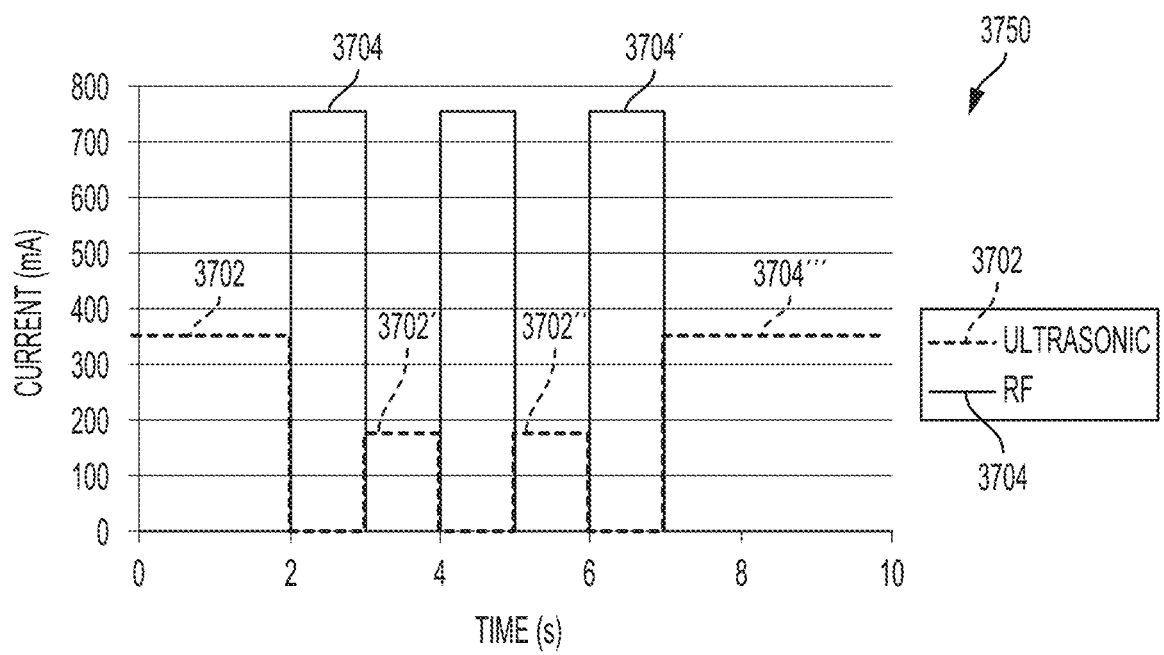
Figure 63:
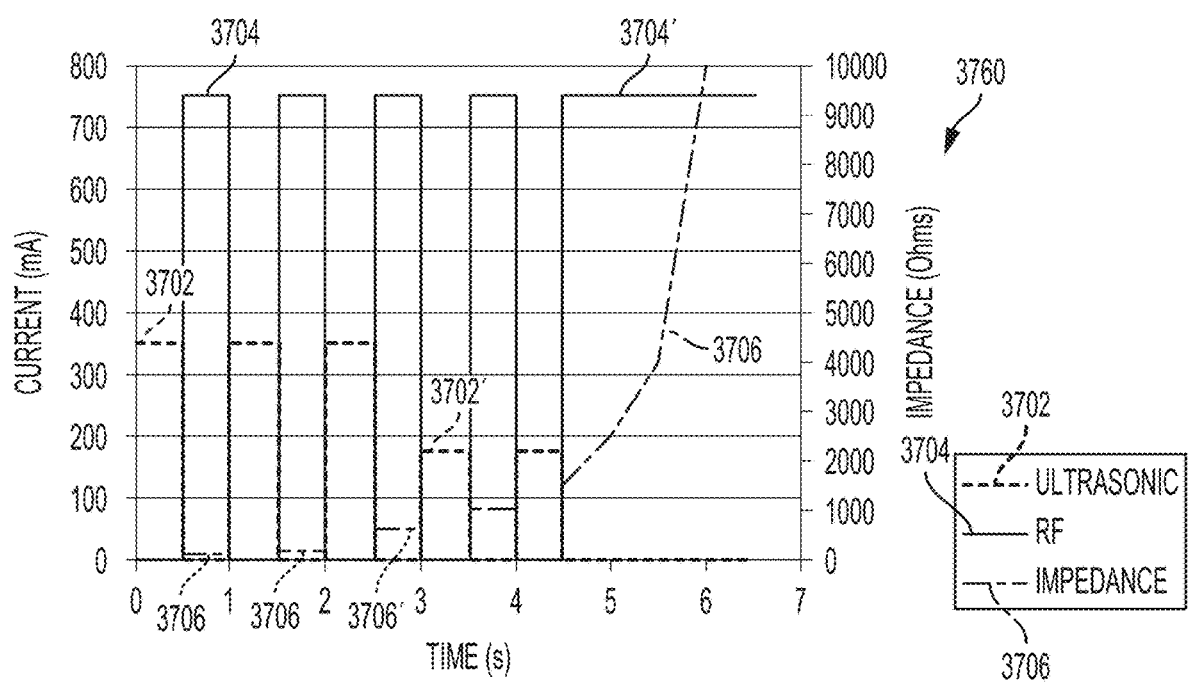
Figure 64:
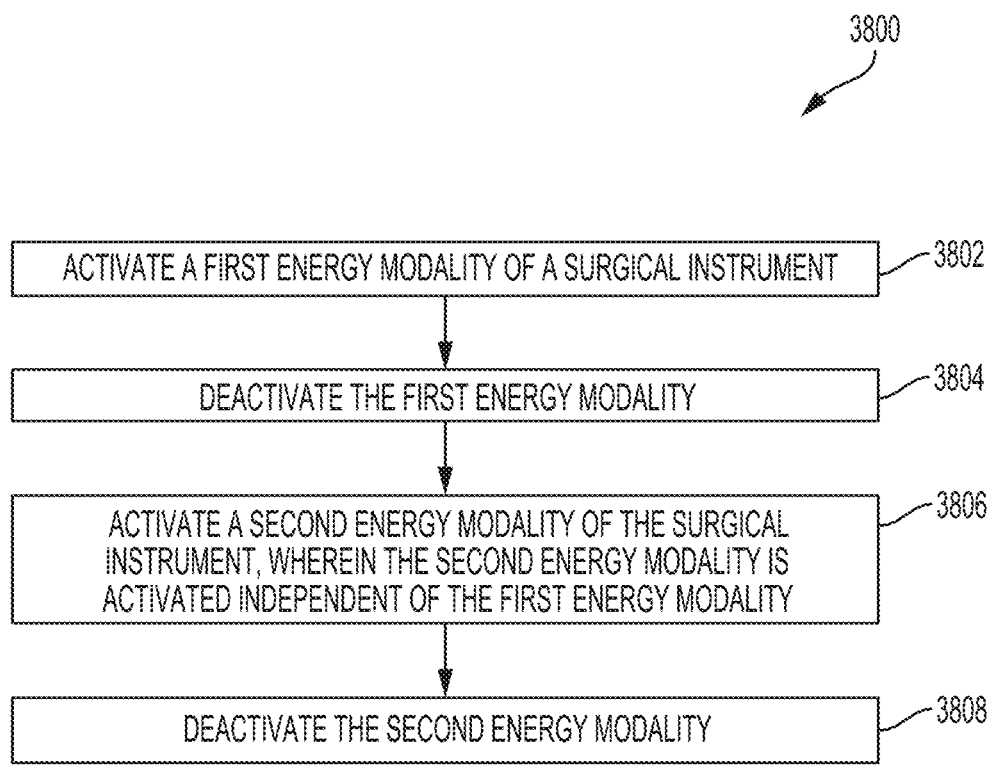
Figure 65:
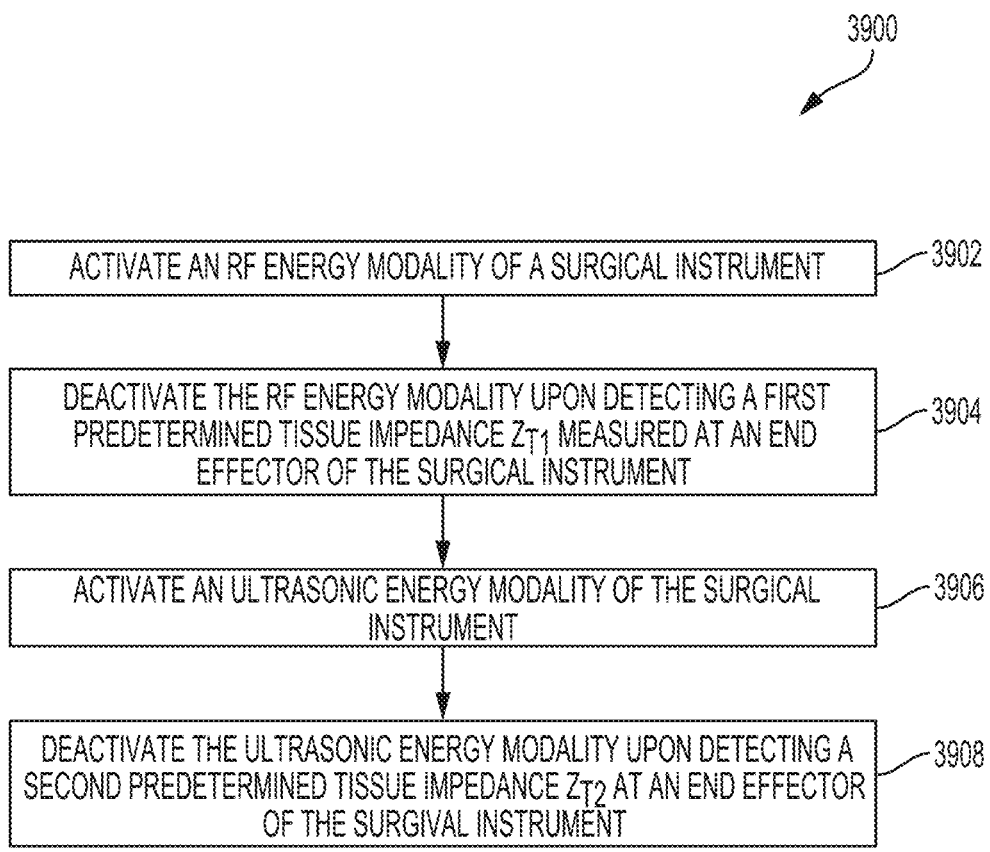
Figure 66:
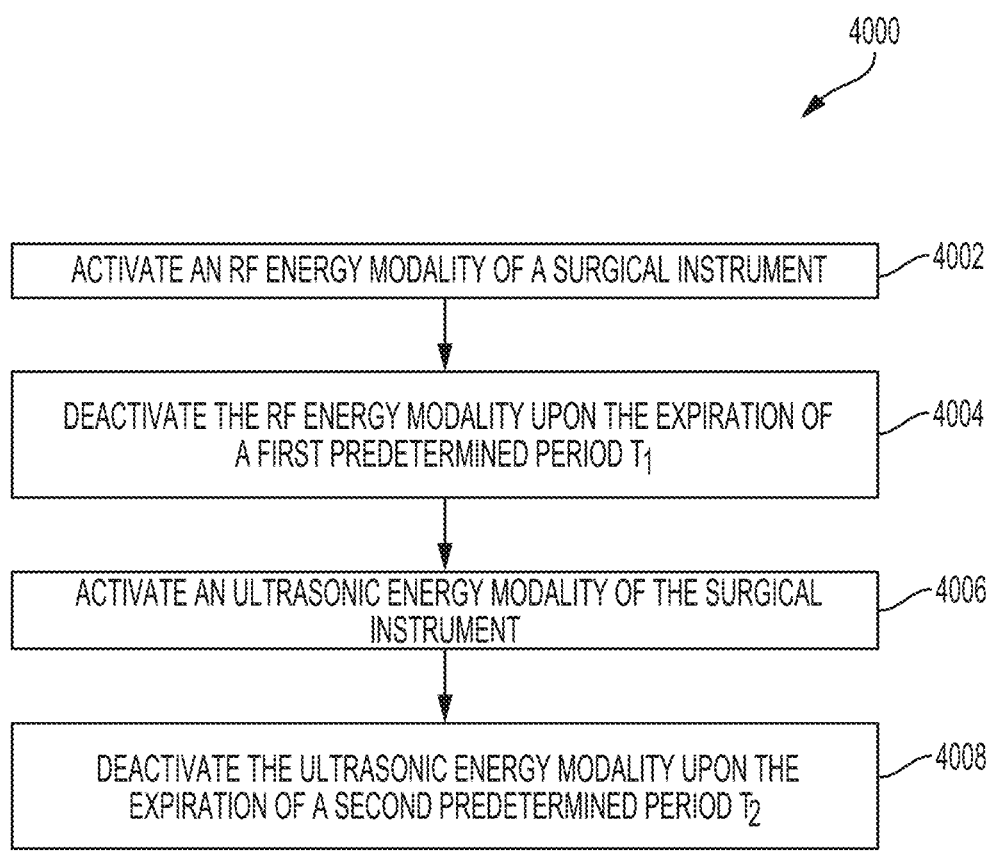
Figure 67:
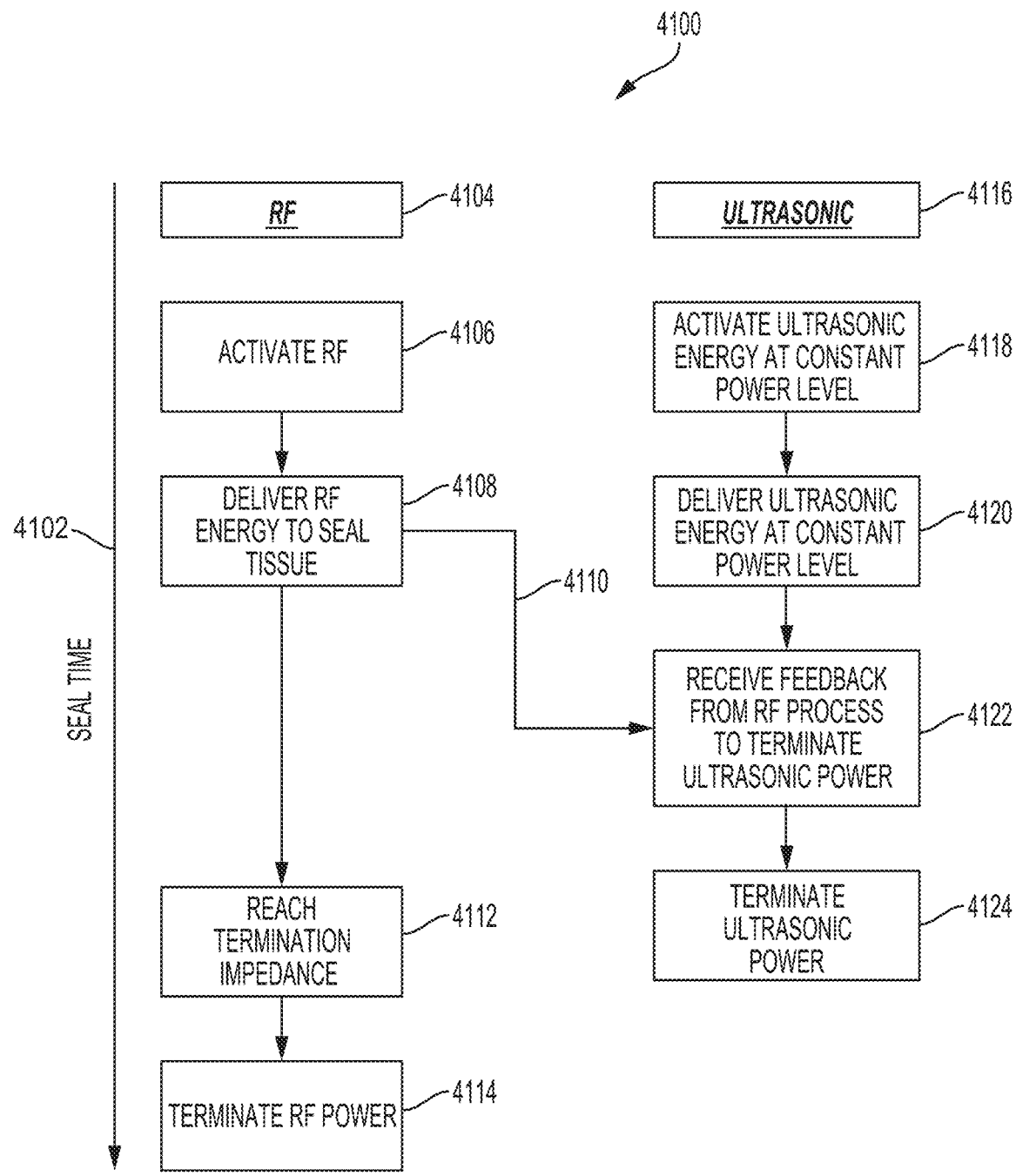
Figure 68:
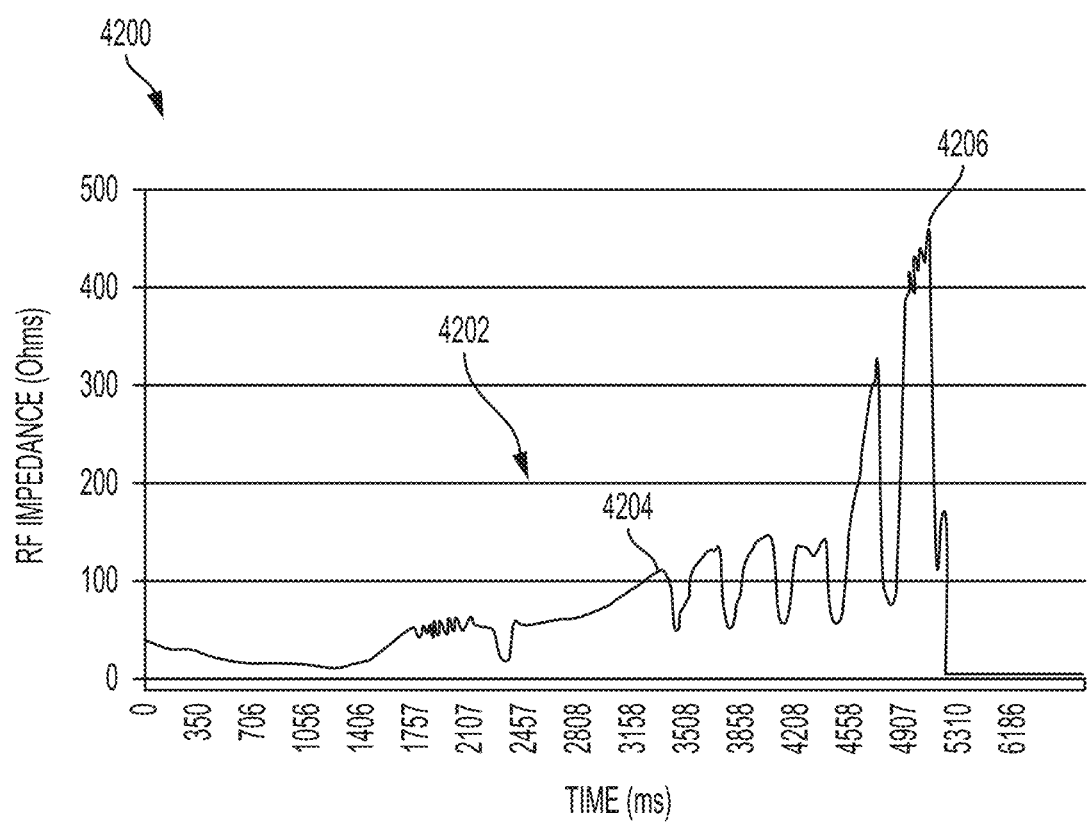
Figure 69:
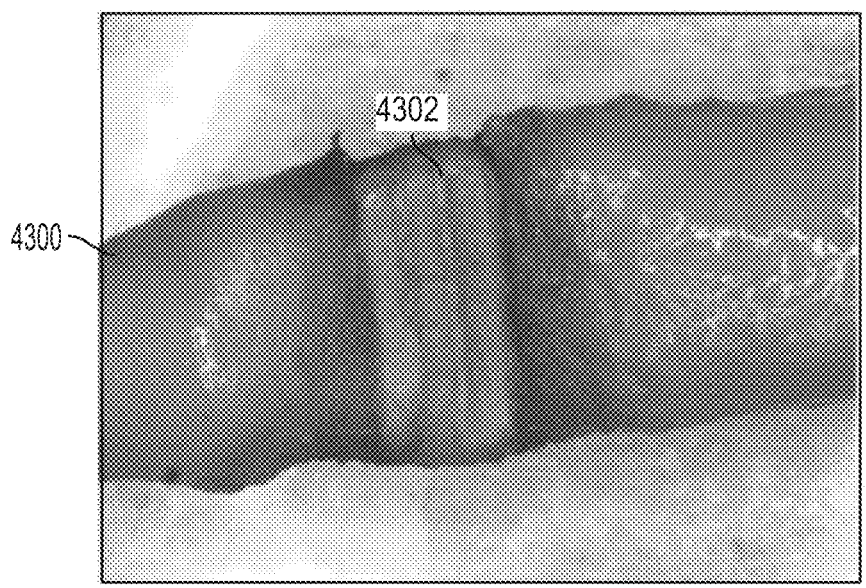
Figure 70:
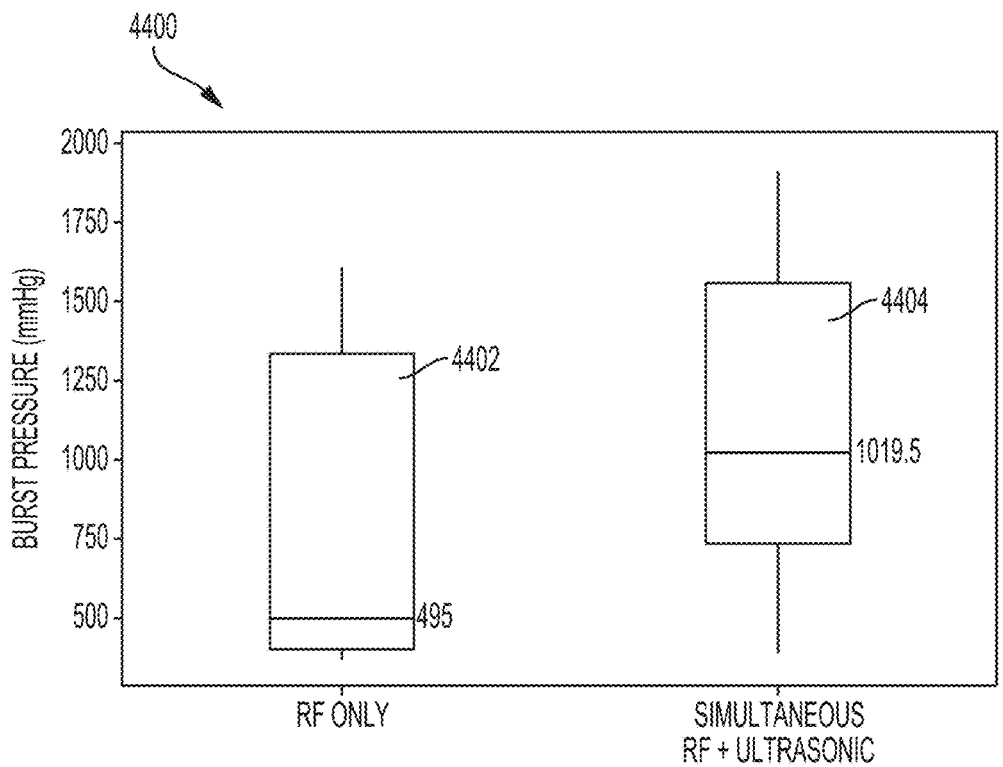
Figure 71:
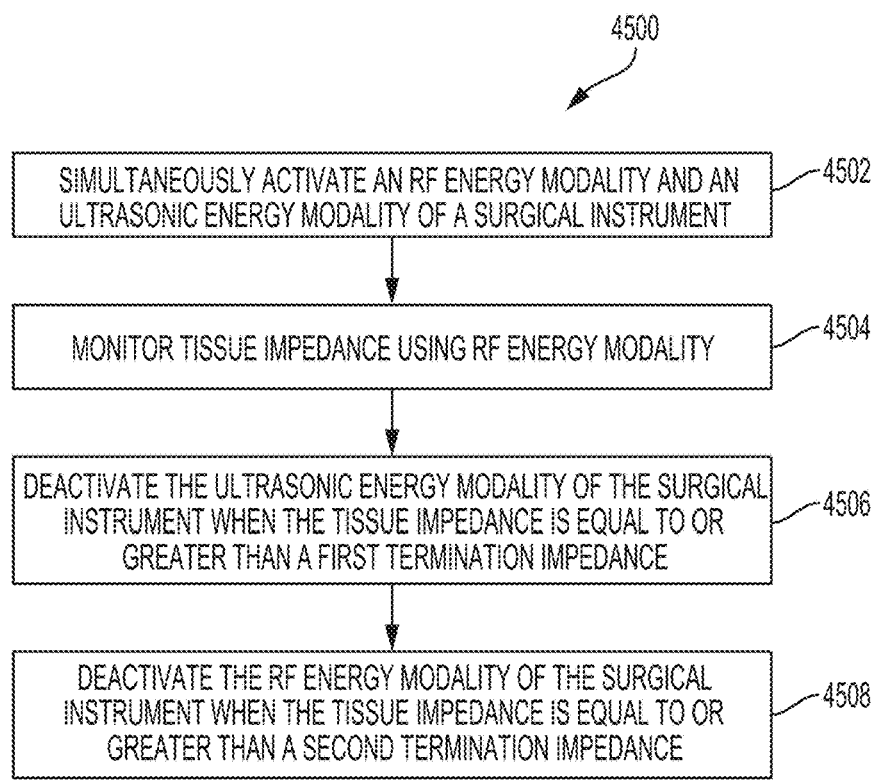
Figure 72:
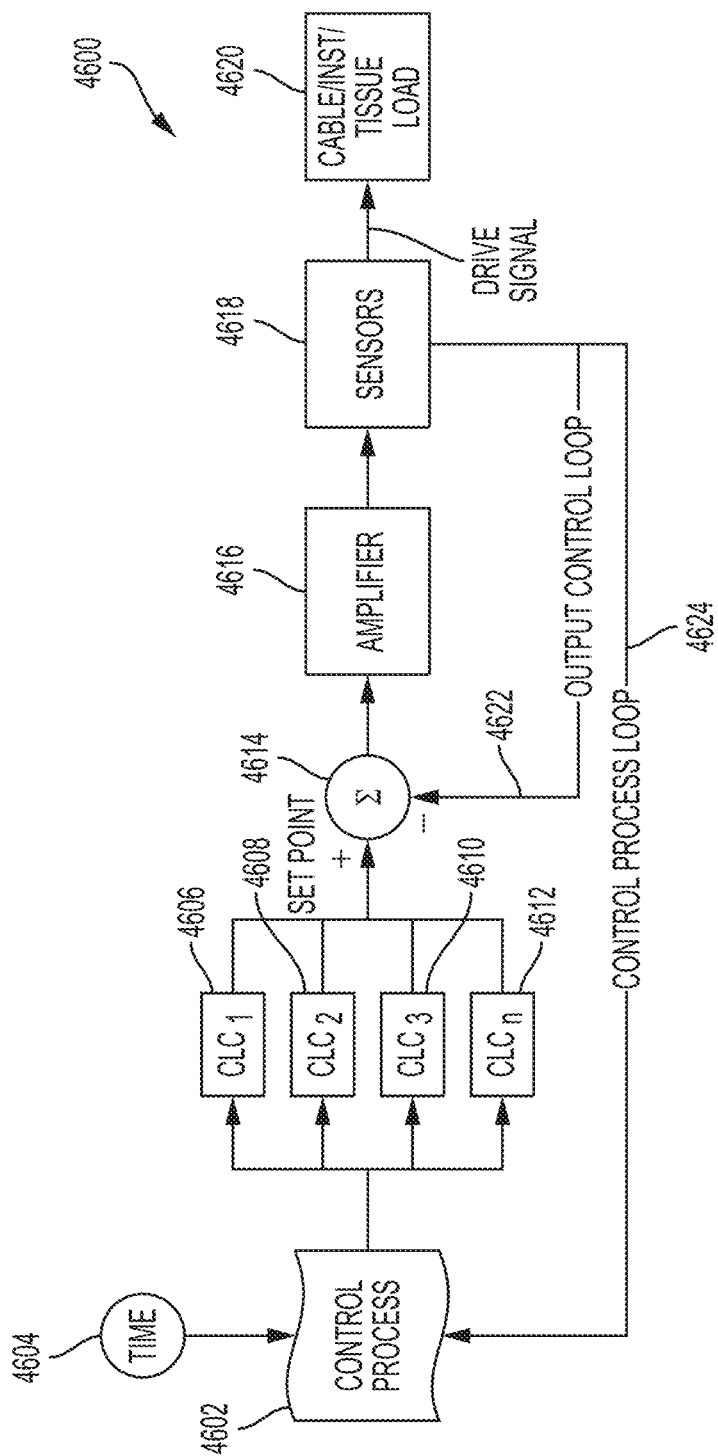
Figure 73:
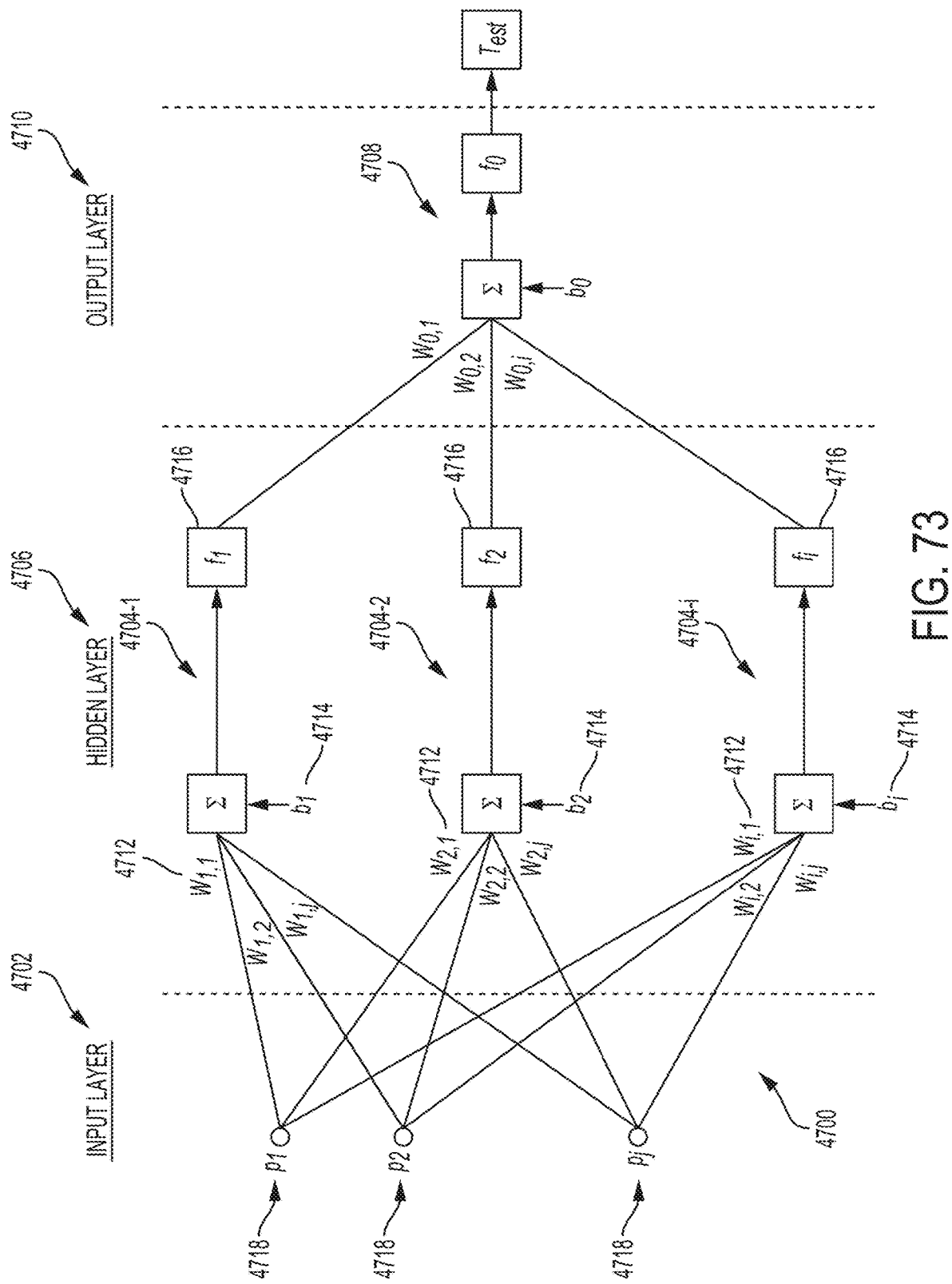

FIG. 43B also depicts example forces exerted by one aspect of an end-effector of a medical device compressing tissue;

FIG. 44 illustrates a logic flow diagram of one aspect of a feedback system;

FIG. 45 is a logic flow diagram of one aspect of a process for sealing or sealing and cutting large vessels or large tissue bundles;

FIG. 46 is a logic flow diagram of one aspect of a process for sealing or sealing and cutting large vessels or large tissue bundles by dynamically changing energy being delivered from the generator during the treatment of the tissue based on the changing aperture defined by the end effector;

FIG. 47 is a logic flow diagram of one aspect of a process for sealing or sealing and cutting large vessels or large tissue bundles by dynamically communicating energy parameters to the generator during the treatment of the tissue based on the changing aperture defined by the end effector of the surgical instrument;

FIG. 48 is a logic flow diagram of a technique to seal or seal and cut vessels using RF and ultrasonic energy in conjunction with tissue impedance measurements and the aperture defined by the clamp jaw measurements;

FIG. 49 is a logic flow diagram of one aspect of a method of dynamically changing the energy delivered to a surgical instrument based on a determination of a state of coagulation of tissue being treated by the surgical instrument;

FIG. 50 is a logic flow diagram of a technique to seal or seal and cut vessels using RF and ultrasonic energy in conjunction with tissue impedance measurements;

FIG. 51 is a logic flow diagram of a technique to seal or seal and cut vessels using RF and ultrasonic energy in conjunction with tissue impedance measurements and the aperture defined by the clamp jaw measurements;

FIG. 52 is a logic flow diagram of a technique for distinguishing a short circuit from low impedance tissue while utilizing RF energy by measuring voltage properties of an exploratory ultrasonic pulse;

FIG. 53 is a logic flow diagram of a technique for distinguishing a short circuit from low impedance tissue while delivering RF energy and measuring acoustic properties of an exploratory ultrasonic pulse, according to some aspects;

FIG. 54 is a logic flow diagram of a technique for conducting a tissue sealing technique without cutting by using a combination of ultrasonic energy and RF energy, according to some aspects;

FIG. 55 is a logic flow diagram of a technique for conducting a tissue sealing technique without cutting by using a combination of ultrasonic energy and RF energy, according to some aspects;

FIG. 56 is logic flow diagram 3600 of a technique for detecting low impedance tissue or metal shorts that may cause false short circuits in RF mode;

FIG. 57 is a timing diagram of a seal only pulse sequence illustrating a basic configuration of pulsing RF and ultrasonic energy for "Seal Only" mode;

FIG. 58 is a timing diagram of a seal only pulse sequence illustrating a basic configuration of pulsing RF and ultrasonic energy for "Seal Only" mode;

FIG. 59 is a timing diagram of a seal only pulse sequence;

FIG. 60 is a timing diagram of a seal only pulse sequence;

FIG. 61 is a timing diagram of a seal and cut pulse sequence, which begins and ends with ultrasonic energy pulses delivered at the same amplitude during the sealing a cutting cycles;

FIG. 62 is a timing diagram of a seal and cut pulse sequence, which begins and ends with ultrasonic energy pulses delivered at variable amplitude during the sealing a cutting cycles;

FIG. 63 is a timing diagram of a seal only pulse sequence where the ultrasonic energy pulse current is be set based on the impedance measured with the preceding RF energy pulse;

FIG. 64 is a logic flow diagram of a technique for delivering pulses of different energy modalities to tissue;

FIG. 65 is a logic flow diagram of a technique for delivering pulses of different energy modalities to tissue;

FIG. 66 is a logic flow diagram of a technique for delivering pulses of different energy modalities to tissue;

FIG. 67 is a logic flow diagram of one aspect of a process of applying simultaneous activation of different energy modalities to tissue;

FIG. 68 is a graphical representation of RF Impedance versus Time in connection with the logic flow diagram of FIG. 67 to illustrate the ultrasonic termination impedance;

FIG. 69 illustrates an example of the quality of a seal made in a vessel using the simultaneous activation of RF and ultrasonic energy modalities as described in connection with FIGS. 67 and 68;

FIG. 70 is a graphical representation of seal burst pressure of carotid bundles versus an RF only seal and a simultaneous RF/ultrasonic seal as described in connection with FIGS. 67-69;

FIG. 71 is a logic flow diagram of a process of simultaneous activation of RF and ultrasonic energy modalities;

FIG. 72 is a block diagram of one aspect describing the selection and application of composite load curves in a tissue seal control process; and FIG. 73 illustrates one aspect of a neural network for controlling a generator.

DESCRIPTION

Before explaining various forms of surgical instruments in detail, it should be noted that the illustrative forms are not limited in application or use to the details of construction and arrangement of parts illustrated in the accompanying drawings and description. The illustrative forms may be implemented or incorporated in other forms, variations and modifications, and may be practiced or carried out in various ways. Further, unless otherwise indicated, the terms and expressions employed herein have been chosen for the purpose of describing the illustrative forms for the convenience of the reader and are not for the purpose of limitation thereof.

Further, it is understood that any one or more of the following-described forms, expressions of forms, examples, can be combined with any one or more of the other following-described forms, expressions of forms, and examples.

Various forms are directed to improved ultrasonic and/or electrosurgical (RF) instruments configured for effecting tissue dissecting, cutting, and/or coagulation during surgical procedures. In one form, a combined ultrasonic and electrosurgical instrument may be configured for use in open surgical procedures, but has applications in other types of surgery, such as laparoscopic, endoscopic, and robotic-assisted procedures. Versatile use is facilitated by selective use of ultrasonic and RF energy.

The various forms will be described in combination with an ultrasonic instrument as described herein. Such description is provided by way of example, and not limitation, and is not intended to limit the scope and applications thereof. For example, any one of the described forms is useful in combination with a multitude of ultrasonic instruments including those described in, for example, U.S. Pat. Nos. 5,938,633; 5,935,144; 5,944,737; 5,322,055; 5,630,420; and 5,449,370.

As will become apparent from the following description, it is contemplated that forms of the surgical instruments described herein may be used in association with an oscillator unit of a surgical system, whereby ultrasonic energy from the oscillator unit provides the desired ultrasonic actuation for the present surgical instrument. It is also contemplated that forms of the surgical instrument described herein may be used in association with a signal generator unit of a surgical system, whereby electrical energy in the form of radio frequencies (RF), for example, is used to provide feedback to the user regarding the surgical instrument. The ultrasonic oscillator and/or the signal generator unit may be non-detachably integrated with the surgical instrument or may be provided as separate components, which can be electrically attachable to the surgical instrument.

One form of the present surgical apparatus is particularly configured for disposable use by virtue of its straightforward construction. However, it is also contemplated that other forms of the present surgical instrument can be configured for non-disposable or multiple uses. Detachable connection of the present surgical instrument with an associated oscillator and signal generator unit is presently disclosed for single-patient use for illustrative purposes only. However, non-detachable integrated connection of the present surgical instrument with an associated oscillator and/or signal generator unit is also contemplated. Accordingly, various forms of the presently described surgical instruments may be configured for single use and/or multiple use with either detachable and/or non-detachable integral oscillator and/or signal generator unit, without limitation, and all combinations of such configurations are contemplated to be within the scope of the present disclosure.

The surgical instruments disclosed herein are related to surgical instruments described in the following commonly owned applications and filed concurrently herewith: U.S. patent application Ser. No. 15/177,439, titled "Surgical System With User Adaptable Techniques Based On Tissue Type" by Stulen et al., now U.S. Patent Application Publication No. 2017/0000516, U.S. patent application Ser. No. 15/177,430, titled "Surgical System With User Adaptable Techniques" by Yates et al., now U.S. Patent Application Publication No. 2017/0000541, U.S. patent application Ser. No. 15/177,456, titled "Surgical System With User Adaptable Techniques Based On Tissue Impedance" by Yates et al., now U.S. Pat. No. 10,898,256, and U.S. patent application Ser. No. 15/177,466, titled "Surgical System With User Adaptable Techniques Employing Simultaneous Energy Modalities Based On Tissue Parameters" by Yates et al., now U.S. Pat. No. 10,765,470, each of which is incorporated herein by reference in its entirety.

Figure 1:
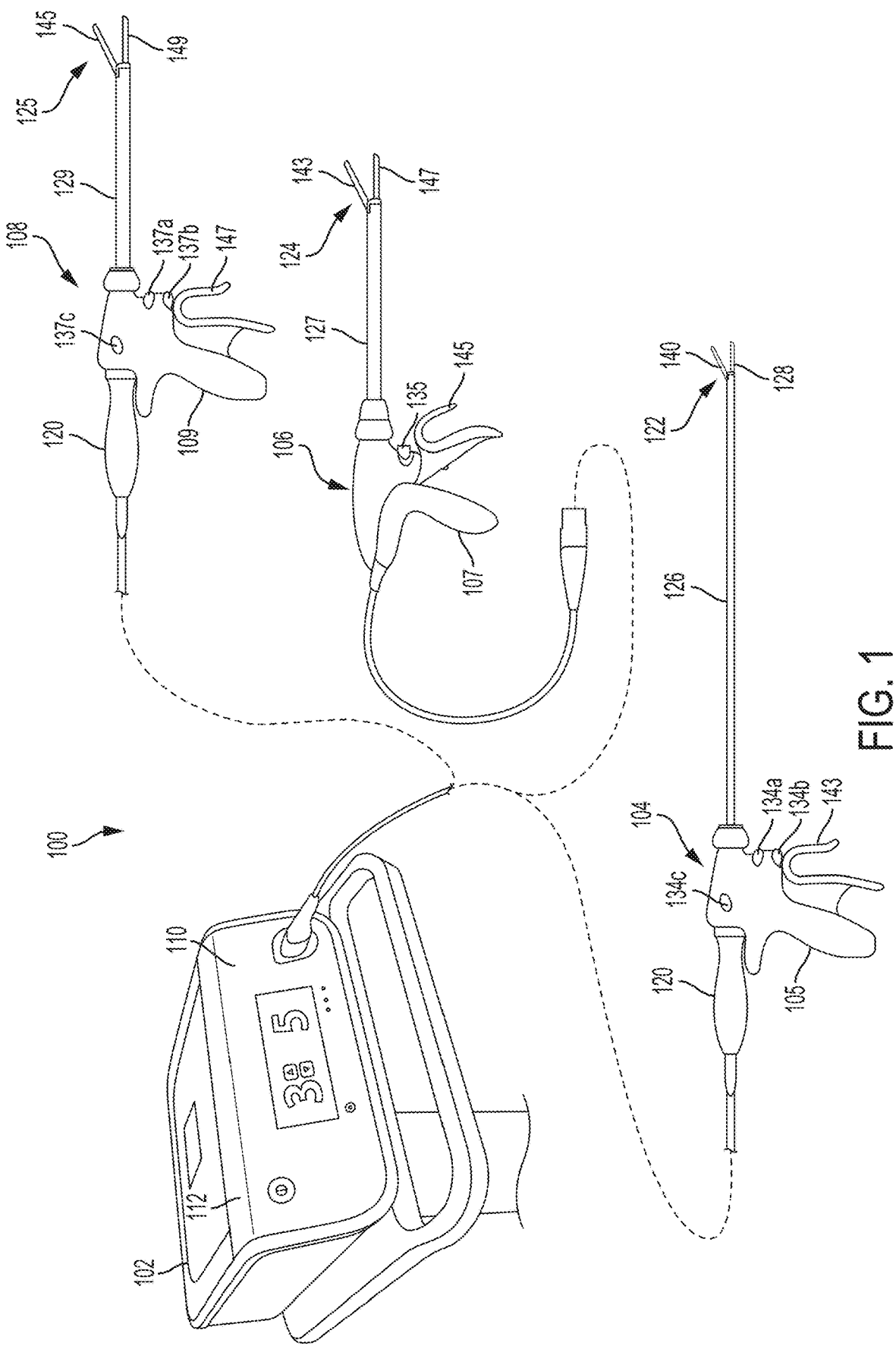
FIG. 1 illustrates one aspect of a surgical system comprising a generator and various surgical instruments usable therewith.
Figure 2:
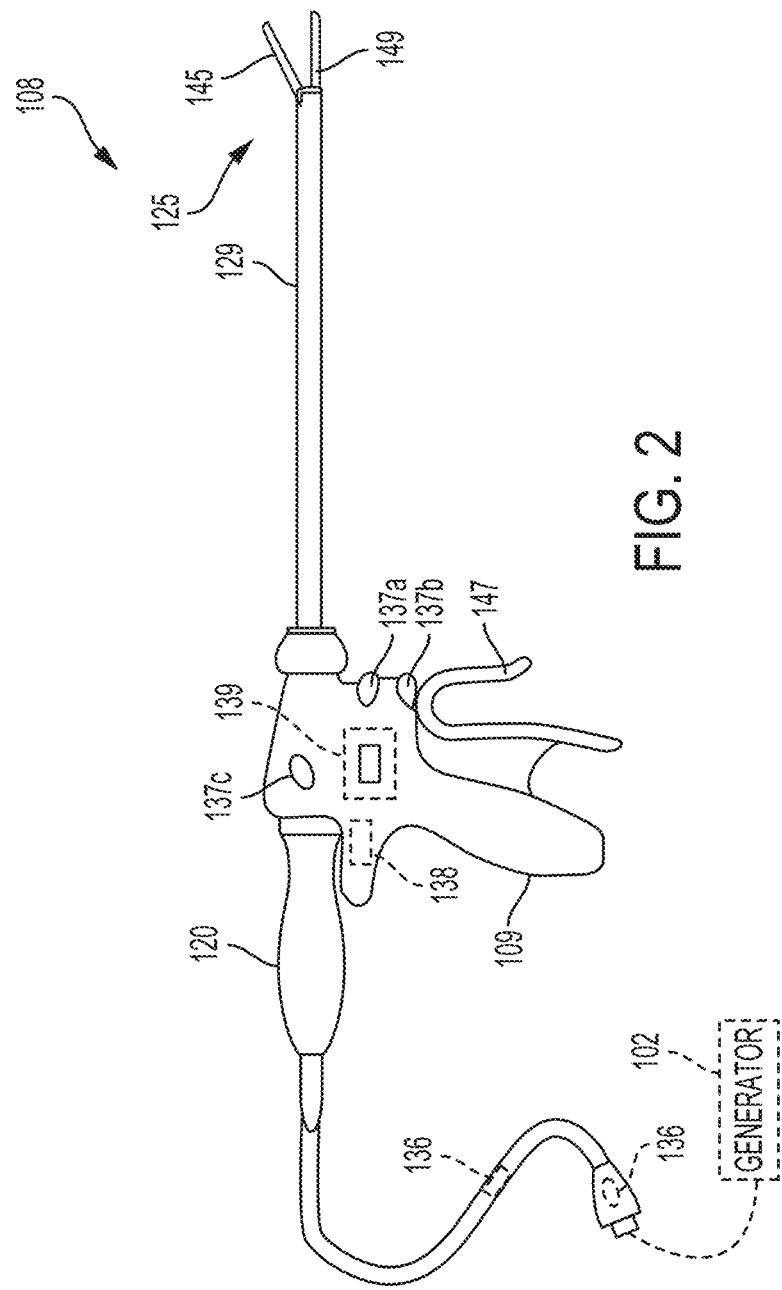
FIG. 2 is a diagram of one aspect of the ultrasonic surgical instrument of FIG. 16.

With reference to FIGS. 1-5, one form of a surgical system 10 including an ultrasonic surgical instrument is illustrated. FIG. 1 illustrates one form of a surgical system 100 comprising a generator 102 and various surgical instruments 104, 106, 108 usable therewith. FIG. 2 is a diagram of the ultrasonic surgical instrument 104 of FIG. 1.

FIG. 1 illustrates a generator 102 configured to drive multiple surgical instruments 104, 106, 108. The first surgical instrument 104 comprises a handpiece 105, an ultrasonic transducer 120, a shaft 126, and an end effector 122. The end effector 122 comprises an ultrasonic blade 128 acoustically coupled to the transducer 120 and a clamp arm 140. The handpiece 105 comprises a trigger 143 to operate the clamp arm 140 and a combination of the toggle buttons 134a, 134b, 134c to energize and drive the ultrasonic blade 128 or other function. The toggle buttons 134a, 134b, 134c can be configured to energize the ultrasonic transducer 120 with the generator 102.

Still with reference to FIG. 1, the generator 102 also is configured to drive a second surgical instrument 106. The second surgical instrument 106 is an RF electrosurgical instrument and comprises a handpiece 107, a shaft 127, and an end effector 124. The end effector 124 comprises electrodes in the clamp arms 143 and return through the ultrasonic blade 149. The electrodes are coupled to and energized by a bipolar energy source within the generator 102. The handpiece 107 comprises a trigger 147 to operate the clamp arm 145 and an energy button 135 to actuate an energy switch to energize the electrodes in the end effector 124.

Still with reference to FIG. 1, the generator 102 also is configures to drive a combination electrosurgical and ultrasonic instrument 108. The combination electrosurgical and ultrasonic multifunction surgical instrument 108 comprises a handpiece 109, a shaft 129, and an end effector 125. The end effector comprises an ultrasonic blade 149 and a clamp arm 145. The ultrasonic blade 149 is acoustically coupled to the ultrasonic transducer 120. The handpiece 109 comprises a trigger 147 to operate the clamp arm 145 and a combination of the toggle buttons 137a, 137b, 137c to energize and drive the ultrasonic blade 149 or other function. The toggle buttons 137a, 137b, 137c can be configured to energize the ultrasonic transducer 120 with the generator 102 and energize the ultrasonic blade 149 with a bipolar energy source also contained within the generator 102.

With reference to both FIGS. 1 and 2, the generator 102 is configurable for use with a variety of surgical devices. According to various forms, the generator 102 may be configurable for use with different surgical devices of different types including, for example, the ultrasonic surgical instrument 104, the electrosurgical or RF surgical devices, such as, the RF electrosurgical instrument 106, and the multifunction surgical instrument 108 that integrate electrosurgical RF and ultrasonic energies delivered simultaneously from the generator 102. Although in the form of FIG. 1, the generator 102 is shown separate from the surgical instruments 104, 106, 108, in one form, the generator 102 may be formed integrally with either of the surgical instrument 104, 106, 108 to form a unitary surgical system. The generator 102 comprises an input device 110 located on a front panel of the generator 102 console. The input device 110 may comprise any suitable device that generates signals suitable for programming the operation of the generator 102. The generator 102 also may comprise one or more output devices 112.

The generator 102 is coupled to an ultrasonic transducer 120 via a cable 144. The ultrasonic transducer 120 and a waveguide extending through a shaft 126 (waveguide not shown in FIG. 2) may collectively form an ultrasonic drive system driving an ultrasonic blade 128 of an end effector 122. The end effector 122 further may comprise a clamp arm 140 to clamp tissue between the clamp arm 140 and the ultrasonic blade 128. In one form, the generator 102 may be configured to produce a drive signal of a particular voltage, current, and/or frequency output signal that can be stepped or otherwise modified with high resolution, accuracy, and repeatability.

Still with reference to FIG. 2, It will be appreciated that a surgical instrument 104 may comprise any combination of the toggle buttons 134*a*, 134*b*, 134*c*. For example, the surgical instrument 104 could be configured to have only two toggle buttons: a toggle button 134*a* for producing maximum ultrasonic energy output and a toggle button 134*c* for producing a pulsed output at either the maximum or less than maximum power level. In this way, the drive signal output configuration of the generator 102 could be 5 continuous signals and 5 or 4 or 3 or 2 or 1 pulsed signals. In certain forms, the specific drive signal configuration may be controlled based upon, for example, EEPROM settings in the generator 102 and/or user power level selection(s).

In certain forms, a two-position switch may be provided as an alternative to a toggle button 134*c*. For example, a surgical instrument 104 may include a toggle button 134*a* for producing a continuous output at a maximum power level and a two-position toggle button 134*b*. In a first detented position, toggle button 134*b* may produce a continuous output at a less than maximum power level, and in a second detented position the toggle button 134*b* may produce a pulsed output (e.g., at either a maximum or less than maximum power level, depending upon the EEPROM settings).

Still with reference to FIG. 2, forms of the generator 102 may enable communication with instrument-based data circuits. For example, the generator 102 may be configured to communicate with a first data circuit 136 and/or a second data circuit 138. For example, the first data circuit 136 may indicate a burn-in frequency slope, as described herein. Additionally or alternatively, any type of information may be communicated to second data circuit for storage therein via a data circuit interface (e.g., using a logic device). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 102 and provide an indication to a user (e.g., an LED indication or other visible indication) based on the received data. The second data circuit 138 contained in the multifunction surgical instrument 108 of a surgical device. In some forms, the second data circuit 138 may be implemented in a many similar to that of the first data circuit 136 described herein. An instrument interface circuit may comprise a second data circuit interface to enable this communication. In one form, the second data circuit interface may comprise a tri-state digital interface, although other interfaces also may be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information. In some forms, the second data circuit 138 may store information about the electrical and/or ultrasonic properties of an associated transducer 120, end effector 122, or ultrasonic drive system. Various processes and techniques described herein may be executed by a generator. It will be appreciated, however, that in certain example forms, all or a part of these processes and techniques may be performed by internal logic 139 of the multifunction surgical instrument 108.

Figure 3:
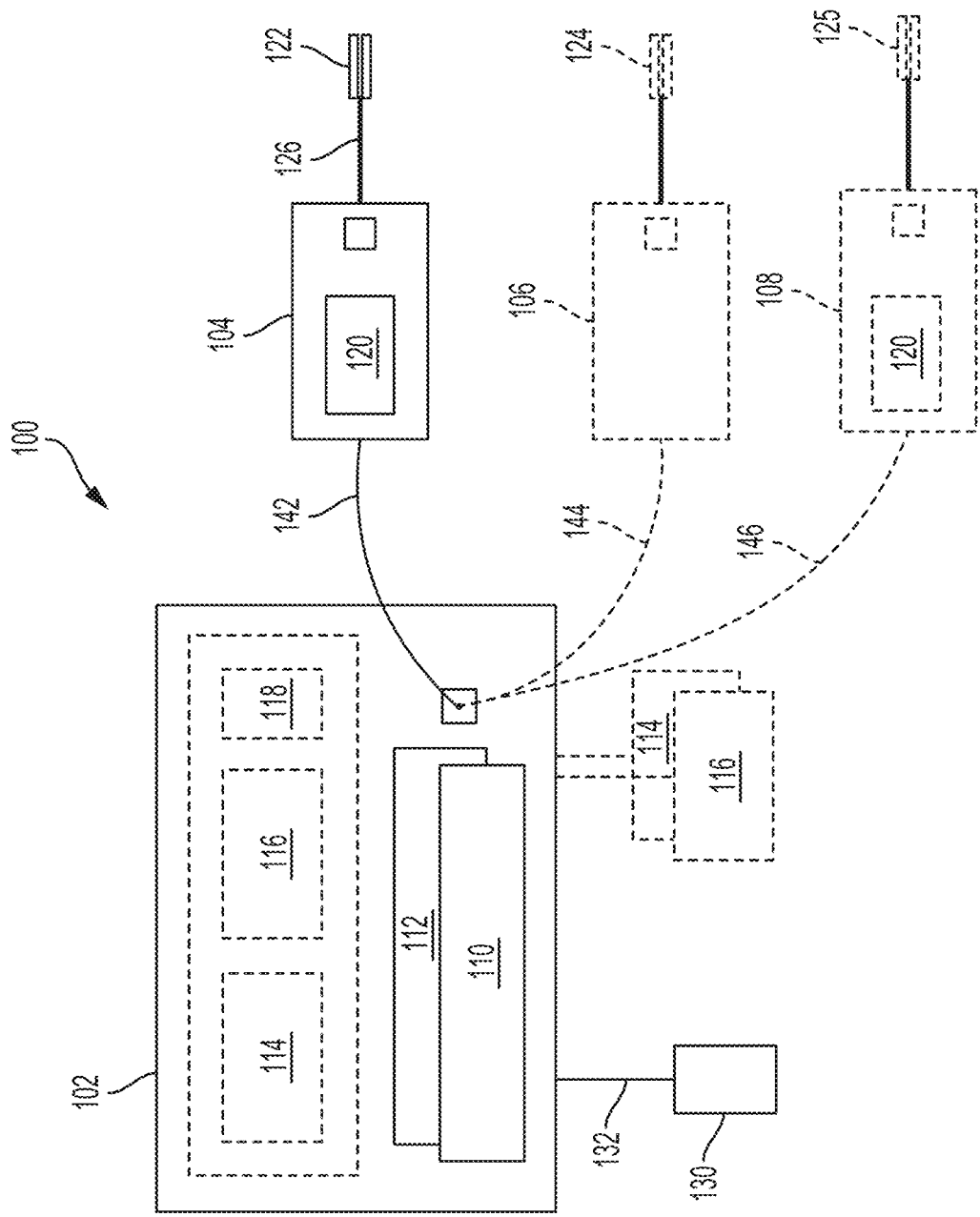
FIG. 3 is a diagram of one aspect of the surgical system of FIG. 16.

FIG. 3 is a diagram of the surgical system 100 of FIG. 1. In various forms, the generator 102 may comprise several separate functional elements, such as modules, circuits, and/or blocks. Different functional elements or modules may be configured for driving the different kinds of surgical instruments 104, 106, 108. For example, an ultrasonic generator drive circuit 114 may drive ultrasonic devices such as the ultrasonic surgical instrument 104 via a cable 142. An electrosurgery/RF generator drive circuit 116 may drive the electrosurgical instrument 106 via a cable 144. For example, the respective drive circuits 114, 116 may generate respective drive signals for driving the surgical instruments 104, 106, 108. In various forms, the ultrasonic generator drive circuit 114 (e.g., ultrasonic drive circuit) and/or the electrosurgery/RF generator drive circuit 116 (e.g., RF drive circuit) each may be formed integrally with the generator 102. Alternatively, one or more of the drive circuits 114, 116 may be provided as a separate circuit module electrically coupled to the generator 102. (The drive circuits 114 and 116 are shown in phantom to illustrate this option.) Also, in some forms, the electrosurgery/RF generator drive circuit 116 may be formed integrally with the ultrasonic generator drive circuit 114, or vice versa. Also, in some forms, the generator 102 may be omitted entirely and the drive circuits 114, 116 may be executed by processors or other hardware within the respective surgical instruments 104, 106, 108.

In other forms, the electrical outputs of the ultrasonic generator drive circuit 114 and the electrosurgery/RF generator drive circuit 116 may be combined into a single circuit to provide a single electrical signal capable of driving the multifunction surgical instrument 108 simultaneously with electrosurgical RF and ultrasonic energies via a cable 146. The multifunction surgical instrument 108 comprises an ultrasonic transducer 120 coupled to an ultrasonic blade 149 and one or more electrodes in the end effector 124 to receive electrosurgical RF energy. In such implementations, the combined RF/ultrasonic signal is coupled to the multifunction surgical instrument 108. The multifunction surgical instrument 108 comprises signal processing components to split the combined RF/ultrasonic signal such that the RF signal can be delivered to the electrodes in the end effector 124 and the ultrasonic signal can be delivered to the ultrasonic transducer 120.

In accordance with the described forms, the ultrasonic generator drive circuit 114 may produce a drive signal or signals of particular voltages, currents, and frequencies, e.g., 55,500 cycles per second (Hz). The drive signal or signals may be provided to the ultrasonic surgical instrument 104, and specifically to the transducer 120, which may operate, for example, as described herein. The transducer 120 and a waveguide extending through the shaft 126 (waveguide not shown in FIG. 2) may collectively form an ultrasonic drive system driving an ultrasonic blade 128 of an end effector 122. In one form, the generator 102 may be configured to produce a drive signal of a particular voltage, current, and/or frequency output signal that can be stepped or otherwise modified with high resolution, accuracy, and repeatability.

The generator 102 may be activated to provide the drive signal to the transducer 120 in any suitable manner. For example, the generator 102 may comprise a foot switch 130 coupled to the generator 102 via a foot switch cable 132. A clinician may activate the transducer 120 by depressing the foot switch 130. In addition, or instead of the foot switch 130 some forms of the ultrasonic surgical instrument 104 may utilize one or more switches positioned on the hand piece that, when activated, may cause the generator 102 to activate the transducer 120. In one form, for example, the one or more switches may comprise a pair of toggle buttons 134a, 134b (FIG. 2), for example, to determine an operating mode of the surgical instrument 104. When the toggle button 134a is depressed, for example, the ultrasonic generator 102 may provide a maximum drive signal to the transducer 120, causing it to produce maximum ultrasonic energy output. Depressing toggle button 134b may cause the ultrasonic generator 102 to provide a user-selectable drive signal to the transducer 120, causing it to produce less than the maximum ultrasonic energy output. The surgical instrument 104 additionally or alternatively may comprise a second switch (not shown) to, for example, indicate a position of a jaw closure trigger for operating jaws of the end effector 122. Also, in some forms, the ultrasonic generator 102 may be activated based on the position of the jaw closure trigger, (e.g., as the clinician depresses the jaw closure trigger to close the jaws, ultrasonic energy may be applied).

Additionally or alternatively, the one or more switches may comprises a toggle button 134c that, when depressed, causes the generator 102 to provide a pulsed output. The pulses may be provided at any suitable frequency and grouping, for example. In certain forms, the power level of the pulses may be the power levels associated with toggle buttons 134a, 134b (maximum, less than maximum), for example.

In accordance with the described forms, the electrosurgery/RF generator drive circuit 116 may generate a drive signal or signals with output power sufficient to perform bipolar electrosurgery using radio frequency (RF) energy. In bipolar electrosurgery applications, the drive signal may be provided, for example, to electrodes of the electrosurgical instrument 106, for example. Accordingly, the generator 102 may be configured for therapeutic purposes by applying electrical energy to the tissue sufficient for treating the tissue (e.g., coagulation, cauterization, tissue welding).

The generator 102 may comprise an input device 110 (FIG. 1) located, for example, on a front panel of the generator 102 console. The input device 110 may comprise any suitable device that generates signals suitable for programming the operation of the generator 102. In operation, the user can program or otherwise control operation of the generator 102 using the input device 110. The input device 110 may comprise any suitable device that generates signals that can be used by the generator (e.g., by one or more processors contained in the generator) to control the operation of the generator 102 (e.g., operation of the ultrasonic generator drive circuit 114 and/or electrosurgery/RF generator drive circuit 116). In various forms, the input device 110 includes one or more of buttons, switches, thumbwheels, keyboard, keypad, touch screen monitor, pointing device, remote connection to a general purpose or dedicated computer. In other forms, the input device 110 may comprise a suitable user interface, such as one or more user interface screens displayed on a touch screen monitor, for example. Accordingly, by way of the input device 110, the user can set or program various operating parameters of the generator, such as, for example, current (I), voltage (V), frequency (f), and/or period (T) of a drive signal or signals generated by the ultrasonic generator drive circuit 114 and/or electrosurgery/RF generator drive circuit 116.

The generator 102 also may comprise an output device 112 (FIGS. 1, 3), such as an output indicator, located, for example, on a front panel of the generator 102 console. The output device 112 includes one or more devices for providing a sensory feedback to a user. Such devices may comprise, for example, visual feedback devices (e.g., a visual feedback device may comprise incandescent lamps, light emitting diodes (LEDs), graphical user interface, display, analog indicator, digital indicator, bar graph display, digital alphanumeric display, LCD display screen, LED indicators), audio feedback devices (e.g., an audio feedback device may comprise speaker, buzzer, audible, computer generated tone, computerized speech, voice user interface (VUI) to interact with computers through a voice/speech platform), or tactile feedback devices (e.g., a tactile feedback device comprises any type of vibratory feedback, haptic actuator).

Although certain modules, circuits, and/or blocks of the generator 102 may be described by way of example, it can be appreciated that a greater or lesser number of modules, circuits, and/or blocks may be used and still fall within the scope of the forms. Further, although various forms may be described in terms of modules, circuits, and/or blocks to facilitate description, such modules, circuits, and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components. Also, in some forms, the various modules described herein may be implemented utilizing similar hardware positioned within the surgical instruments 104, 106, 108 (i.e., the generator 102 may be omitted).

In one form, the ultrasonic generator drive circuit 114 and electrosurgery/RF drive circuit 116 may comprise one or more embedded applications implemented as firmware, software, hardware, or any combination thereof. The drive circuits 114, 116 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one form, the drive circuits 114, 116 comprise a hardware component implemented as a processor for executing program instructions for monitoring various measurable characteristics of the surgical instruments 104, 106, 108 and generating a corresponding output control signals for operating the surgical instruments 104, 106, 108. In forms in which the generator 102 is used in conjunction with the surgical instrument 104, the output control signal may drive the ultrasonic transducer 120 in cutting and/or coagulation operating modes. Electrical characteristics of the surgical instrument 104 and/or tissue may be measured and used to control operational aspects of the generator 102 and/or provided as feedback to the user. In forms in which the generator 102 is used in conjunction with the electrosurgical instrument 106, the output control signal may supply electrical energy (e.g., RF energy) to the end effector 124 in cutting, coagulation and/or desiccation modes. Electrical characteristics of the electrosurgical instrument 106 and/or tissue may be measured and used to control operational aspects of the generator 102 and/or provide feedback to the user. In various forms, as previously discussed, the hardware component may be implemented as a DSP, PLD, ASIC, circuits, and/or registers. In one form, the processor may be configured to store and execute computer software program instructions to generate the output signal functions for driving various components of the surgical instruments 104, 106, 108, such as the ultrasonic transducer 120 and the end effectors 122, 124.

Figure 4:
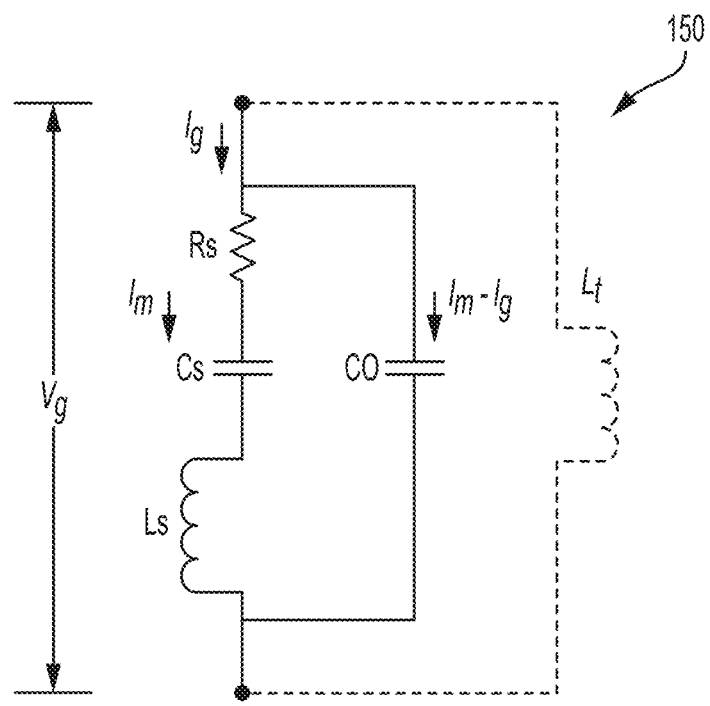
FIG. 4 is a model illustrating one aspect of a motional branch current.

FIG. 4 illustrates an equivalent circuit 150 of an ultrasonic transducer, such as the ultrasonic transducer 120 shown in FIGS. 1-3, according to one form. The circuit 150 comprises a first "motional" branch having a serially connected inductance $L_s$, resistance $R_s$ and capacitance $C_s$ that define the electromechanical properties of the resonator, and a second capacitive branch having a static capacitance $C_o$. Drive current $I_g$ may be received from a generator at a drive voltage $V_g$, with motional current $I_m$ flowing through the first branch and current $I_g-I_m$ flowing through the capacitive branch. Control of the electromechanical properties of the ultrasonic transducer may be achieved by suitably controlling $I_g$ and $V_g$. As explained above, conventional generator architectures may include a tuning inductor $L_t$ (shown in phantom in FIG. 4) for tuning out in a parallel resonance circuit the static capacitance Co at a resonant frequency so that substantially all of generator's current output $I_g$ flows through the motional branch. In this way, control of the motional branch current $I_g$ is achieved by controlling the generator current output $I_g$. The tuning inductor $L_t$ is specific to the static capacitance $C_o$ of an ultrasonic transducer, however, and a different ultrasonic transducer having a different static capacitance requires a different tuning inductor $L_t$. Moreover, because the tuning inductor $L_t$ is matched to the nominal value of the static capacitance Co at a resonant frequency, accurate control of the motional branch current $I_m$ is assured only at that frequency, and as frequency shifts down with transducer temperature, accurate control of the motional branch current is compromised.

Forms of the generator 102 shown in FIGS. 1-3 do not rely on a tuning inductor $L_t$ to monitor the motional branch current $I_m$. Instead, the generator 102 may use the measured value of the static capacitance $C_o$ in between applications of power for a specific ultrasonic surgical instrument 104 (along with drive signal voltage and current feedback data) to determine values of the motional branch current $I_m$ on a dynamic and ongoing basis (e.g., in real-time). Such forms of the generator 102 are therefore able to provide virtual tuning to simulate a system that is tuned or resonant with any value of static capacitance $C_o$ at any frequency, and not just at the resonant frequency dictated by a nominal value of the static capacitance $C_o$.

Figure 5:
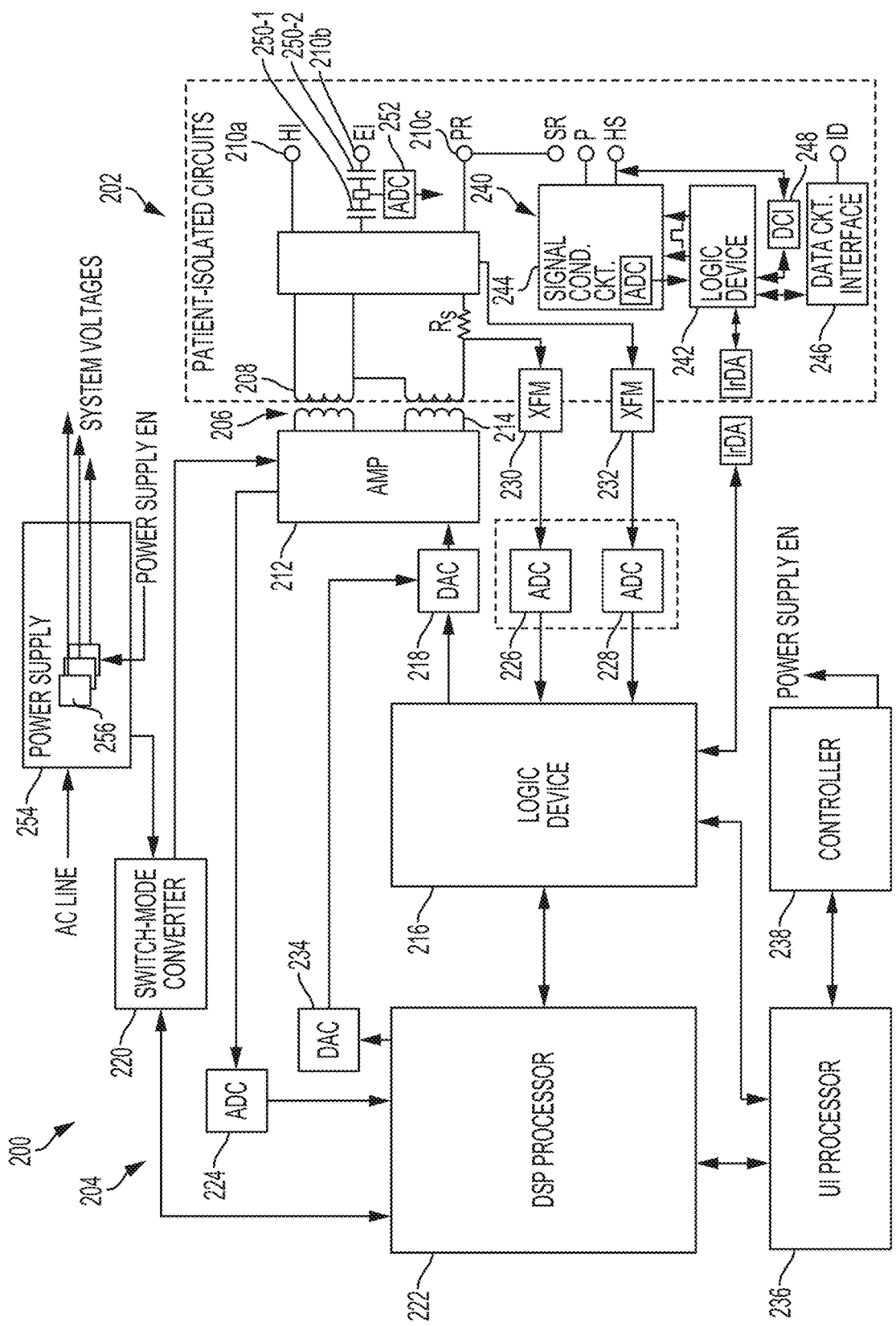
FIG. 5 is a structural view of one aspect of a generator architecture.

FIG. 5 is a simplified block diagram of a generator 200 which is one form of the generator 102 shown in FIGS. 1-3 for proving inductorless tuning as described herein, among other benefits. Additional details of the generator 102 are described in commonly assigned and contemporaneously filed U.S. patent application Ser. No. 12/896,360, titled "Surgical Generator For Ultrasonic And Electrosurgical Devices,", now U.S. Pat. No. 9,060,775, the disclosure of which is incorporated herein by reference in its entirety. With reference to FIG. 5, the generator 200 may comprise a patient isolated stage 202 in communication with a non-isolated stage 204 via a power transformer 206. A secondary winding 208 of the power transformer 206 is contained in the isolated stage 202 and may comprise a tapped configuration (e.g., a center-tapped or a non-center-tapped configuration) to define drive signal outputs 210a, 210b, 210c for outputting drive signals to different surgical devices, such as, for example, an ultrasonic surgical instrument 104 and an electrosurgical instrument 106 (as shown in FIGS. 1-3). In particular, the drive signal outputs 210a, 210c may output an ultrasonic drive signal (e.g., a 420V RMS drive signal) to an ultrasonic surgical instrument 104, and the drive signal outputs 210b, 210c may output an electrosurgical RF drive signal (e.g., a 100V RMS drive signal) to an electrosurgical instrument 106, with the output 210b corresponding to the center tap of the power transformer 206.

In certain forms, the ultrasonic and electrosurgical drive signals may be provided simultaneously to distinct surgical instruments and/or to a single surgical instrument having the capability to deliver both ultrasonic and electrosurgical energy to tissue, such as multifunction surgical instrument 108 (FIGS. 1 and 3). It will be appreciated that the electrosurgical signal, provided either to a dedicated electrosurgical instrument and/or to a combined multifunction ultrasonic/electrosurgical instrument may be either a therapeutic or sub-therapeutic level signal. For example, the ultrasonic and radio frequency signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue while the electrosurgical RF energy may be employed for vessel sealing.

The non-isolated stage 204 may comprise a power amplifier 212 having an output connected to a primary winding 214 of the power transformer 206. In certain forms the power amplifier 212 may be comprise a push-pull amplifier. For example, the non-isolated stage 204 may further comprise a logic device 216 for supplying a digital output to a digital-to-analog converter (DAC) 218, which in turn supplies a corresponding analog signal to an input of the power amplifier 212. In certain forms the logic device 216 may comprise a programmable gate array (PGA), a field-programmable gate array (FPGA), programmable logic device (PLD), among other logic circuits, for example. The logic device 216, by virtue of controlling the input of the power amplifier 212 via the DAC 218, may therefore control any of a number of parameters (e.g., frequency, waveform shape, waveform amplitude) of drive signals appearing at the drive signal outputs 210a, 210b, 210c. In certain forms and as discussed below, the logic device 216, in conjunction with a processor (e.g., a digital signal processor discussed below), may implement a number of digital signal processing (DSP)-based and/or other control techniques to control parameters of the drive signals output by the generator 200.

Power may be supplied to a power rail of the power amplifier 212 by a switch-mode regulator 220. In certain forms the switch-mode regulator 220 may comprise an adjustable buck regulator, for example. The non-isolated stage 204 may further comprise a first processor such as DSP processor 222, which in one form may comprise a DSP processor such as an Analog Devices ADSP-21469 SHARC DSP, available from Analog Devices, Norwood, Mass., for example, although in various forms any suitable processor may be employed. In certain forms the DSP processor 222 may control operation of the switch-mode power converter 220 responsive to voltage feedback data received from the power amplifier 212 by the DSP processor 222 via an analog-to-digital converter (ADC) 224. In one form, for example, the DSP processor 222 may receive as input, via the ADC 224, the waveform envelope of a signal (e.g., an RF signal) being amplified by the power amplifier 212. The DSP processor 222 may then control the switch-mode regulator 220 (e.g., via a pulse-width modulated (PWM) output) such that the rail voltage supplied to the power amplifier 212 tracks the waveform envelope of the amplified signal. By dynamically modulating the rail voltage of the power amplifier 212 based on the waveform envelope, the efficiency of the power amplifier 212 may be significantly improved relative to a fixed rail voltage amplifier schemes.

In certain forms, the logic device 216, in conjunction with the DSP processor 222, may implement a direct digital synthesizer (DDS) control scheme to control the waveform shape, frequency and/or amplitude of drive signals output by the generator 200. In one form, for example, the logic device 216 may implement a DDS control technique by recalling waveform samples stored in a dynamically-updated look-up table (LUT), such as a RAM LUT, which may be embedded in an FPGA. This control technique is particularly useful for ultrasonic applications in which an ultrasonic transducer, such as the ultrasonic transducer 120 (FIGS. 1-3), may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 200 is impacted by various sources of distortion present in the output drive circuit (e.g., the power transformer 206, the power amplifier 212), voltage and current feedback data based on the drive signal may be input into a technique, such as an error control technique implemented by the DSP processor 222, which compensates for distortion by suitably pre-distorting or modifying the waveform samples stored in the LUT on a dynamic, ongoing basis (e.g., in real-time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 204 may further comprise an ADC 226 and an ADC 228 coupled to the output of the power transformer 206 via respective isolation transformers 230, 232 for respectively sampling the voltage and current of drive signals output by the generator 200. In certain forms, the ADCs 226, 228 may be configured to sample at high speeds (e.g., 80 MSPS) to enable oversampling of the drive signals. In one form, for example, the sampling speed of the ADCs 226, 228 may enable approximately 200× (depending on frequency) oversampling of the drive signals. In certain forms, the sampling operations of the ADC 226, 228 may be performed by a singe ADC receiving input voltage and current signals via a two-way multiplexer. The use of high-speed sampling in forms of the generator 200 may enable, among other things, calculation of the complex current flowing through the motional branch (which may be used in certain forms to implement DDS-based waveform shape control described herein), accurate digital filtering of the sampled signals, and calculation of real power consumption with a high degree of precision. Voltage and current feedback data output by the ADCs 226, 228 may be received and processed (e.g., FIFO buffering, multiplexing) by the logic device 216 and stored in data memory for subsequent retrieval by, for example, the DSP processor 222. As noted above, voltage and current feedback data may be used as input to a technique for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 216 when the voltage and current feedback data pair was acquired. Synchronization of the LUT samples and the voltage and current feedback data in this manner contributes to the correct timing and stability of the pre-distortion technique.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of ultrasonic distortion and correspondingly enhancing impedance phase measurement accuracy. The determination of phase impedance and a frequency control signal may be implemented in the DSP processor 222, for example, with the frequency control signal being supplied as input to a DDS control technique implemented by the logic device 216.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control technique, such as, for example, a PID control technique, in the DSP processor 222. Variables controlled by the control technique to suitably control the current amplitude of the drive signal may include, for example, the scaling of the LUT waveform samples stored in the logic device 216 and/or the full-scale output voltage of the DAC 218 (which supplies the input to the power amplifier 212) via a DAC 234.

The non-isolated stage 204 may further comprise a second processor such as UI processor 236 for providing, among other things user interface (UI) functionality. In one form, the UI processor 236 may comprise an Atmel AT91SAM9263 processor having an ARM 926EJ-S core, available from Atmel Corporation, San Jose, Calif., for example. Examples of UI functionality supported by the UI processor 236 may include audible and visual user feedback, communication with peripheral devices (e.g., via a Universal Serial Bus (USB) interface), communication with the foot switch 130, communication with an input device 118 (e.g., a touch screen display) and communication with an output device 112 (e.g., a speaker), as shown in FIG. 3, for example. The UI processor 236 may communicate with the DSP processor 222 and the logic device 216 (e.g., via serial peripheral interface (SPI) buses). Although the UI processor 236 may primarily support UI functionality, it also may coordinate with the DSP processor 222 to implement hazard mitigation in certain forms. For example, the UI processor 236 may be programmed to monitor various aspects of user input and/or other inputs (e.g., touch screen inputs, foot switch 130 inputs (FIG. 3), temperature sensor inputs) and may disable the drive output of the generator 200 when an erroneous condition is detected.

In certain forms, both the DSP processor 222 and the UI processor 236, for example, may determine and monitor the operating state of the generator 200. For the DSP processor 222, the operating state of the generator 200 may dictate, for example, which control and/or diagnostic processes are implemented by the DSP processor 222. For the UI processor 236, the operating state of the generator 200 may dictate, for example, which elements of a user interface (e.g., display screens, sounds) are presented to a user. The respective DSP and UI processors 222, 236 may independently maintain the current operating state of the generator 200 and recognize and evaluate possible transitions out of the current operating state. The DSP processor 222 may function as the master in this relationship and determine when transitions between operating states are to occur. The UI processor 236 may be aware of valid transitions between operating states and may confirm if a particular transition is appropriate. For example, when the DSP processor 222 instructs the UI processor 236 to transition to a specific state, the UI processor 236 may verify that requested transition is valid. In the event that a requested transition between states is determined to be invalid by the UI processor 236, the UI processor 236 may cause the generator 200 to enter a failure mode.

The non-isolated stage 204 may further comprise a controller 238 for monitoring input devices 110 (e.g., a capacitive touch sensor used for turning the generator 200 on and off, a capacitive touch screen, e.g., as shown in FIGS. 1 and 3). In certain forms, the controller 238 may comprise at least one processor and/or other controller device in communication with the UI processor 236. In one form, for example, the controller 238 may comprise a processor (e.g., a Mega168 8-bit controller available from Atmel) configured to monitor user input provided via one or more capacitive touch sensors. In one form, the controller 238 may comprise a touch screen controller (e.g., a QT5480 touch screen controller available from Atmel) to control and manage the acquisition of touch data from a capacitive touch screen.

In certain forms, when the generator 200 is in a "power off" state, the controller 238 may continue to receive operating power (e.g., via a line from a power supply of the generator 200. In this way, the controller 238 may continue to monitor an input device 110 (e.g., a capacitive touch sensor located on a front panel of the generator 200) for turning the generator 200 on and off. When the generator 200 is in the power off state, the controller 238 may wake the power supply (e.g., enable operation of one or more DC/DC voltage converters of the power supply) if activation of the "on/off" input device 110 by a user is detected. The controller 238 may therefore initiate a sequence for transitioning the generator 200 to a "power on" state. Conversely, the controller 238 may initiate a sequence for transitioning the generator 200 to the power off state if activation of the "on/off" input device 110 is detected when the generator 200 is in the power on state. In certain forms, for example, the controller 238 may report activation of the "on/off" input device 110 to the UI processor 236, which in turn implements the necessary process sequence for transitioning the generator 200 to the power off state. In such forms, the controller 238 may have no independent ability for causing the removal of power from the generator 200 after its power on state has been established.

In certain forms, the controller 238 may cause the generator 200 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 202 may comprise an instrument interface circuit 240 to, for example, provide a communication interface between a control circuit of a surgical device (e.g., a control circuit comprising hand piece switches) and components of the non-isolated stage 204, such as, for example, the programmable logic device 216, the DSP processor 222 and/or the UI processor 236. The instrument interface circuit 240 may exchange information with components of the non-isolated stage 204 via a communication link that maintains a suitable degree of electrical isolation between the stages 202, 204, such as, for example, an infrared (IR)-based communication link. Power may be supplied to the instrument interface circuit 240 using, for example, a low-dropout voltage regulator powered by an isolation transformer driven from the non-isolated stage 204.

In one form, the instrument interface circuit 240 may comprise a logic device 242 (e.g., logic circuit, programmable logic circuit, PGA, FPGA, PLD) in communication with a signal conditioning circuit 242. The signal conditioning circuit 244 may be configured to receive a periodic signal from the logic circuit 242 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical device control circuit (e.g., by using a conductive pair in a cable that connects the generator 200 to the surgical device) and monitored to determine a state or configuration of the control circuit. The control circuit may comprise a number of switches, resistors and/or diodes to modify one or more characteristics (e.g., amplitude, rectification) of the interrogation signal such that a state or configuration of the control circuit is uniquely discernable based on the one or more characteristics. In one form, for example, the signal conditioning circuit 244 may comprises an ADC for generating samples of a voltage signal appearing across inputs of the control circuit resulting from passage of interrogation signal therethrough. The logic device 242 (or a component of the non-isolated stage 204) may then determine the state or configuration of the control circuit based on the ADC samples.

In one form, the instrument interface circuit 240 may comprise a first data circuit interface 246 to enable information exchange between the logic circuit 242 (or other element of the instrument interface circuit 240) and a first data circuit disposed in or otherwise associated with a surgical device. In certain forms, for example, a first data circuit 136 (FIG. 2) may be disposed in a cable integrally attached to a surgical device hand piece, or in an adaptor for interfacing a specific surgical device type or model with the generator 200. The first data circuit 136 may be implemented in any suitable manner and may communicate with the generator according to any suitable protocol including, for example, as described herein with respect to the first circuit 136. In certain forms, the first data circuit may comprise a non-volatile storage device, such as an electrically erasable programmable read-only memory (EEPROM) device. In certain forms and referring again to FIG. 5, the first data circuit interface 246 may be implemented separately from the logic device 242 and comprise suitable circuitry (e.g., discrete logic devices, a processor) to enable communication between the programmable logic device 242 and the first data circuit. In other forms, the first data circuit interface 246 may be integral with the logic device 242.

In certain forms, the first data circuit 136 (FIG. 2) may store information pertaining to the particular surgical device with which it is associated. Such information may include, for example, a model number, a serial number, a number of operations in which the surgical device has been used, and/or any other type of information. This information may be read by the instrument interface circuit 1098 (e.g., by the logic device 242), transferred to a component of the non-isolated stage 204 (e.g., to logic device 216, DSP processor 222 and/or UI processor 236) for presentation to a user via an output device 112 (FIGS. 1 and 3) and/or for controlling a function or operation of the generator 200. Additionally, any type of information may be communicated to first data circuit 136 for storage therein via the first data circuit interface 246 (e.g., using the logic device 242). Such information may comprise, for example, an updated number of operations in which the surgical device has been used and/or dates and/or times of its usage.

As discussed previously, a surgical instrument may be detachable from a hand piece (e.g., as shown in FIGS. 1 and 2, the transducer 120 and the shaft 126 is detachable from the handpiece 105 of the ultrasonic surgical instrument 104) to promote instrument interchangeability and/or disposability. In such cases, conventional generators may be limited in their ability to recognize particular instrument configurations being used and to optimize control and diagnostic processes accordingly. The addition of readable data circuits to surgical device instruments to address this issue is problematic from a compatibility standpoint, however. For example, designing a surgical device to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical devices with current generator platforms.

With reference to FIGS. 1-3 and 5, additionally, forms of the generator 200 may enable communication with instrument-based data circuits. For example, the generator 200 may be configured to communicate with a second data circuit 138 contained in the ultrasonic surgical instrument 104 (e.g., and/or the other surgical instruments 106, 108). In some forms, the second data circuit 138 may be implemented in a many similar to that of the first data circuit 136 described herein. The instrument interface circuit 240 may comprise a second data circuit interface 248 to enable this communication. In one form, the second data circuit interface 248 may comprise a tri-state digital interface, although other interfaces also may be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information. In some forms, the second data circuit 138 may store information about the electrical and/or ultrasonic properties of an associated transducer 120, end effector 122, or ultrasonic drive system. For example, the first data circuit 136 may indicate a burn-in frequency slope, as described herein. Additionally or alternatively, any type of information may be communicated to second data circuit for storage therein via the second data circuit interface 248 (e.g., using the logic device 242). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 200 and provide an indication to a user (e.g., an LED indication or other visible indication) based on the received data.

In certain forms, the second data circuit and the second data circuit interface 248 may be configured such that communication between the logic device 242 and the second data circuit can be effected without the need to provide additional conductors for this purpose (e.g., dedicated conductors of a cable connecting a hand piece to the generator 200). In one form, for example, information may be communicated to and from the second data circuit using a 1-wire bus communication scheme implemented on existing cabling, such as one of the conductors used transmit interrogation signals from the signal conditioning circuit 244 to a control circuit in a hand piece. In this way, design changes or modifications to the surgical device that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical device instrument.

In certain forms, the isolated stage 202 may comprise at least one blocking capacitor 250-1 connected to the drive signal output 210*b* to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 250-2 may be provided in series with the blocking capacitor 250-1, with current leakage from a point between the blocking capacitors 250-1, 250-2 being monitored by, for example, an ADC 252 for sampling a voltage induced by leakage current. The samples may be received by the logic device 242, for example. Based changes in the leakage current (as indicated by the voltage samples in the form of FIG. 5), the generator 200 may determine when at least one of the blocking capacitors 250-1, 250-2 has failed. Accordingly, the form of FIG. 5 provides a benefit over single-capacitor designs having a single point of failure.

In certain forms, the non-isolated stage 204 may comprise a power supply 254 for outputting DC power at a suitable voltage and current. The power supply may comprise, for example, a 400 W power supply for outputting a 48 VDC system voltage. The power supply 254 may further comprise one or more DC/DC voltage converters 256 for receiving the output of the power supply to generate DC outputs at the voltages and currents required by the various components of the generator 200. As discussed above in connection with the controller 238, one or more of the DC/DC voltage converters 256 may receive an input from the controller 238 when activation of the "on/off" input device 110 (FIG. 3) by a user is detected by the controller 238 to enable operation of, or wake, the DC/DC voltage converters 256.

With reference back to FIG. 1, having described operational details of various forms of the surgical system 100 operations for the above surgical system 100 may be further described generally in terms of a process for cutting and coagulating tissue employing a surgical instrument comprising an input device 110 and the generator 102. Although a particular process is described in connection with the operational details, it can be appreciated that the process merely provides an example of how the general functionality described herein can be implemented by the surgical system 100. Further, the given process does not necessarily have to be executed in the order presented herein unless otherwise indicated. As previously discussed, the input devices 110 may be employed to program the output (e.g., impedance, current, voltage, frequency) of the surgical instruments 104, 106, 108.

Figure 6:
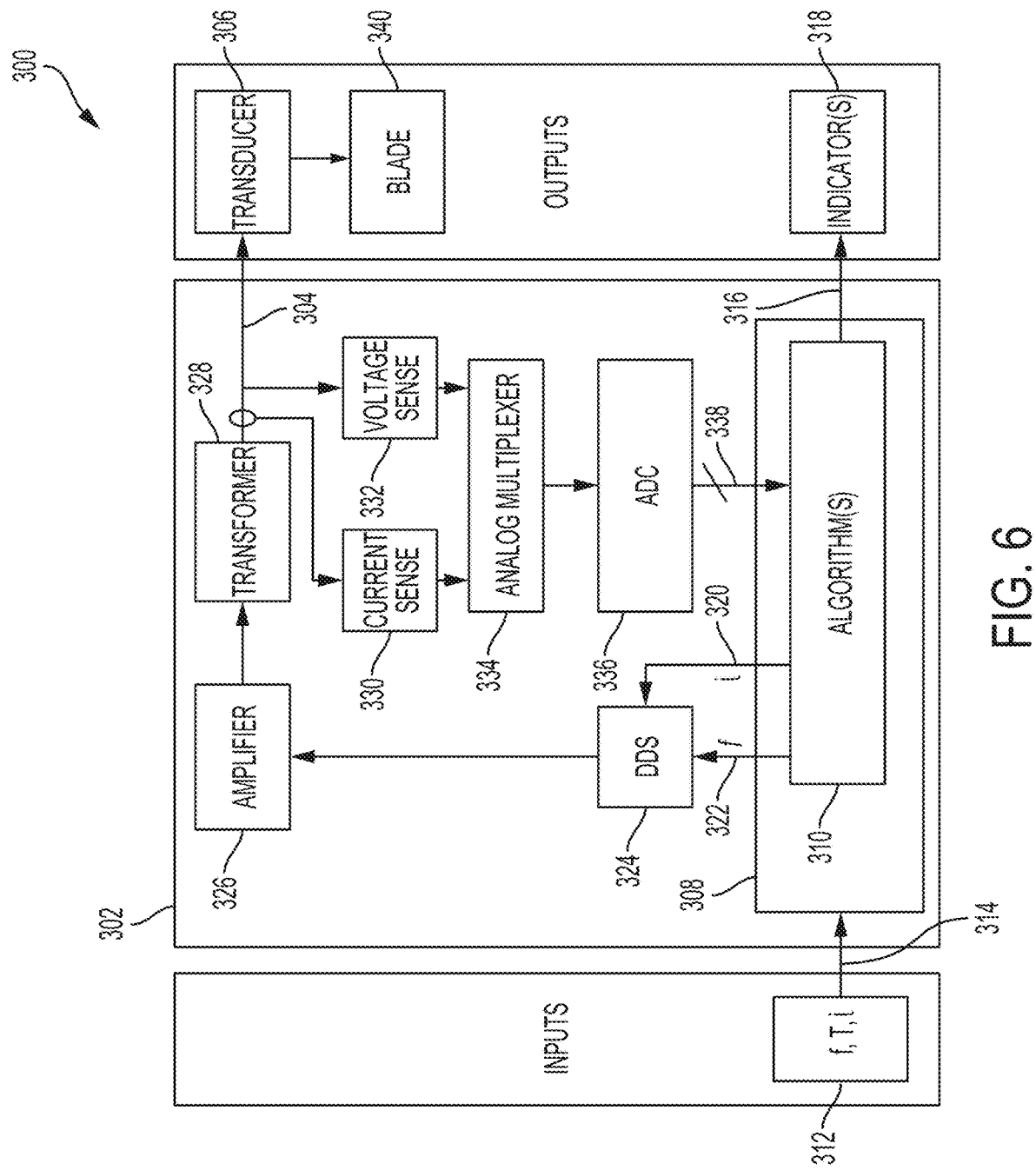
FIG. 6 illustrates one aspect of a drive system of a generator, which creates the ultrasonic electrical signal for driving an ultrasonic transducer.

FIG. 6 illustrates a generator 300 comprising one form of drive system 302, according to one aspect of the present disclosure. The generator 300 is similar to the generators 102, 200 described in connection with in FIGS. 1 and 5. The generator 300 produces an ultrasonic electrical signal for driving an ultrasonic transducer, also referred to as a drive signal. The drive system 302 is flexible and can create an ultrasonic electrical output drive signal 304 at a desired frequency and power level setting for driving an ultrasonic transducer 306. In various forms, the generator 300 may comprise several separate functional elements, such as modules, circuits, and/or blocks. Although certain modules, circuits, and/or blocks may be described by way of example, it can be appreciated that a greater or lesser number of modules, circuits, and/or blocks may be used and still fall within the scope of the forms. Further, although various forms may be described in terms of modules, circuits, and/or blocks to facilitate description, such modules, circuits, and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In one form, the drive system 302 of the generator 300 may comprise one or more embedded applications implemented as firmware, software, hardware, or any combination thereof. The drive system 302 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one form, the drive system 302 comprises a hardware component implemented as a processor 308 for executing program instructions for monitoring various measurable characteristics of the ultrasonic surgical instrument 104 (FIG. 1) and generating various functions as an output signal for driving the ultrasonic transducer 306 in cutting and/or coagulation operating modes. It will be appreciated by those skilled in the art that the generator 300 and the drive system 302 may comprise additional or fewer components and only a simplified version of the generator 300 and the drive system 302 are described herein for conciseness and clarity. In various forms, as previously discussed, the hardware component may be implemented as a DSP, PLD, ASIC, circuits, and/or registers. In one form, the processor 308 may be configured to store and execute computer software program instructions to generate the output signal functions for driving various components of the ultrasonic surgical instrument 104 (FIG. 1), such as an ultrasonic transducer 306, an end effector, and/or a blade 340.

In one form, under control of one or more software program routines, the processor 308 executes the methods in accordance with the described forms to generate a function formed by a stepwise waveform of drive signals comprising current (I), voltage (V), and/or frequency (f) for various time intervals or periods (T). The stepwise waveforms of the drive signals may be generated by forming a piecewise linear combination of constant functions over a plurality of time intervals created by varying the generator 300 drive signals, e.g., output drive current (I), voltage (V), and/or frequency (f). The time intervals or periods (T) may be predetermined (e.g., fixed and/or programmed by the user) or may be variable. Variable time intervals may be defined by setting the drive signal to a first value and maintaining the drive signal at that value until a change is detected in a monitored characteristic. Examples of monitored characteristics may comprise, for example, transducer impedance, tissue impedance, tissue heating, tissue transection, tissue coagulation, and the like. The ultrasonic drive signals generated by the generator 300 include, without limitation, ultrasonic drive signals capable of exciting the ultrasonic transducer 306 in various vibratory modes such as, for example, the primary longitudinal mode and harmonics thereof as well flexural and torsional vibratory modes.

In one form, the executable modules comprise one or more technique(s) 310 stored in memory that when executed causes the processor 308 to generate a function formed by a stepwise waveform of drive signals comprising current (I), voltage (V), and/or frequency (f) for various time intervals or periods (T). The stepwise waveforms of the drive signals may be generated by forming a piecewise linear combination of constant functions over two or more time intervals created by varying the generator 300 output drive current (I), voltage (V), and/or frequency (f). The drive signals may be generated either for predetermined fixed time intervals or periods (T) of time or variable time intervals or periods of time in accordance with the one or more technique(s) 310. Under control of the processor 308, the generator 300 varies (e.g., increment or decrement over time) the current (I), voltage (V), and/or frequency (f) up or down at a particular resolution for a predetermined period (T) or until a predetermined condition is detected, such as a change in a monitored characteristic (e.g., transducer impedance, tissue impedance). The steps can change in programmed increments or decrements. If other steps are desired, the generator 300 can increase or decrease the step adaptively based on measured system characteristics.

In operation, the user can program the operation of the generator 300 using the input device 312 located on the front panel of the generator 300 console. The input device 312 may comprise any suitable device that generates signals 314 that can be applied to the processor 308 to control the operation of the generator 300. In various forms, the input device 312 includes buttons, switches, thumbwheels, keyboard, keypad, touch screen monitor, pointing device, remote connection to a general purpose or dedicated computer. In other forms, the input device 312 may comprise a suitable user interface. Accordingly, by way of the input device 312, the user can set or program the current (I), voltage (V), frequency (f), and/or period (T) for programming the output function of the generator 300. The processor 308 then displays the selected power level by sending a signal on line 316 to an output indicator 318.

In various forms, the output indicator 318 may provide visual, audible, and/or tactile feedback to the surgeon to indicate the status of a surgical procedure, such as, for example, when tissue cutting and coagulating is complete based on a measured characteristic of the ultrasonic surgical instrument 104 (FIG. 1), e.g., transducer impedance, tissue impedance, or other measurements as subsequently described. By way of example, and not limitation, visual feedback comprises any type of visual indication device including incandescent lamps or light emitting diodes (LEDs), graphical user interface, display, analog indicator, digital indicator, bar graph display, digital alphanumeric display. By way of example, and not limitation, audible feedback comprises any type of buzzer, computer generated tone, computerized speech, voice user interface (VUI) to interact with computers through a voice/speech platform. By way of example, and not limitation, tactile feedback comprises any type of vibratory feedback provided through an instrument housing handle assembly.

In one form, the processor 308 may be configured or programmed to generate a digital current drive signal 320 and a digital frequency signal 322. These drive signals 320, 322 are applied to a direct digital synthesizer (DDS) circuit 324 to adjust the amplitude and the frequency (f) of the output drive signal 304 to the ultrasonic transducer 306. The output of the DDS circuit 324 is applied to an amplifier 326 whose output is applied to a transformer 328. The output of the transformer 328 is the output drive signal 304 applied to the ultrasonic transducer 306, which is coupled to the blade 340 by way of a waveguide.

In one form, the generator 300 comprises one or more measurement modules or components that may be configured to monitor measurable characteristics of the ultrasonic surgical instrument 104 (FIG. 1). In the illustrated form, the processor 308 may be employed to monitor and calculate system characteristics. As shown, the processor 308 measures the impedance Z of the ultrasonic transducer 306 by monitoring the current supplied to the transducer 306 and the voltage applied to the ultrasonic transducer 306. In one form, a current sense circuit 330 is employed to sense the current supplied to the ultrasonic transducer 306 and a voltage sense circuit 332 is employed to sense the output voltage applied to the ultrasonic transducer 306. These signals may be applied to the analog-to-digital converter 336 (ADC) via an analog multiplexer 334 circuit or switching circuit arrangement. The analog multiplexer 334 routes the appropriate analog signal to the ADC 336 for conversion. In other forms, multiple ADCs 336 may be employed for each measured characteristic instead of the multiplexer 334 circuit. The processor 308 receives the digital output 338 of the ADC 336 and calculates the transducer impedance Z based on the measured values of current and voltage. The processor 308 adjusts the output drive signal 304 such that it can generate a desired power versus load curve. In accordance with programmed techniques 310, the processor 308 can vary the drive signal 320, e.g., the current or frequency, in any suitable increment or decrement in response to the transducer impedance Z.

Having described operational details of various forms of the surgical system 100 shown in FIG. 1, operations for the above surgical system 100 may be further described in terms of a process for cutting and coagulating a blood vessel employing a surgical instrument comprising the input device 110 and the transducer impedance measurement capabilities of the drive system 302 described with reference to FIG. 6. Although a particular process is described in connection with the operational details, it can be appreciated that the process merely provides an example of how the general functionality described herein can be implemented by the surgical system 100. Further, the given process does not necessarily have to be executed in the order presented herein unless otherwise indicated.

Figure 7:
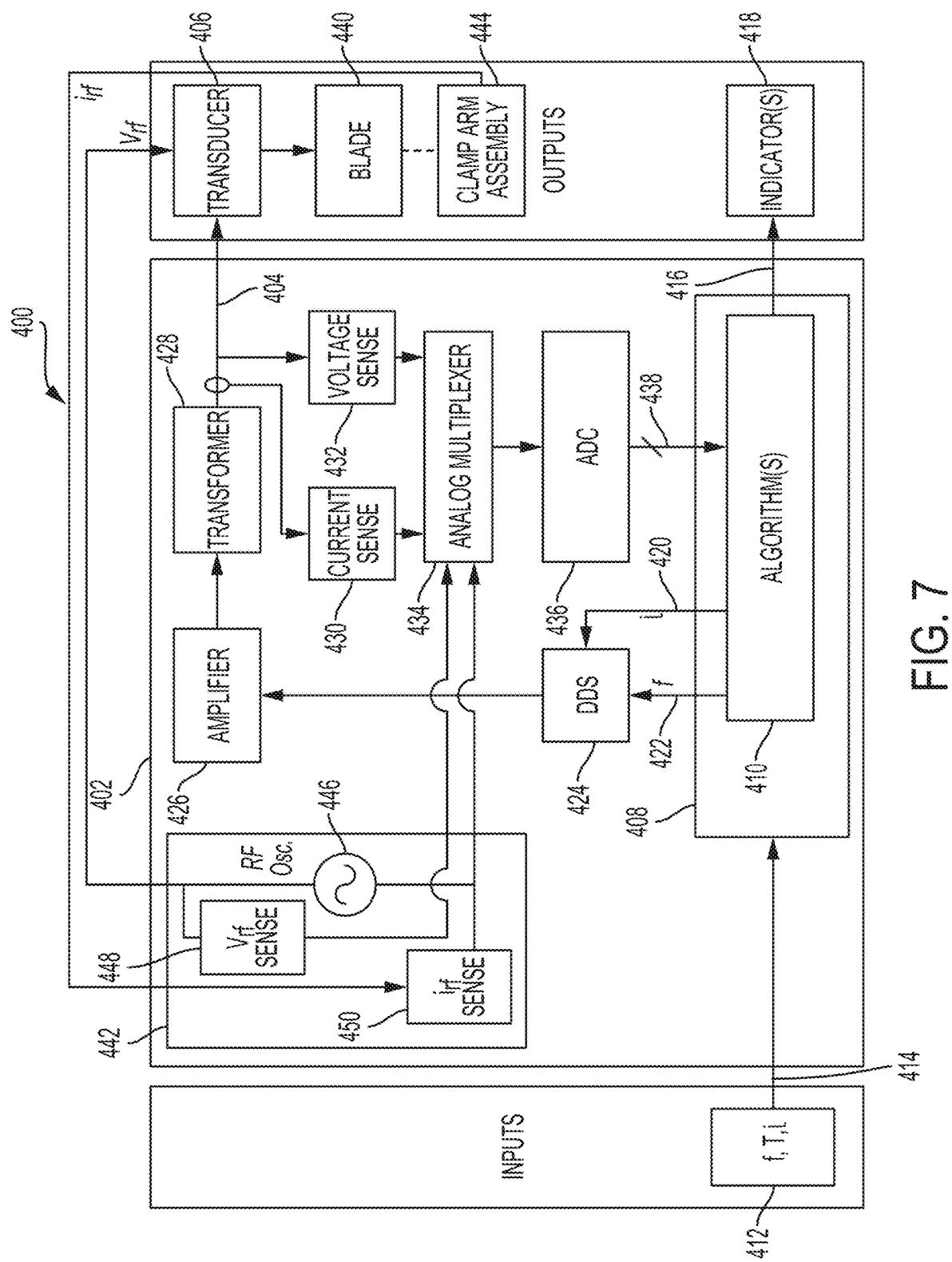
FIG. 7 illustrates one aspect of a drive system of a generator comprising a tissue impedance module.

FIG. 7 illustrates one aspect of a drive system of a generator 400 comprising a tissue impedance module 442. The drive system 402 generates the ultrasonic electrical drive signal 404 to drive the ultrasonic transducer 406. In one aspect, the tissue impedance module 442 may be configured to measure the impedance Zt of tissue grasped between the blade 440 and the clamp arm assembly 444. The tissue impedance module 442 comprises an RF oscillator 446, a voltage sensing circuit 448, and a current sensing circuit 450. The voltage and current sensing circuits 448, 450 respond to the RF voltage Vrf applied to the blade 440 electrode and the RF current Irf flowing through the blade 440 electrode, the tissue, and the conductive portion of the clamp arm assembly 444. The sensed current Irf and the sensed voltage Vrf from the current sense circuit 430 and the voltage sense circuit 432 are converted to digital form by the ADC 436 via the analog multiplexer 434. The processor 408 receives the digitized output 438 of the ADC 436 and determines the tissue impedance Zt by calculating the ratio of the RF voltage Vrf to current Irf measured by the voltage sensing circuit 448 and the current sense circuit 450.

In one form, the processor 408 may be configured or programmed to generate a digital current signal 420 and a digital frequency signal 422. These signals 420, 422 are applied to a direct digital synthesizer (DDS) circuit 424 to adjust the amplitude and the frequency (f) of the current output signal 404 to the transducer 406. The output of the DDS circuit 424 is applied to an amplifier 426 whose output is applied to a transformer 428. The output of the transformer 428 is the signal 404 applied to the ultrasonic transducer 406, which is coupled to the blade 440 by way of a waveguide.

In one aspect, the transection of the inner muscle layer and the tissue may be detected by sensing the tissue impedance Zt. Accordingly, detection of the tissue impedance Zt may be integrated with an automated process for separating the inner muscle layer from the outer adventitia layer prior to transecting the tissue without causing a significant amount of heating, which normally occurs at resonance.

In one form, the RF voltage Vrf applied to the blade 440 electrode and the RF current Irf flowing through the blade 440 electrode, the tissue, and the conductive portion of the clamp arm assembly 444 are suitable for vessel sealing and/or dissecting. Thus, the RF energy output of the generator 400 can be selected for non-therapeutic functions such as tissue impedance measurements as well as therapeutic functions such as vessel sealing and/or dissection. It will be appreciated, that in the context of the present disclosure, the ultrasonic and the RF electrosurgical energies can be supplied by the generator either individually or simultaneously.

In operation, the user can program the operation of the generator 400 using the input device 412 located on the front panel of the generator 400 console. The input device 412 may comprise any suitable device that generates signals 414 that can be applied to the processor 408 to control the operation of the generator 400. In various forms, the input device 412 includes buttons, switches, thumbwheels, keyboard, keypad, touch screen monitor, pointing device, remote connection to a general purpose or dedicated computer. In other forms, the input device 412 may comprise a suitable user interface. Accordingly, by way of the input device 412, the user can set or program the current (I), voltage (V), frequency (f), and/or period (T) for programming the function output of the generator 400. The processor 408 then displays the selected power level by sending a signal on line 416 to an output indicator 418.

In various forms, feedback is provided by the output indicator 418. The output indicator 418 is particularly useful in applications where the tissue being manipulated by the end effector is out of the user's field of view and the user cannot see when a change of state occurs in the tissue. The output indicator 418 communicates to the user that a change in tissue state has occurred. As previously discussed, the output indicator 418 may be configured to provide various types of feedback to the user including, without limitation, visual, audible, and/or tactile feedback to indicate to the user (e.g., surgeon, clinician) that the tissue has undergone a change of state or condition of the tissue. By way of example, and not limitation, as previously discussed, visual feedback comprises any type of visual indication device including incandescent lamps or LEDs, graphical user interface, display, analog indicator, digital indicator, bar graph display, digital alphanumeric display. By way of example, and not limitation, audible feedback comprises any type of buzzer, computer generated tone, computerized speech, VUI to interact with computers through a voice/speech platform. By way of example, and not limitation, tactile feedback comprises any type of vibratory feedback provided through the instrument housing handle assembly. The change of state of the tissue may be determined based on transducer and tissue impedance measurements as previously described, or based on voltage, current, and frequency measurements.

In one form, the various executable modules (e.g., algorithms 410) comprising computer readable instructions can be executed by the processor 408 portion of the generator 400. In various forms, the operations described with respect to the techniques may be implemented as one or more software components, e.g., programs, subroutines, logic; one or more hardware components, e.g., processors, DSPs, PLDs, ASICs, circuits, registers; and/or combinations of software and hardware. In one form, the executable instructions to perform the techniques may be stored in memory. When executed, the instructions cause the processor 408 to determine a change in tissue state provide feedback to the user by way of the output indicator 418. In accordance with such executable instructions, the processor 408 monitors and evaluates the voltage, current, and/or frequency signal samples available from the generator 400 and according to the evaluation of such signal samples determines whether a change in tissue state has occurred. As further described below, a change in tissue state may be determined based on the type of ultrasonic instrument and the power level that the instrument is energized at. In response to the feedback, the operational mode of the ultrasonic surgical instrument may be controlled by the user or may be automatically or semi-automatically controlled.

As noted above, a single output generator can deliver both RF and ultrasonic energy through a single port and these signals can be delivered separately or simultaneously to the end effector to treat tissue. A single output port generator can include a single output transformer with multiple taps to provide power, either RF or ultrasonic energy, to the end effector depending on the type of treatment of tissue being performed. For example, the generator can deliver energy with higher voltage and lower current to drive an ultrasonic transducer, with lower voltage and higher current as required to drive electrodes for sealing tissue, or with a coagulation waveform for spot coagulation using either monopolar or bipolar electrosurgical electrodes. The output waveform from the generator can be steered, switched, or filtered to provide the desired frequency to the end effector of the surgical instrument.

Figure 8:
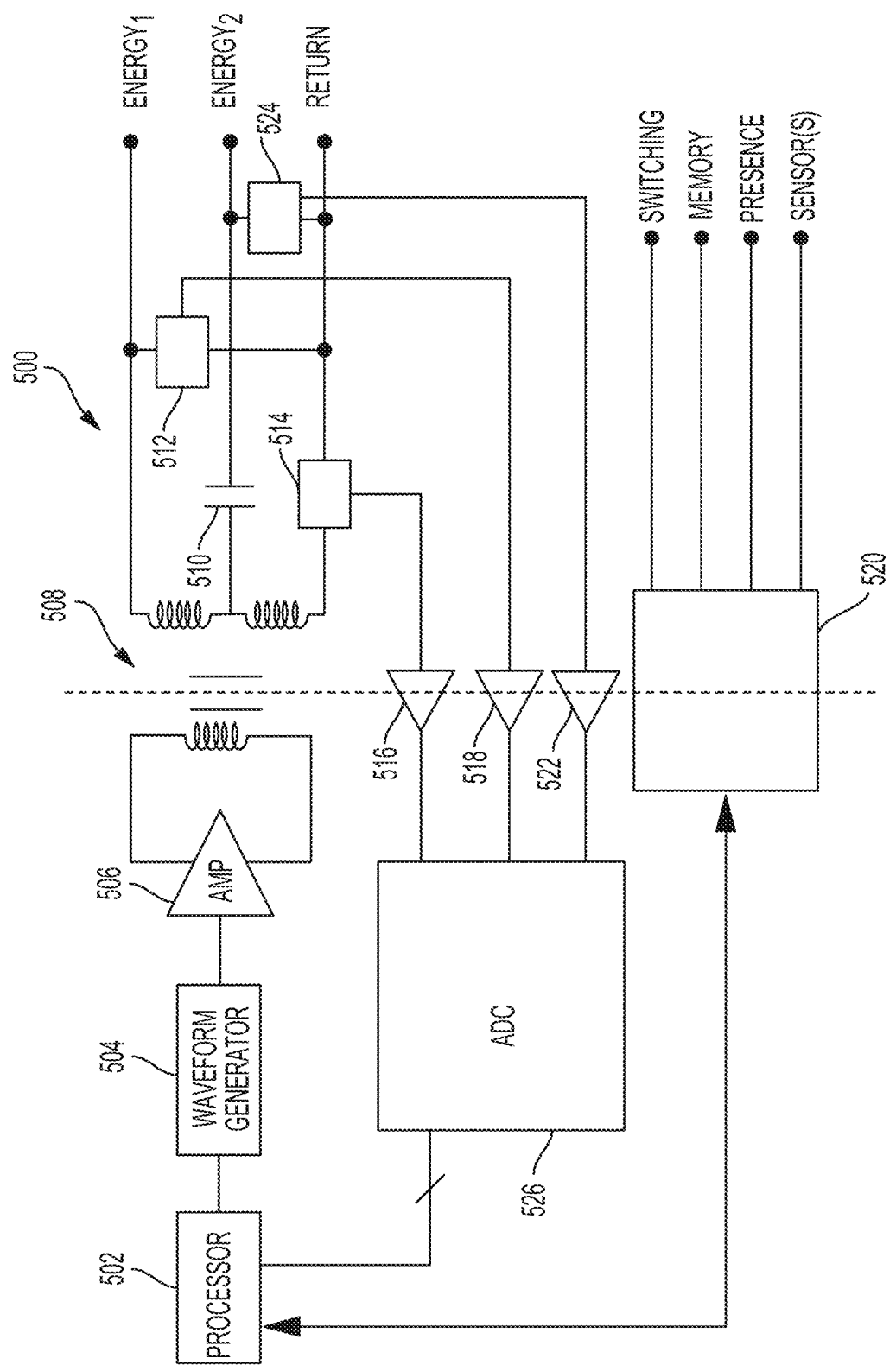
FIG. 8 illustrates one aspect of a generator for delivering multiple energy modalities to a surgical instrument.

FIG. 8 illustrates an example of a generator 500 for delivering multiple energy modalities to a surgical instrument. The generator 500 is similar to the generator 102 described in connection with FIG. 1 and includes functionalities of the generators 200, 300, 400 shown in FIGS. 5-7. For conciseness and clarity of disclosure, hereinbelow, the various logic flow diagrams are described in connection with the generator 500, which is a high level block diagram representation. Accordingly, the reader is directed to the description of the functional blocks of the generators 200, 300, 400 in FIGS. 5-7 for additional details that may be necessary to understand and practice the logic flow diagrams described hereinbelow in connection with the generator 500.

Turning back to FIG. 8, the generator 500 provides radio frequency and ultrasonic signals for delivering energy to a surgical instrument. The radio frequency and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port and these signals can be delivered separately or simultaneously to the end effector to treat tissue. The generator 500 comprises a processor 502 coupled to a waveform generator 504. The processor 502 and waveform generator 504 are configured to generate a variety of signal waveforms based on information stored in a memory coupled to the processor 502, not shown for clarity of disclosure. The digital information associated with a waveform is provided to the waveform generator 504 which includes one or more digital-to-analog (DAC) converters to convert the digital input into an analog output. The analog output is fed to an amplifier 1106 for signal conditioning and amplification. The conditioned and amplified output of the amplifier 506 is coupled to a power transformer 508. The signals are coupled across the power transformer 508 to the secondary side, which is in the patient isolation side. A first signal of a first energy modality is provided to the surgical instrument between the terminals labeled ENERGY1 and RETURN. A second signal of a second energy modality is coupled across a capacitor 510 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 512 is coupled across the terminals labeled ENERGY1 and the RETURN path to measure the output voltage therebetween. A second voltage sensing circuit 524 is coupled across the terminals labeled ENERGY2 and the RETURN path to measure the output voltage therebetween. A current sensing circuit 514 is disposed in series with the RETURN leg of the secondary side of the power transformer 508 as shown to measure the output current for either energy modality. If different return paths are provided for each energy modality, then a separate current sensing circuit should be provided in each return leg. The outputs of the first and second voltage sensing circuits 512, 524 are provided to respective isolation transformers 516, 522 and the output of the current sensing circuit 514 is provided to another isolation transformer 518. The outputs of the isolation transformers 516, 518, 522 in the on the primary side of the power transformer 508 (non-patient-isolated side) are provided to a one or more analog-to-digital converters 526 (ADC). The digitized output of the ADC 526 is provided to the processor 502 for further processing and computation. The output voltages and output current feedback information can be employed to adjust the output voltage and current provided to the surgical instrument and to compute output impedance, among other parameters. Input/output communications between the processor 502 and patient isolated circuits is provided through an interface circuit 520. Sensors also may be in electrical communication with the processor 502 by way of the interface 520.

In one aspect, the impedance may be determined by the processor 502 by dividing the output of either the first voltage sensing circuit 512 coupled across the terminals labeled ENERGY1/RETURN or the second voltage sensing circuit 524 coupled across the terminals labeled ENERGY2/RETURN by the output of the current sensing circuit 514 disposed in series with the RETURN leg of the secondary side of the power transformer 508. The outputs of the first and second voltage sensing circuits 512, 524 are provided to separate isolations transformers 516, 522 and the output of the current sensing circuit 514 is provided to another isolation transformer 516. The digitized voltage and current sensing measurements from the ADC 526 are provided the processor 502 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 8 shows a single return path RETURN may be provided for two or more energy modalities, in other aspects multiple return paths RETURNn may be provided for each energy modality ENERGYn. Thus, as described herein, the ultrasonic transducer impedance may be measured by dividing the output of the first voltage sensing circuit 512 by the current sensing circuit 514 and the tissue impedance may be measured by dividing the output of the second voltage sensing circuit 524 by the current sensing circuit 514.

As shown in FIG. 8, the generator 500 comprising at least one output port can include a power transformer 508 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 500 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 500 can be steered, switched, or filtered to provide the frequency to the end effector of the surgical instrument. The connection of an ultrasonic transducer to the generator 500 output would be preferably located between the output labeled ENERGY1 and RETURN as shown in FIG. 8. An In one example, a connection of RF bipolar electrodes to the generator 500 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Figure 9:
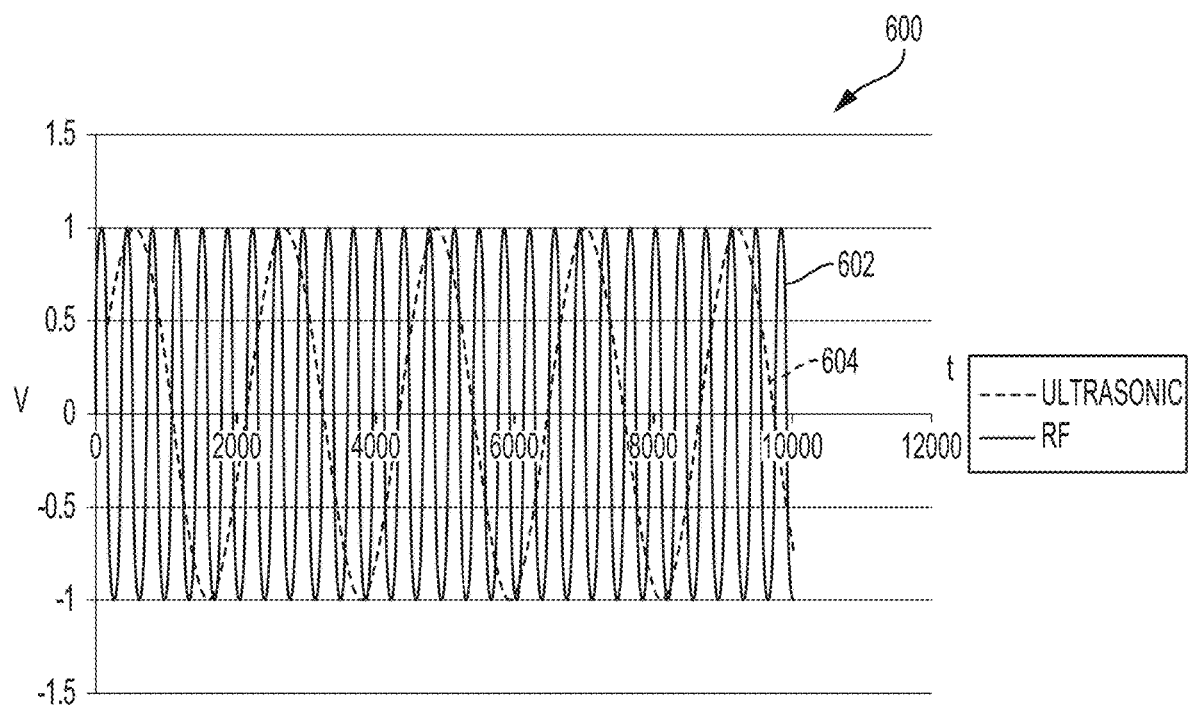
FIG. 9 is an example graph of two waveforms of energy from one aspect of a generator.

In other aspects, the generators 102, 200, 300, 400, 500 described in connection with FIGS. 1-3 and 5-8, the ultrasonic generator drive circuit 114, and/or electrosurgery/RF drive circuit 116 as described in connection with FIG. 3 may be formed integrally with any one of the surgical instruments 104, 106, 108 described in connection with FIGS. 1 and 2. Accordingly, any of the processors, digital signal processors, circuits, controllers, logic devices, ADCs, DACs, amplifiers, converters, transformers, signal conditioners, data interface circuits, current and voltage sensing circuits, direct digital synthesis circuits, multiplexer (analog or digital), waveform generators, RF generators, memory, and the like, described in connection with any one of the generators 102, 200, 300, 400, 500 can be located within the surgical instruments 104, 106, 108 or may be located remotely from the surgical instruments 104, 106, 108 and coupled to the surgical instruments via wired and/or wireless electrical connections. Examples of waveforms representing energy for delivery from a generator are illustrated in FIGS. 9-13. FIG. 9 illustrates an example graph 600 showing first and second individual waveforms representing an RF output signal 602 and an ultrasonic output signal 604 superimposed on the same time and voltage scale for comparison purposes. These output signals 602, 604 are provided at the ENERGY output of the generator 500 shown in FIG. 8. Time (t) is shown along the horizontal axis and voltage (V) is shown along the vertical axis. The RF output signal 602 has a frequency of about 330 kHz RF and a peak-to-peak voltage of ±1V. The ultrasonic output signal 604 has a frequency of about 55 kHz and a peak-to-peak voltage of ±1V. It will be appreciated that the time (t) scale along the horizontal axis and the voltage (V) scale along the vertical axis are normalized for comparison purposes and may be different actual implementations, or represent other electrical parameters such as current.

Figure 10:
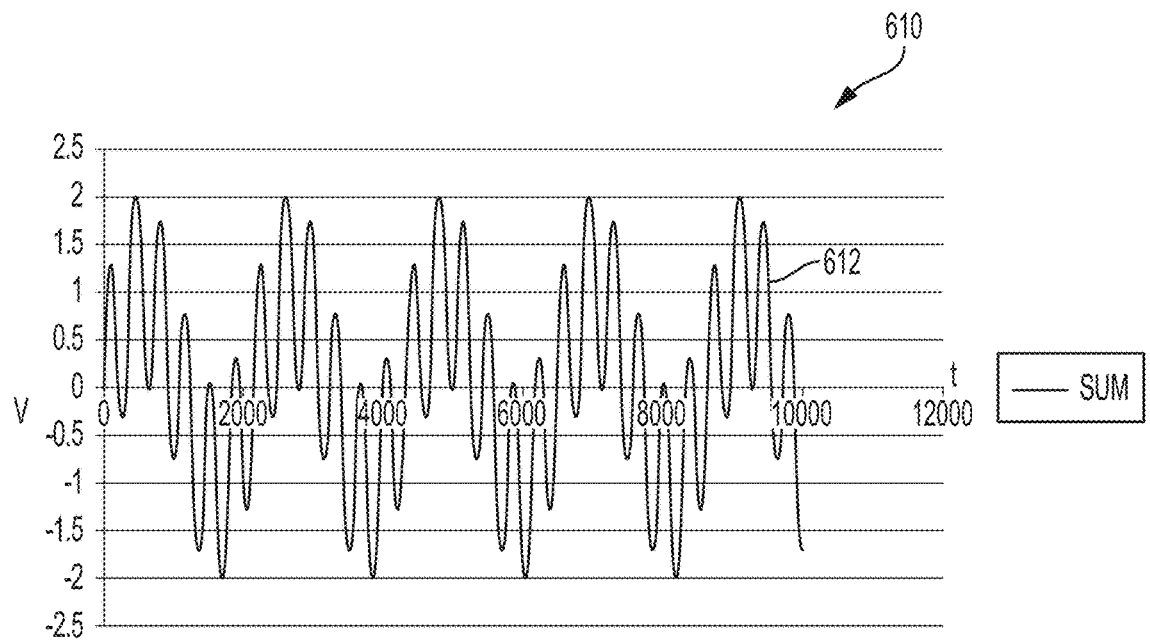
FIG. 10 is an example graph of the sum of the waveforms of FIG. 9.

FIG. 10 illustrates an example graph 610 showing the sum of the two output signals 602, 604 shown in FIG. 9. Time (t) is shown along the horizontal axis and voltage (V) is shown along the vertical axis. The sum of the RF output signal 602 and the ultrasonic output signal 604 shown in FIG. 9 produces a combined output signal 612 having a 2V peak-to-peak voltage, which is twice the amplitude of the original RF and ultrasonic signals shown (1V peak-to-peak) shown in FIG. 9. An amplitude of twice the original amplitude can cause problems with the output section of the generator, such as distortion, saturation, clipping of the output, or stresses on the output components. Thus, the management of a single combined output signal 612 that has multiple treatment components is an important aspect of the generator 500 shown in FIG. 8. There are a variety of ways to achieve this management. In one form, one of the two RF or ultrasonic output signals 602, 604 can be dependent on the peaks of the other output signal.

Figure 11:
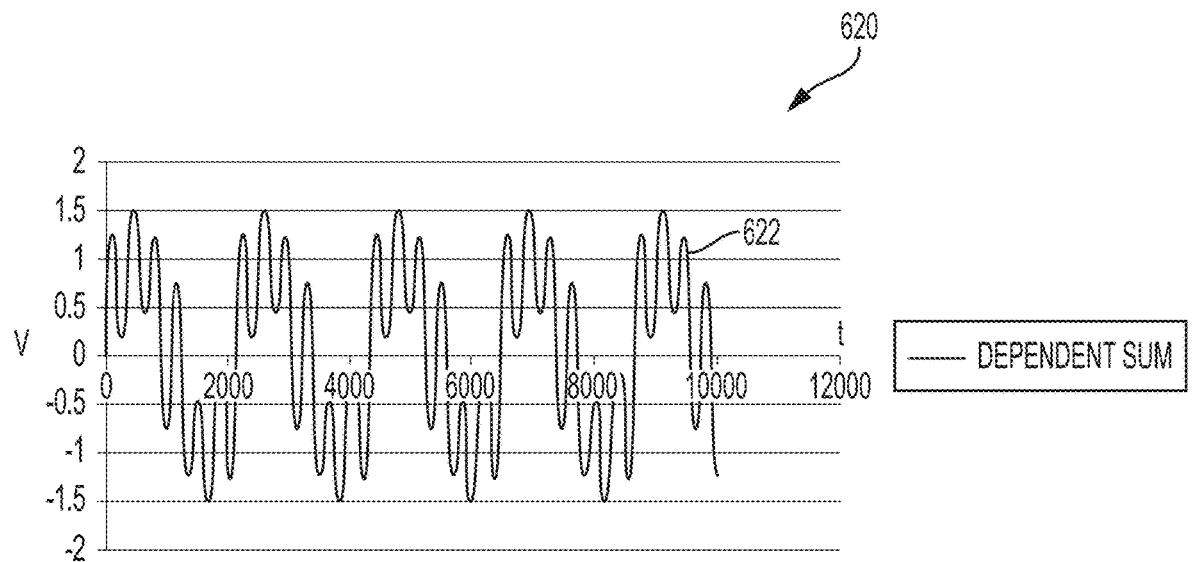
FIG. 11 is an example graph of sum of the waveforms of FIG. 9 with the RF waveform dependent on the ultrasonic waveform.

For example, FIG. 11 illustrates an example graph 620 showing a combined output signal 622 representative of a dependent sum of the output signals 602, 604 shown in FIG. 9. Time (t) is shown along the horizontal axis and voltage (V) is shown along the vertical axis. As shown in FIG. 11, the RF output signal 602 component of FIG. 9 depends on the peaks of the ultrasonic output signal 604 component of FIG. 9 such that the amplitude of the RF output signal component of the dependent sum combined output signal 622 is reduced when an ultrasonic peak is anticipated. As shown in the example graph 620 in FIG. 11, the peaks have been reduced from 2 to 1.5. In another form, one of the output signals is a function of the other output signal.

Figure 12:
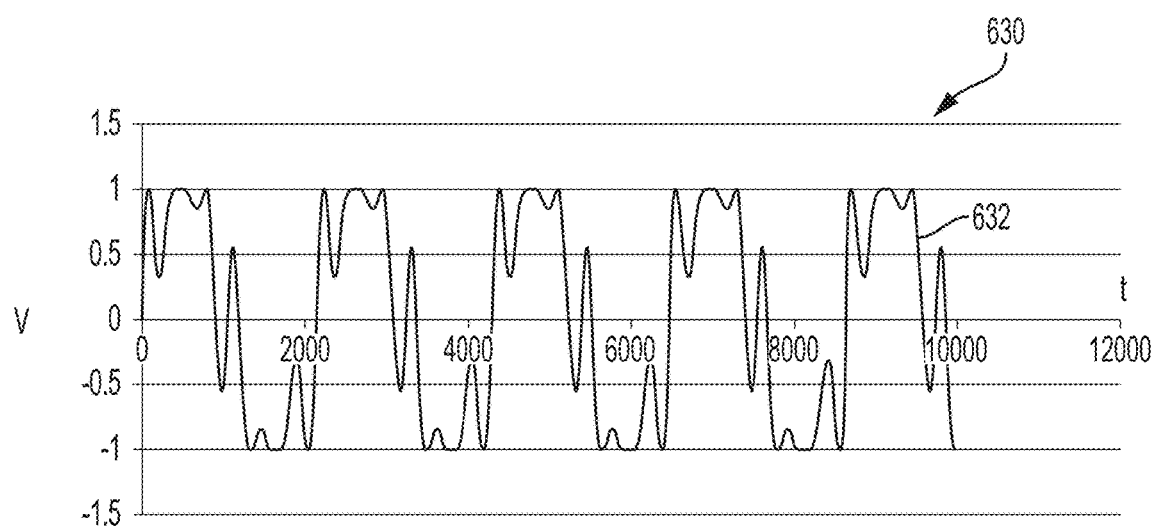
FIG. 12 is an example graph of the sum of the waveforms of FIG. 9 with the RF waveform being a function of the ultrasonic waveform.

For example, FIG. 11 illustrates an example graph 630 showing an output signal 632 representative of a dependent sum of the output signals 602, 604 shown in FIG. 9. Time (t) is shown along the horizontal axis and voltage (V) is shown along the vertical axis. As shown in FIG. 12, the RF output signal is a function of the ultrasonic output signal. This provides a hard limit on the amplitude of the output. As shown in FIG. 12, the ultrasonic output signal is extractable as a sine wave while the RF output signal has distortion but not in a way to affect the coagulation performance of the RF output signal.

Figure 13:
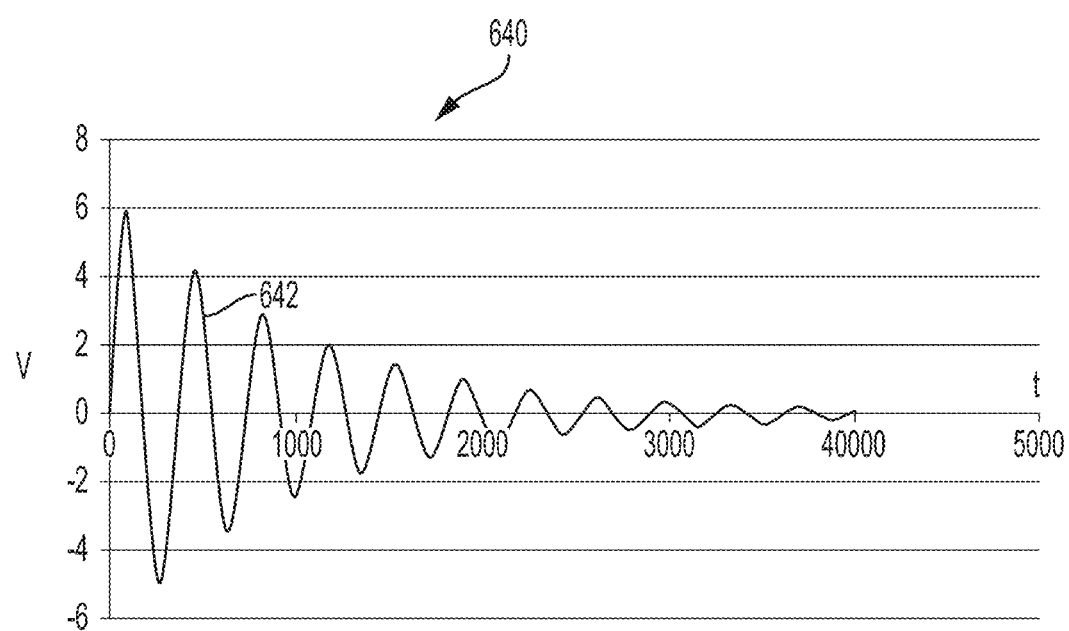
FIG. 13 is an example graph of a complex RF waveform.

A variety of other techniques can be used for compressing and/or limiting the waveforms of the output signals. It should be noted that the integrity of the ultrasonic output signal 604 (FIG. 9) can be more important than the integrity of the RF output signal 602 (FIG. 9) as long as the RF output signal 602 has low frequency components for safe patient levels so as to avoid neuro-muscular stimulation. In another form, the frequency of an RF waveform can be changed on a continuous basis in order to manage the peaks of the waveform. Waveform control is important as more complex RF waveforms, such as a coagulation-type waveform 644, as illustrated in the graph 640 shown in FIG. 13, are implemented with the system. Again, time (t) is shown along the horizontal axis and voltage (V) is shown along the vertical axis.

Figure 14:
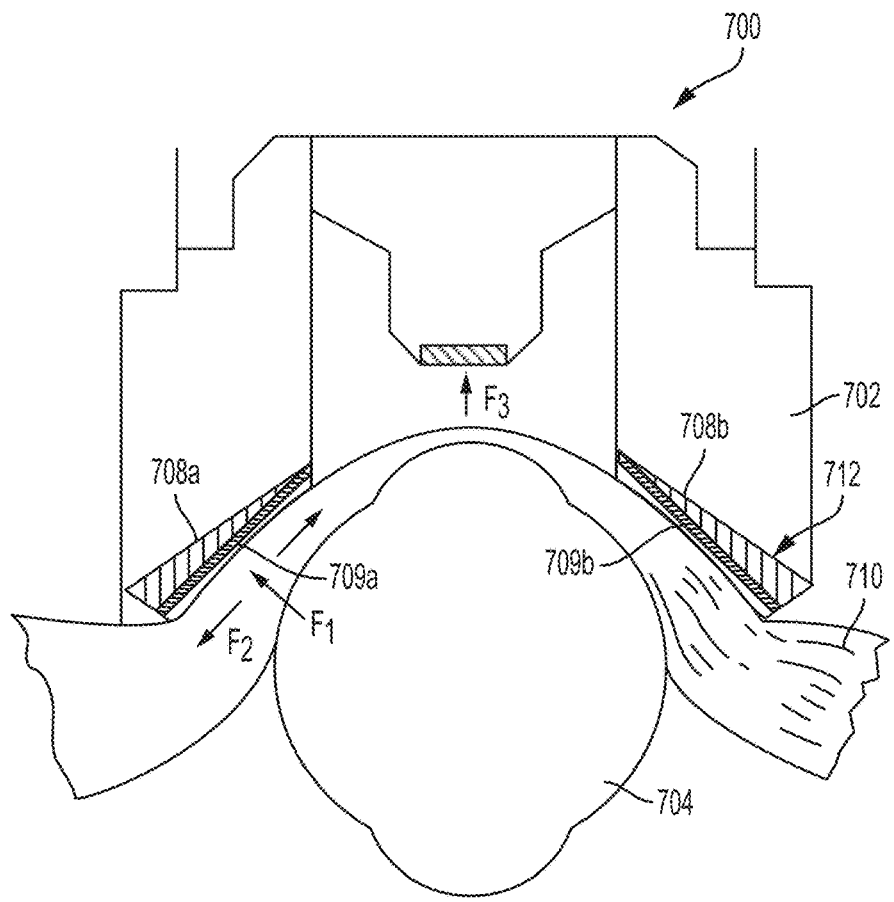
FIG. 14 illustrates one aspect of an end effector comprising RF data sensors located on the clamp arm.

FIGS. 14-42 (26-54) illustrate various configurations of sensors, circuits, and techniques for measuring tissue parameters to facilitate executing the various adaptive tissue identification and treatment technique described herein. FIG. 14 illustrates one aspect of an end effector 700 comprising RF data sensors 706, 708a, 708b located on the clamp arm 702. The end effector 700 comprises a clamp arm 702 and an ultrasonic blade 704. The clamp arm 702 is shown clamping tissue 710 located between the clamp arm 702 and the ultrasonic blade 704. A first sensor 706 is located in a center portion of the clamp arm 702. Second and third sensors 708a, 708b are located on lateral portions of the clamp arm 702. The sensors 706, 708a, 708b are mounted or formed integrally with on a flexible circuit 712 (shown more particularly in FIG. 15 and more particularly segmented flexible circuits 800, 900 shown in FIGS. 17 and 18) configured to be fixedly mounted to the clamp arm 702.

The end effector 700 is an example end effector for the multifunction surgical instrument 108 shown in FIGS. 1 and 2. The sensors 706, 708a, 708b are electrically connected to an energy source, such as for example, the generator 500 shown in FIG. 8. The sensors 706, 708a, 708b are powered by suitable sources within the generator and the signals generated by the sensors 706, 708a, 708b are provided to analog and/or digital processing circuits of the generator 500.

In one aspect, the first sensor 706 is a force sensor to measure a normal force $F_3$ applied to the tissue 710 by the clamp arm 702. The second and third sensors 708a, 708b include one or more elements to apply RF energy to the tissue 710, measure tissue impedance, down force $F_1$, transverse forces $F_2$, and temperature, among other parameters. Electrodes 709a, 709b are electrically coupled to the generator and apply RF energy to the tissue 710. In one aspect, the first sensor 706 and the second and third sensors 708a, 708b are strain gauges to measure force or force per unit area. It will be appreciated that the measurements of the down force $F_1$, the lateral forces $F_2$, and the normal force $F_3$ may be readily converted to pressure by determining the surface area upon which the force sensors 706, 708a, 708b are acting upon. Additionally, as described with particularity herein, the flexible circuit 712 may comprise temperature sensors embedded in one or more layers of the flexible circuit 712. The one or more temperature sensors may be arranged symmetrically or asymmetrically and provide tissue 710 temperature feedback to control circuits of the generator.

Figure 15:
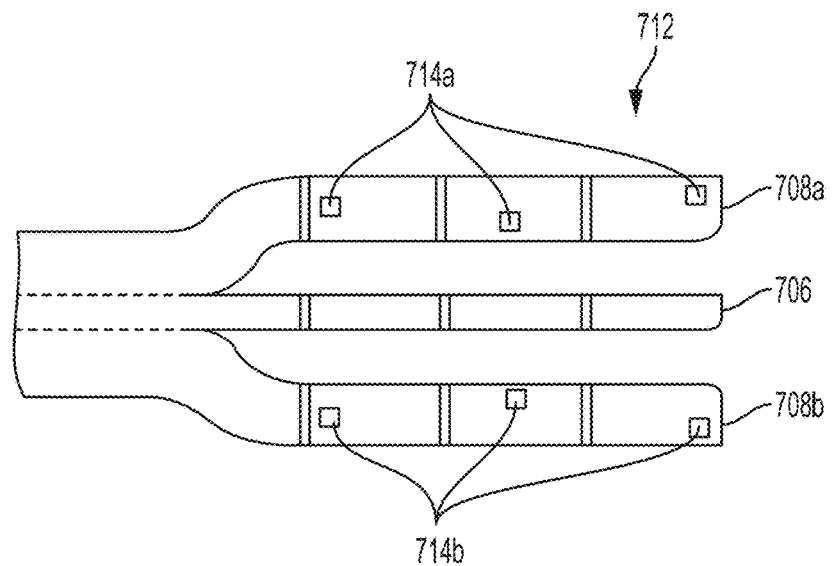
FIG. 15 illustrates one aspect of the flexible circuit shown in FIG. 14 in which the sensors may be mounted to or formed integrally therewith.

FIG. 15 illustrates one aspect of the flexible circuit 712 shown in FIG. 14 in which the sensors 706, 708a, 708b may be mounted to or formed integrally therewith. The flexible circuit 712 is configured to fixedly attach to the clamp arm 702. As shown particularly in FIG. 15, asymmetric temperature sensors 714a, 714b are mounted to the flexible circuit 712 to enable measuring the temperature of the tissue 710 (FIG. 14).

Figure 16:
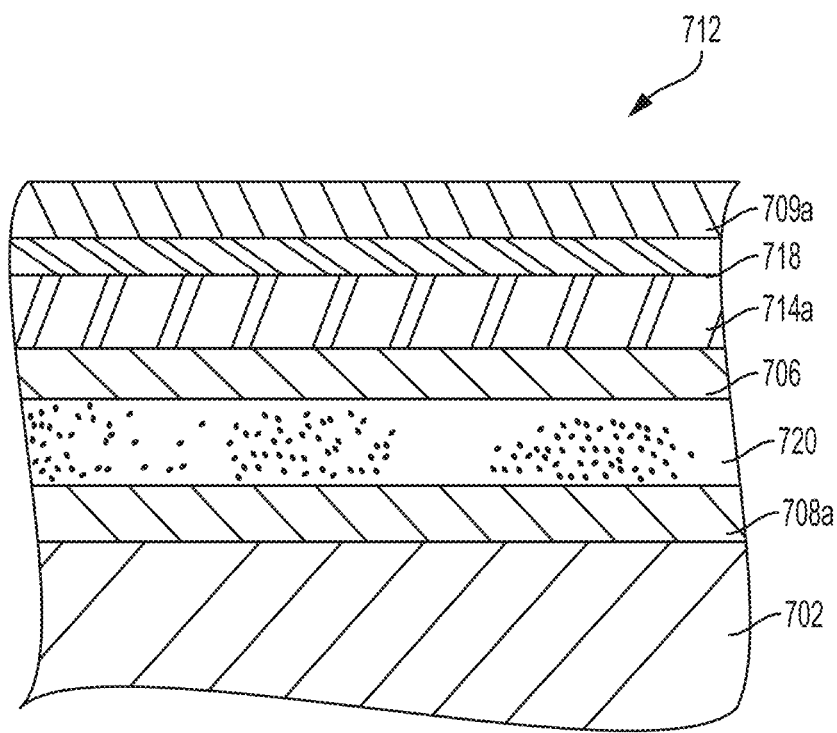
FIG. 16 is a cross-sectional view of the flexible circuit shown in FIG. 15.

FIG. 16 is a cross-sectional view of the flexible circuit 712 shown in FIG. 15. The flexible circuit 712 comprises multiple layers and is fixedly attached to the clamp arm 702. A top layer of the flexible circuit 712 is an electrode 709a, which is electrically coupled to an energy source, such as the generators 102, 200, 300, 400, 500 (FIGS. 1-3 and 4-8), to apply RF energy to the tissue 710 (FIG. 14). A layer of electrical insulation 718 is provided below the electrode 709a layer to electrically isolate the sensors 714a, 706, 708a from the electrode 709a. The temperature sensors 714a are disposed below the layer of electrical insulation 718. The first force (pressure) sensor 706 is located below the layer containing the temperature sensors 714a and above a compressive layer 720. The second force (pressure) sensor 708a is located below the compressive layer 720 and above the clamp arm 702 frame.

Figure 17:
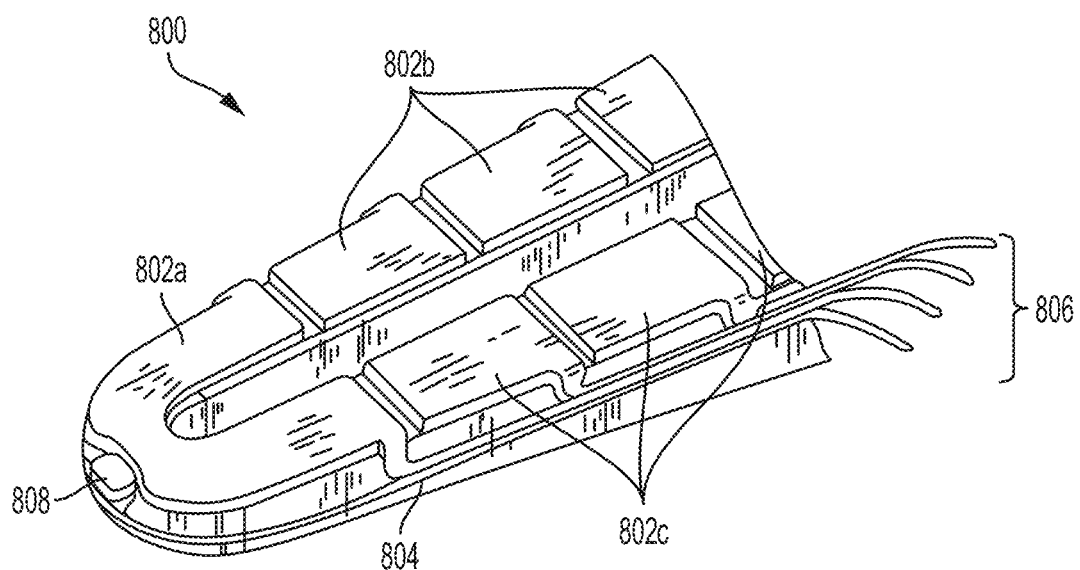
FIG. 17 illustrates one aspect of a segmented flexible circuit configured to fixedly attach to a clamp arm of an end effector.

FIG. 17 illustrates one aspect of a segmented flexible circuit 800 configured to fixedly attach to a clamp arm 804 of an end effector. The segmented flexible circuit 800 comprises a distal segment 802a and lateral segments 802b, 802c that include individually addressable sensors to provide local tissue control, as described herein in connection with FIGS. 14-16, for example. The segments 802a, 802b, 802c are individually addressable to treat tissue and to measure tissue parameters based on individual sensors located within each of the segments 802a, 802b, 802c. The segments 802a, 802b, 802c of the segmented flexible circuit 800 are mounted to the clamp arm 804 and are electrically coupled to an energy source, such as the generators 102, 200, 300, 400, 500 (FIGS. 1-3 and 4-8), via electrical conductive elements 806. A Hall effect sensor 808, or any suitable magnetic sensor, is located on a distal end of the clamp arm 804. The Hall effect sensor 808 operates in conjunction with a magnet to provide a measurement of an aperture defined by the clamp arm 804 aperture or tissue gap as shown with particularity in FIG. 19.

Figure 18:
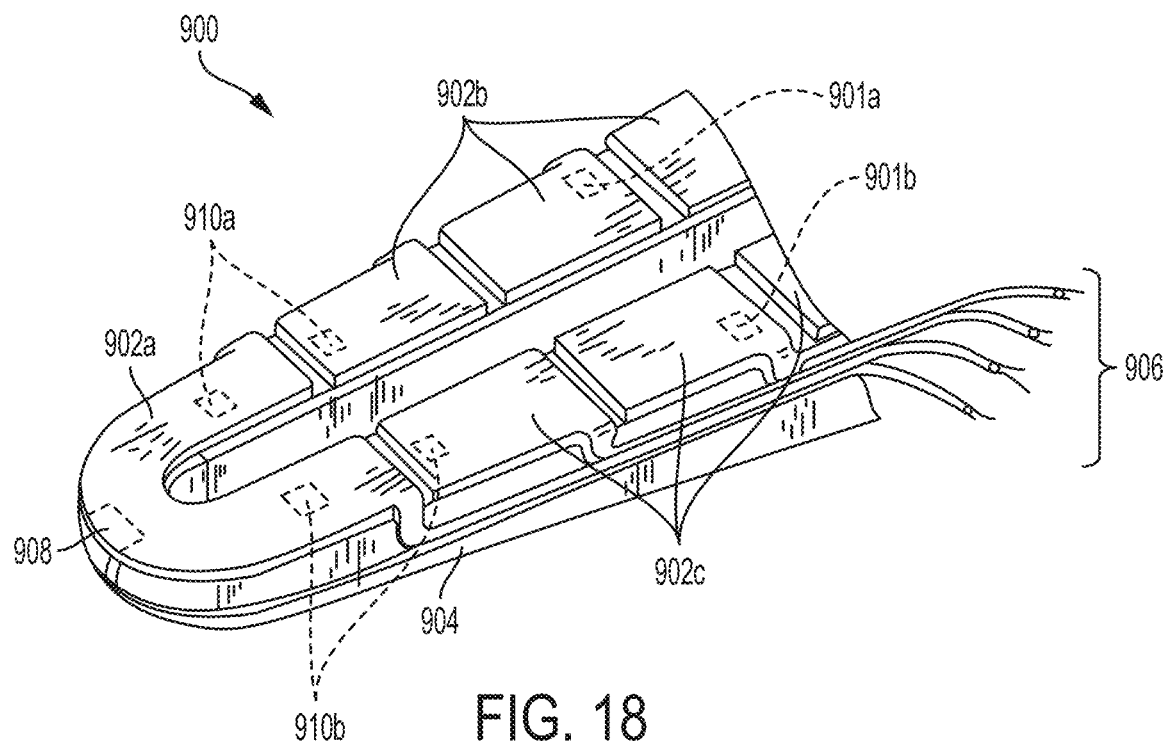
FIG. 18 illustrates one aspect of a segmented flexible circuit configured to mount to a clamp arm of an end effector.

FIG. 18 illustrates one aspect of a segmented flexible circuit 900 configured to mount to a clamp arm 904 of an end effector. The segmented flexible circuit 1900 comprises a distal segment 902a and lateral segments 902b, 902c that include individually addressable sensors for tissue control, as described herein in connection with FIGS. 14-17, for example. The segments 902a, 902b, 902c are individually addressable to treat tissue and to read individual sensors located within each of the segments 902a, 902b, 902c. The segments 902a, 902b, 902c of the segmented flexible circuit 900 are mounted to the clamp arm 904 and are electrically coupled to an energy source, such as the generators 102, 200, 300, 400, 500 (FIGS. 1-3 and 4-8), via electrical conductive elements 906. A Hall effect sensor 908, or other suitable magnetic sensor, is provided on a distal end of the clamp arm 904. The Hall effect sensor 908 operates in conjunction with a magnet to provide a measurement of clamp arm 904 aperture defined by the end effector or tissue gap as shown with particularity in FIG. 19. In addition, a plurality of lateral asymmetric temperature sensors 910a, 910b are mounted on or formally integrally with the segmented flexible circuit 900 to provide tissue temperature feedback to control circuits in the generator.

Figure 19:
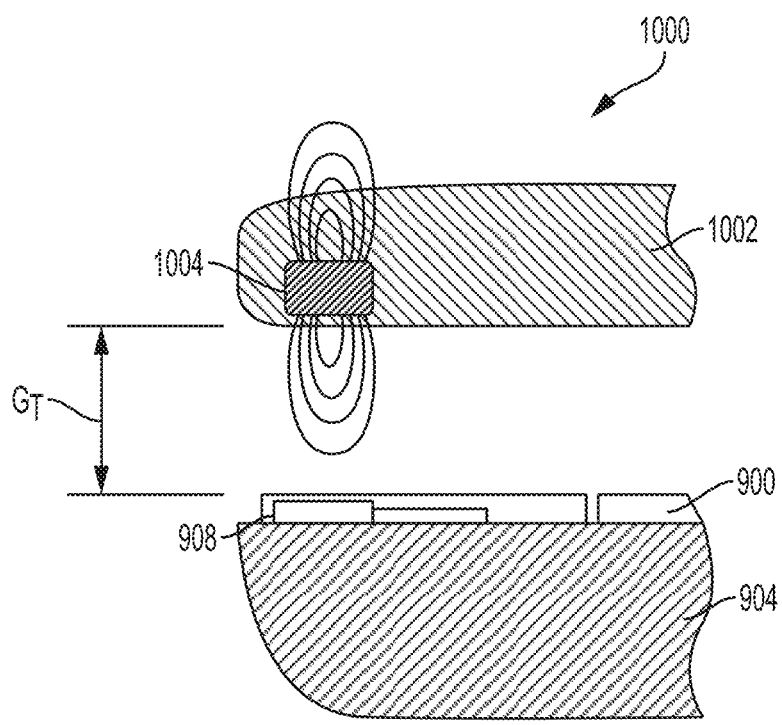
FIG. 19 illustrates one aspect of an end effector configured to measure a tissue gap $G_T$.

FIG. 19 illustrates one aspect of an end effector 1000 configured to measure a tissue gap $G_T$. The end effector 1000 comprises a jaw member 1002 and a clamp arm 904. The flexible circuit 900 as described in FIG. 18, is mounted to the clamp arm 904. The flexible circuit 900 comprises a Hall effect sensor 908 that operates with a magnet 1004 mounted to the jaw member 1002 to measure the tissue gap $G_T$. This technique can be employed to measure the aperture defined between the clamp arm 904 and the jaw member 1002. The jaw member 1002 may be an ultrasonic blade.

Figure 20:
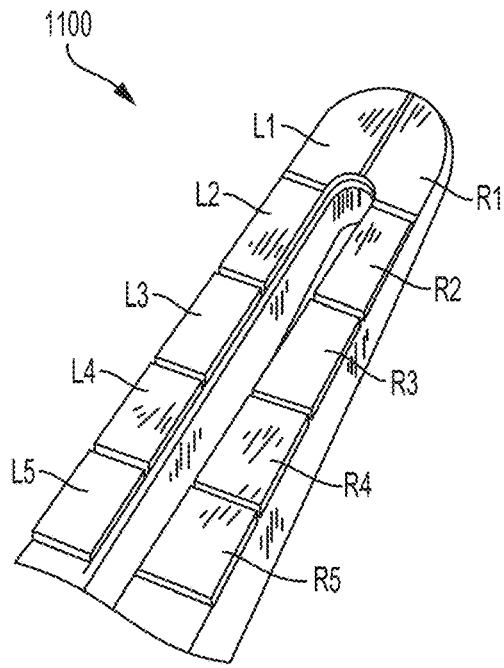
FIG. 20 illustrates one aspect of a left-right segmented flexible circuit.

FIG. 20 illustrates one aspect of a left-right segmented flexible circuit 1100. The left-right segmented flexible circuit 1100 comprises a plurality of segments L1-L5 on the left side of the left-right segmented flexible circuit 1100 and a plurality of segments R1-R5 on the right side of the left-right segmented flexible circuit 1100. Each of the segments L1-L5 and R1-R5 comprise temperature sensors and force sensors to sense tissue parameters locally within each segment L1-L5 and R1-R5. The left-right segmented flexible circuit 1100 are configured to influence the RF treatment energy based on tissue parameters sensed locally within each of the segments L1-L5 and R1-R5.

Figure 21:
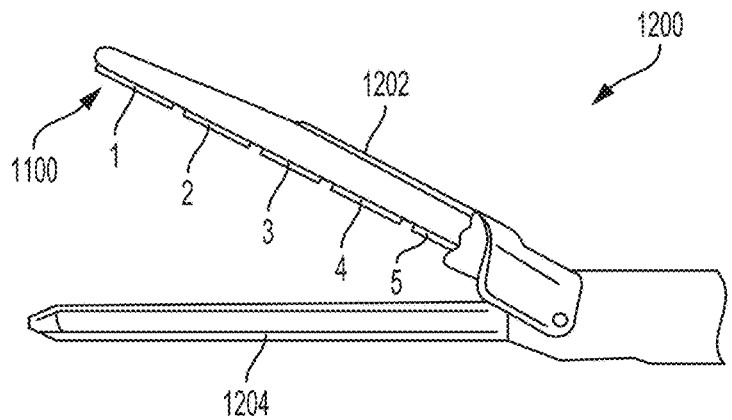
FIG. 21 illustrates one aspect of an end effector comprising segmented flexible circuit as shown in FIG. 20.

FIG. 21 illustrates one aspect of an end effector 1200 comprising segmented flexible circuit 1100 as shown in FIG. 20. The end effector 1200 comprises a clamp arm 1202 and an ultrasonic blade 1204. The segmented flexible circuit 1100 is mounted to the clamp arm 1202. Each of the sensors disposed within the segments 1-5 are configured to detect the presence of tissue positioned between the clamp arm 1202 and the ultrasonic blade 1204 and represent tissue zones 1-5. In the configuration shown in FIG. 21, the end effector 1200 is shown in an open position ready to receive or grasp tissue between the clamp arm 1202 and the ultrasonic blade 1204.

Figure 22:
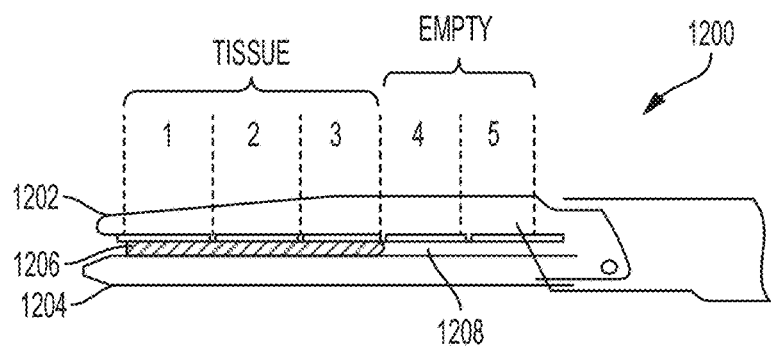
FIG. 22 illustrates the end effector shown in FIG. 21 with the clamp arm clamping tissue between the clamp arm and the ultrasonic blade.

FIG. 22 illustrates the end effector 1200 shown in FIG. 21 with the clamp arm 1202 clamping tissue 1206 between the clamp arm 1202 and the ultrasonic blade 1204. As shown in FIG. 22, the tissue 1206 is positioned between segments 1-3 and represents tissue zones 1-3. Accordingly, tissue 1206 is detected by the sensors in segments 1-3 and the absence of tissue (empty) is detected in section 1208 by segments 4-5. The information regarding the presence and absence of tissue 1206 positioned within certain segments 1-3 and 4-5, respectively, is communicated to a control circuit of the generator, such as the generators 102, 200, 300, 400, 500 (FIGS. 1-3 and 4-8). The generator 500 is configured to energize only the segments 1-3 where tissue 1206 is detected and does not energize the segments 4-5 where tissue is not detected. It will be appreciated that the segments 1-5 may contain any suitable temperature, force/pressure, and/or Hall effect magnetic sensors to measure tissue parameters of tissue located within certain segments 1-5 and electrodes to deliver RF energy to tissue located in certain segments 1-5.

Figure 23:
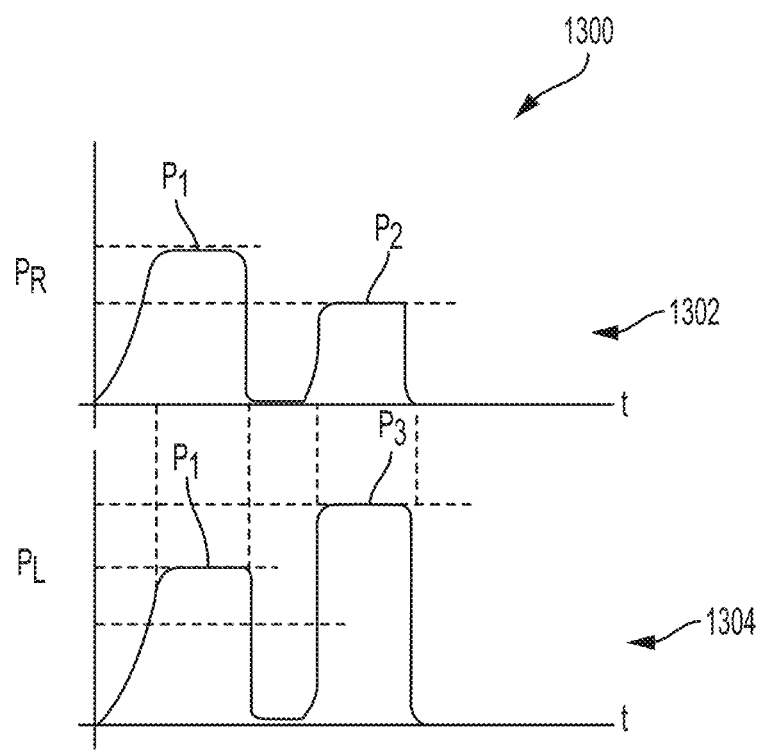
FIG. 23 illustrates graphs of energy applied by the right and left side of an end effector based on locally sensed tissue parameters.

FIG. 23 illustrates graphs 1300 of energy applied by the right and left side of an end effector based on locally sensed tissue parameters. As discussed herein, the clamp arm of an end effector may comprise temperature sensors, force/pressure sensors, Hall effector sensors, among others, along the right and left sides of the clamp arm as shown, for example, in FIGS. 14-22. Thus, RF energy can be selectively applied to tissue positioned between the clam jaw and the ultrasonic blade. The top graph 1302 depicts power $P_R$ applied to a right side segment of the clamp arm versus time (t) based on locally sensed tissue parameters. Thus, the generator, such as the generators 102, 200, 300, 400, 500 (FIGS. 1-3 and 4-8), is configured to measure the sensed tissue parameters and to apply power $P_R$ to a right side segment of the clamp arm. The generator 500 delivers an initial power level $P_1$ to the tissue via the right side segment and then decreases the power level to $P_2$ based on local sensing of tissue parameters (e.g., temperature, force/pressure, thickness) in one or more segments. The bottom graph 1304 depicts power $P_L$ applied to a left side segment of the clamp arm versus time (t) based on locally sensed tissue parameters. The generator 500 delivers an initial power level of $P_1$ to the tissue via the left side segment and then increases the power level to $P_3$ based local sensing of tissue parameters (e.g., temperature, force/pressure, thickness). As depicted in the bottom graph 1304, the generator is configured to re-adjust the energy delivered $P_3$ based on sensing of tissue parameters (e.g., temperature, force/pressure, thickness).

Figure 24:
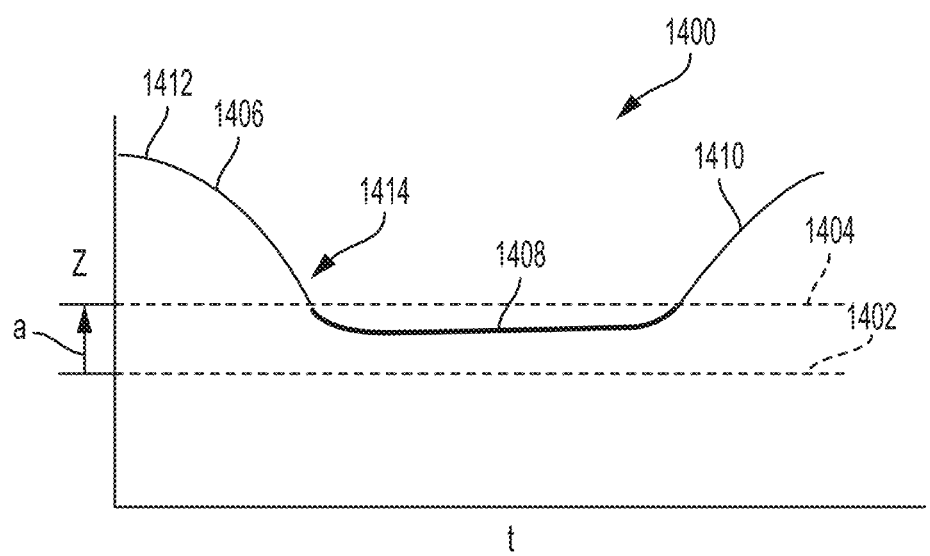

FIG. 24 illustrates a graph 1400 depicting one aspect of adjustment of threshold due to the measurement of a secondary tissue parameter such as continuity, temperature, pressure, and the like. The horizontal axis of the graph 1400 is time (t) and the vertical axis is tissue impedance (Z). The curve 1412 represents the change of tissue impedance (Z) over time (t) as different energy modalities are applied to the tissue. With reference also to FIGS. 20-22, the original threshold 1402 is applied when tissue is detected in all five segments 1-5 (tissue zones 1-5) and the adjusted threshold 1404 is applied when the tissue is detected in tissue segments 1-3 (tissue zones 1-3). Accordingly, once the tissue is located in particulars segments (zones) the control circuit in the generator adjusts the threshold accordingly.

As shown in FIG. 24, the curve 1412 includes three separate sections 1406, 1408, 1410. The first section 1406 of the curve 1412 represents the time when RF energy is applied to the tissue in tissue zones 1-3 until the tissue impedance drops below the adjusted threshold 1404. At that point 1414, which may indicate that a tissue seal is completed, the energy modality applied to tissue zones 1-3 is changed from RF energy to ultrasonic energy. The ultrasonic energy is then applied in the second and third sections 1408, 1410 and the impedance rises exponentially until the tissue is severed or cut.

Figure 25:
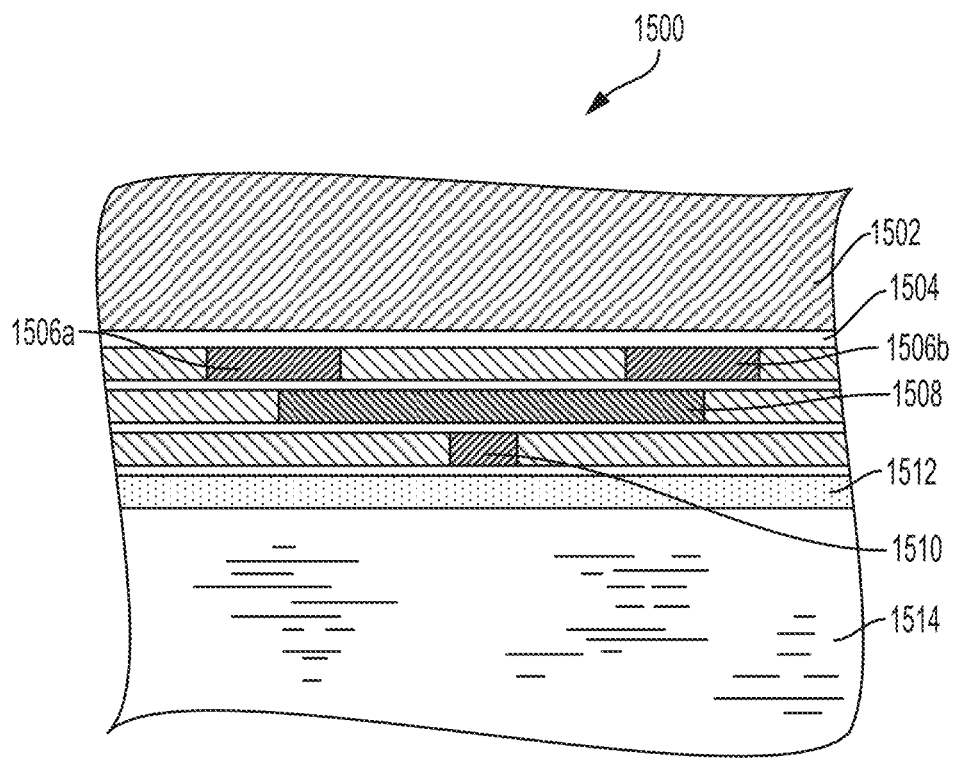
FIG. 25 is a cross-sectional view of one aspect of a flexible circuit comprising RF electrodes and data sensors embedded therein.

FIG. 25 is a cross-sectional view of one aspect of a flexible circuit 1500 comprising RF electrodes and data sensors embedded therein. The flexible circuit 1500 can be mounted to the right or left portion of an RF clamp arm 1502, which is made of electrically conductive material such as metal. Below the RF clamp arm 1502 down force/pressure sensors 1506a, 1506b are embedded below a laminate layer 1504. A transverse force/pressure sensor 1508 is located below the down force/pressure sensor 1506a, 1506b layer and a temperature sensor is 1510 is located below the transverse force/pressure sensor 1508. An electrode 1512 electrically coupled to the generator and configured to apply RF energy to the tissue 1514 is located below the temperature sensor 1510.

Figure 26:
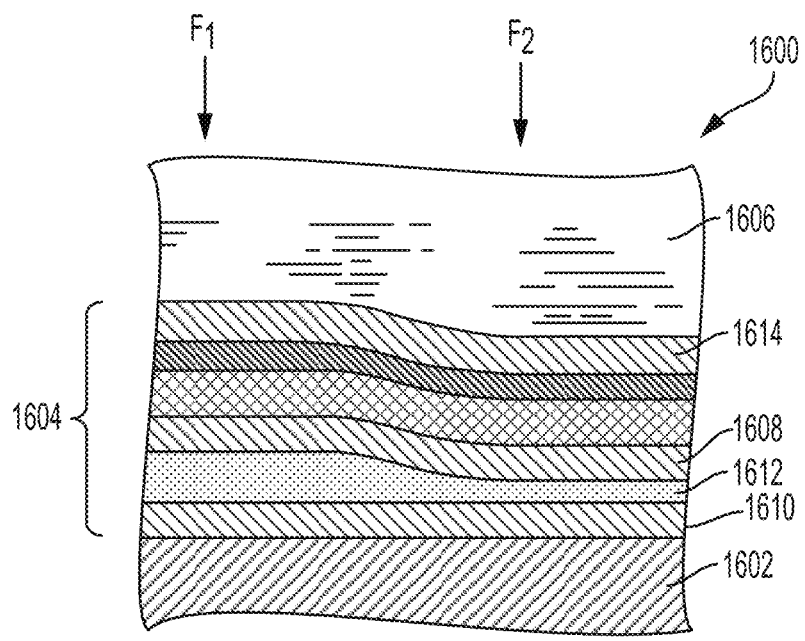
FIG. 26 is a cross-sectional view of one aspect of an end effector configured to sense force or pressure applied to tissue located between a clamp arm and an ultrasonic blade.

FIG. 26 is a cross-sectional view of one aspect of an end effector 1600 configured to sense force or pressure applied to tissue located between a clamp arm and an ultrasonic blade. The end effector 1600 comprises a clamp jaw 1602 and a flexible circuit 1604 fixedly mounted to the clamp arm 1602. The clamp arm 1602 applies forces $F_1$ and $F_2$ to the tissue 1606 of variable density and thickness, which can be measure by first and second force/pressure sensors 1608, 1610 located in different layers of the flexible circuit 1604. A compressive layer 1612 is sandwiched between the first and second force/pressure sensors 1608, 1610. An electrode 1614 is located on outer portion of the flexible circuit 1604 which contacts the tissue. As described herein, other layers of the flexible circuit 1604 may comprise additional sensors such temperature sensors, thickness sensors, and the like.

Figure 27:
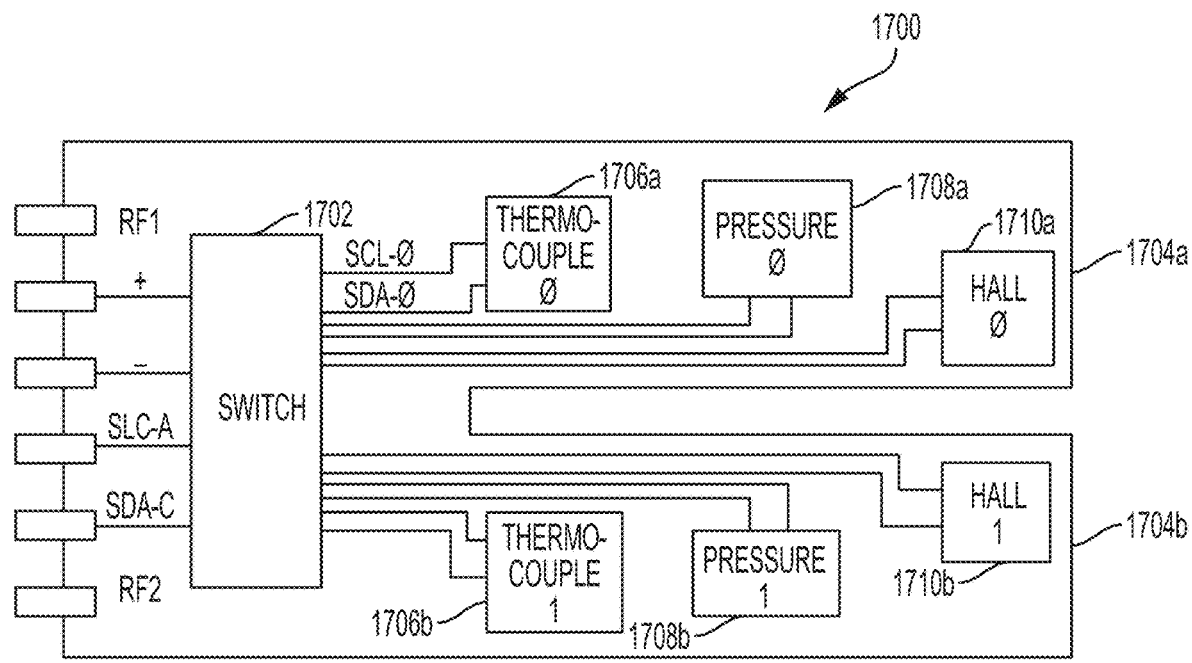
FIG. 27 is a schematic diagram of one aspect of a signal layer of a flexible circuit.
Figure 28:
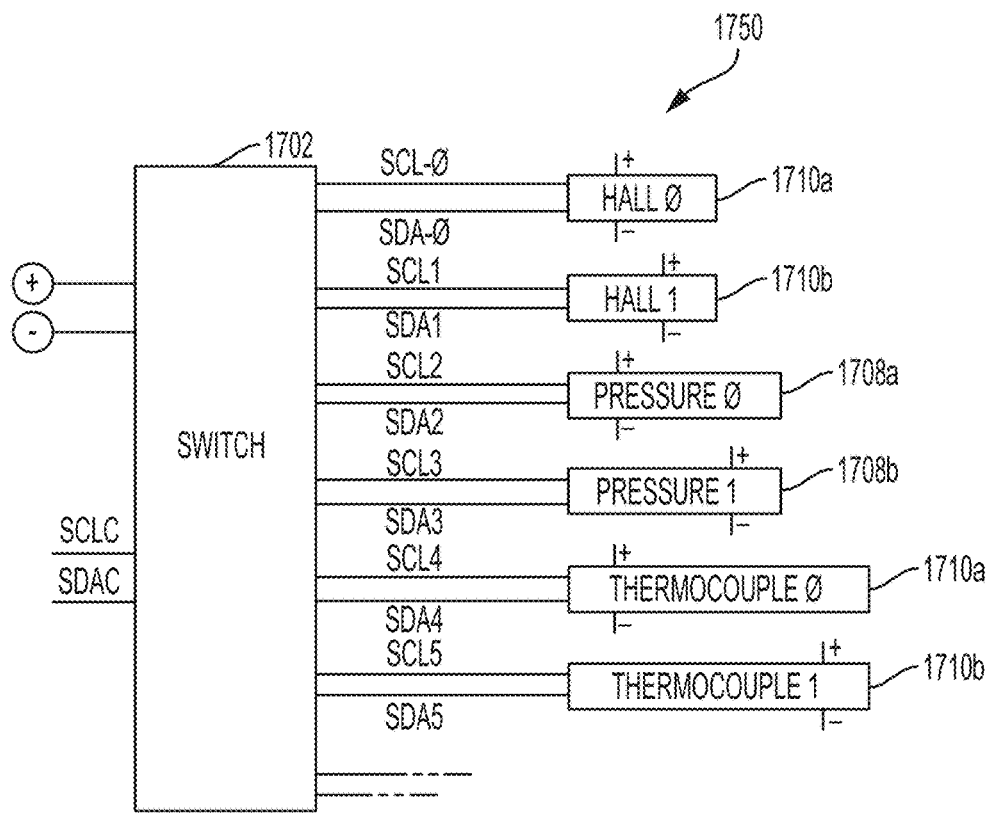
FIG. 28 is a schematic diagram of sensor wiring for the flexible circuit shown in FIG. 27.
Figure 29:
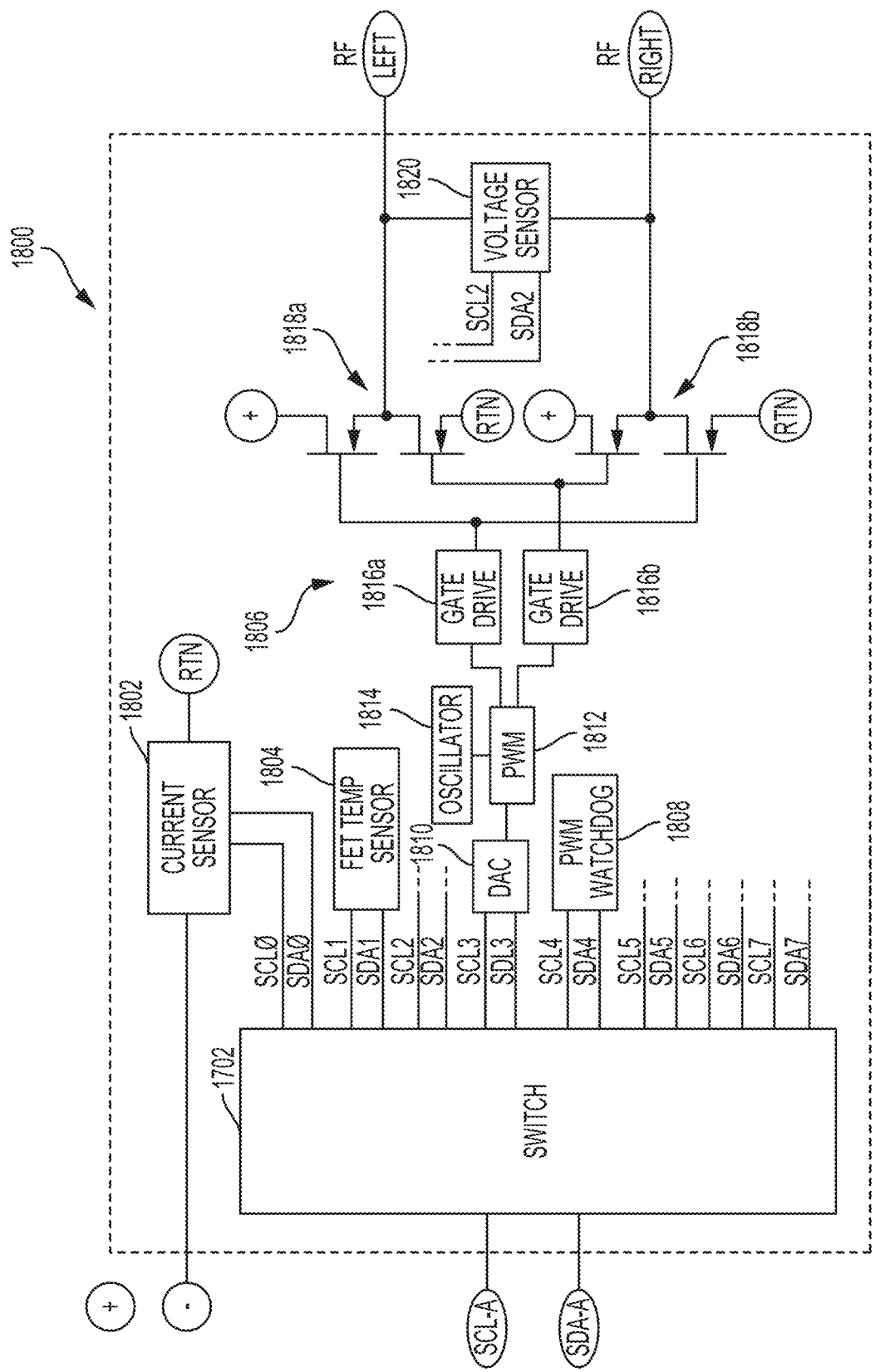
FIG. 29 is a schematic diagram of one aspect of an RF energy drive circuit.

FIGS. 27-29 illustrate various schematic diagrams of flexible circuits of the signal layer, sensor wiring, and an RF energy drive circuit. FIG. 27 is a schematic diagram of one aspect of a signal layer of a flexible circuit 1700. The flexible circuit 1700 comprises multiple layers (~4 to ~6, for example). One layer will supply the integrated circuits with power and another layer with ground. Two additional layers will carry the RF energy RF1 and RF2 separately. An analog multiplexer switch 1702 has eight bidirectional translating switches that can be controlled through the I²C bus. The SCL/SDA upstream pair fans out to eight downstream pairs, or channels. Any individual SCn/SDn channel or combination of channels can be selected, determined by the contents of a programmable control register. The upstream pairs SCL/SDA are connected to a control circuit in the generator. There are six down stream sensors, three on each side of the clamp arm. A first side 1704a comprises a first thermocouple 1706a, a first pressure sensor 1708a, and a first Hall effect sensor 1710a. A second side 1704b comprises a second thermocouple 1706b, a second pressure sensor 1708b, and a second Hall effect sensor 1710b. FIG. 28 is a schematic diagram 1750 of sensor wiring for the flexible circuit 1700 shown in FIG. 27.

FIG. 29 is a schematic diagram of one aspect of an RF energy drive circuit 1800. The RF energy drive circuit 1800 comprises an analog multiplexer 1702 described in connection with FIG. 27. The analog multiplexer multiplexes various signals from the upstream channels SCL/SDA. A current sensor 1802 is coupled in series with the return or ground leg of the power supply circuit to measure the current supplied by the power supply. An FET temperature sensor 1804 provided the ambient temperature. A pulse width modulation (PWM) watchdog timer 1808 automatically generates a system reset if the main program neglects to periodically service it. It is provided to automatically reset the RF energy drive circuit 1800 when it hangs because of a software or hardware fault.

A drive circuit 1806 provides left and right RF energy outputs. The digital signal is provided to the SCL/SDA inputs of the analog multiplexer 1702 from a control circuit of the generator. A digital-to-analog converter (DAC) converts the digital input to an analog output to drive a pulse width modulation (PWM) circuit 1812 coupled to an oscillator 1814. The PWM circuit 1812 provides a first gate drive signal 1816a to a first transistor output stage 1818a to drive a first RF (Left) energy output. The PWM circuit 1812 also provides a second gate drive signal 1816b to a second transistor output stage 1818ab to drive a second RF (Right) energy output.

The circuits 1700, 1750, 1800 described in connection with FIGS. 27-29 are electrically coupled to the generators 200, 300, 400, 500 shown in FIGS. 5-7. For example, the circuits 1700, 1750, 1800 may be coupled to the generator 200 via the signal conditioning circuit 244 and may be coupled to the generator 500 through the interface circuit 520.

Figure 30:
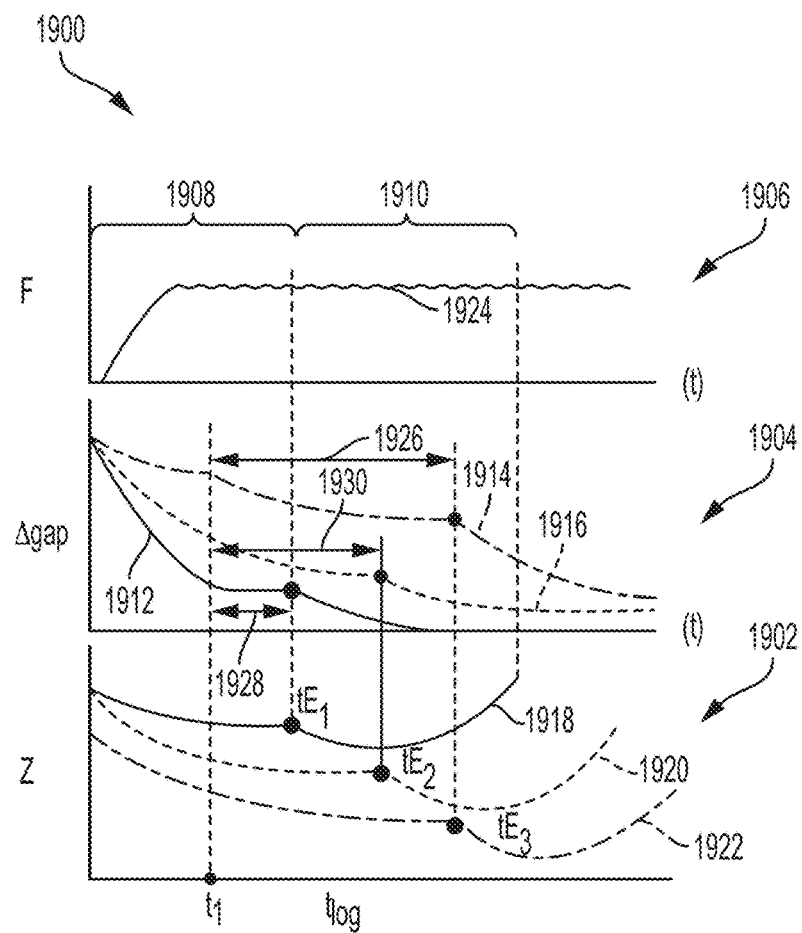
FIG. 30 is a graphical representation of measuring tissue gap at a preset time.

FIG. 30 is a graphical representation 1900 of measuring tissue gap at a preset time. A first graph 1902 represents tissue impedance Z versus time (t) where the horizontal axis represents time (t) and the vertical axis represents tissue impedance Z. A second graph 1904 represents change in tissue gap $\Delta_{gap}$ versus time (t) where the horizontal axis represents time (t) and the vertical axis represents change in tissue gap $\Delta_{gap}$. A third graph 1906 represents force F versus time (t) where the horizontal axis represents time (t) and the vertical axis represents force F. With a constant force F applied to tissue and impedance Z interrogation to define a wait period, energy modality (e.g., RF and ultrasonic) and motor control parameters, displacement at a time provides velocity. With reference to the three graphs 1902, 1904, 1906, impedance sensing energy is applied during a first period 1908 to determine the tissue type such as thin mesentery tissue (solid line), intermediate thickness vessel tissue (dashed line), or thick uterus/bowel tissue (dash-dot line).

As shown in the third graph 1906, the clamp arm initially applies a force which ramps up from zero exponentially until it reaches a constant force 1924. The preset time $t_1$ is selected such that it occurs some time after the clamp arm force reaches a constant force 1924. As shown in the first and second graphs 1902, 1904, from the time the clamp force is applied to the mesentery tissue until the preset time $t_1$ is reached, the change in tissue gap $\Delta_{gap}$ curve 1912 decreases exponentially and the tissue impedance curve 1918 also decreases until the preset time $t_1$ is reached. From the preset time $t_1$, a short delay 1928 is applied before treatment energy is applied to the mesentery tissue at $t_{E1}$.

As shown in the first and second graphs 1902, 1904, from the time the clamp force is applied to the vessel tissue until the preset time $t_1$ is reached, the change in tissue gap $\Delta_{gap}$ curve 1916 also decrease exponentially and the tissue impedance curve 1920 also decreases until the preset time $t_1$ is reached. From the preset time $t_1$, a medium delay 1930 is applied before treatment energy is applied to the vessel tissue at $t_{E2}$.

As shown in the first and second graphs 1902, 1904, from the time the clamp force is applied to the uterus/bowel tissue until the preset time $t_1$ is reached, the change in tissue gap $\Delta_{gap}$ curve 1914 drops exponentially and the tissue impedance curve 1914 also drops until the preset time $t_1$ is reached. From the preset time $t_1$, a short delay 1928 is applied before treatment energy is applied to the mesentery tissue at $t_{E1}$.

Figure 31:
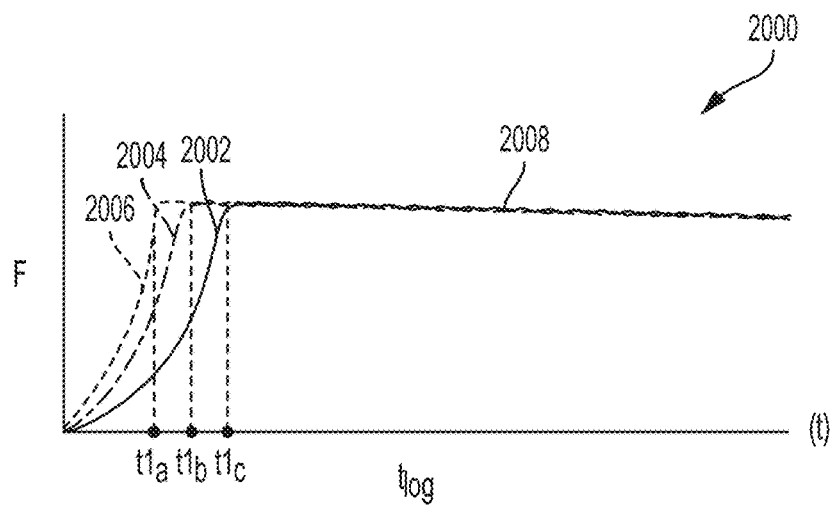
FIG. 31 is a time to preset force versus time graph for thin, medium, and thick tissue types.

FIG. 31 is a time to preset force 2008 versus time graph 2000 for thin, medium, and thick tissue types. The horizontal axis represents time (t) and the vertical axis represents force (F) applied by the clamp arm to the tissue. The graph 2000 depicts three curves, one for thin tissue 2002 shown in solid line, one for medium thickness tissue 2004 shown in dash-dot line, and thick tissue 2006 in dashed line. The graph 2000 depicts measuring time at a preset force as an alternative to tissue gap to control delayed energy mode and other control parameters. Accordingly, the time to preset force 2008 for thick tissue 2006 is $t_{1a}$, the time to preset force 2008 for medium thickness tissue 2004 is $t_{1b}$, and the time to preset force 2008 for thin tissue 2002 is $t_{1c}$.

Once the force reaches the preset force 2008, energy is applied to the tissue. For thin tissue 2002 the time to preset $t_{1c}$>0.5 seconds and then RF energy is applied for an energizing period $t_e$ of about 1-3 seconds. For thick tissue 2006 the time to preset $t_{1a}$<0.5 seconds and then RF energy is applied for an energizing period $t_e$ of about 5-9 seconds. For medium thickness tissue 2004 the time to preset $t_{1b}$ is about 0.5 seconds and then RF energy is applied for an energizing period $t_e$ of about 3 to 5 seconds.

Figure 32:
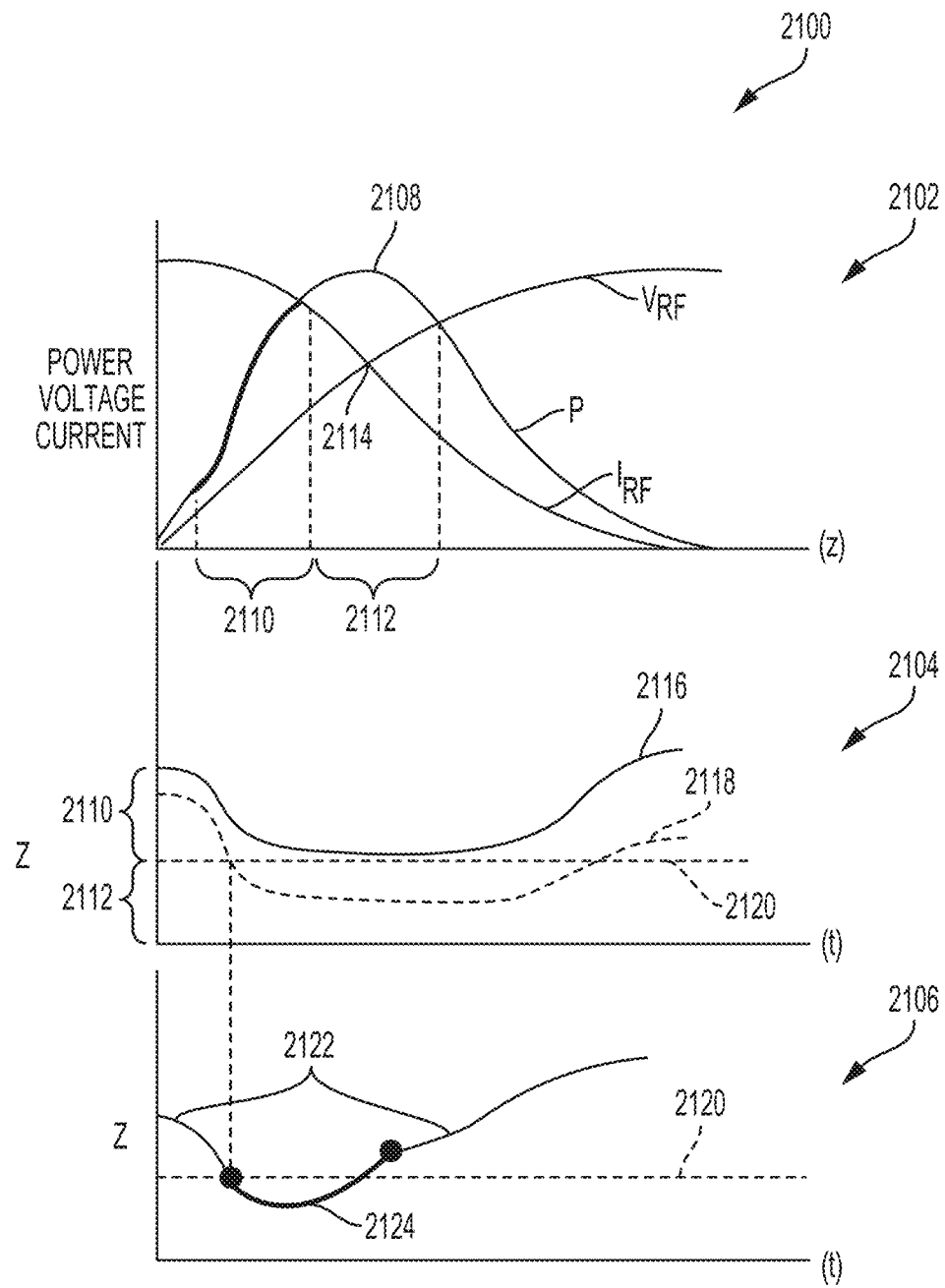
FIG. 32 is a graphical depiction of a graph of three curves, where the first curve represents power (P), voltage ($V_{RF}$), and current ($I_{RF}$) versus tissue impedance (Z), the second curve and third curve represent tissue impedance (Z) versus time (t)

FIG. 32 is a graphical depiction of a graph 2100 of three curves 2102, 2104, 2106, where the first curve 2102 represents power (P), voltage ($V_{RF}$), and current ($I_{RF}$) versus tissue impedance (Z), the second curve 2104 and third curve 2106 represent tissue impedance (Z) versus time (t). The first curve 2102 illustrates the application of power (P) for thick tissue impedance range 2110 and thin tissue impedance range 2112. As the tissue impedance Z increases, the current $I_{RF}$ decrease and the voltage $V_{RF}$ increases. The power curve P increases until it reaches a maximum power output 2108 which coincides with the intersection 2114 of the current $I_{RF}$ and voltage $V_{RF}$ curves.

The second curve 2104 represents the measured tissue impedance Z versus time (t). The tissue impedance threshold limit 2120 is the cross over limit for switching between the RF and ultrasonic energy modalities. For example, as shown in FIG. 32, RF energy is applied while the tissue impedance is above the tissue impedance threshold limit 2120 and ultrasonic energy 2124 is applied while the tissue impedance is below the tissue impedance threshold limit 2120. Accordingly, with reference back to the second curve 2104, the tissue impedance of the thin tissue curve 2116 remains above the tissue impedance threshold limit 2120, thus only RF energy modality is applied to the tissue. On the other hand, RF energy modality is applied to the tick tissue while the impedance is above the tissue impedance threshold limit 2120 and ultrasonic energy is applied to the tissue when the impedance is below the tissue impedance threshold limit 2120. Accordingly, the energy modality switches from RF to ultrasonic when the tissue impedance falls below the tissue impedance threshold limit 2120 and the energy modality switches from ultrasonic to RF when the tissue impedance rises above the tissue impedance threshold limit 2120.

Figure 33:
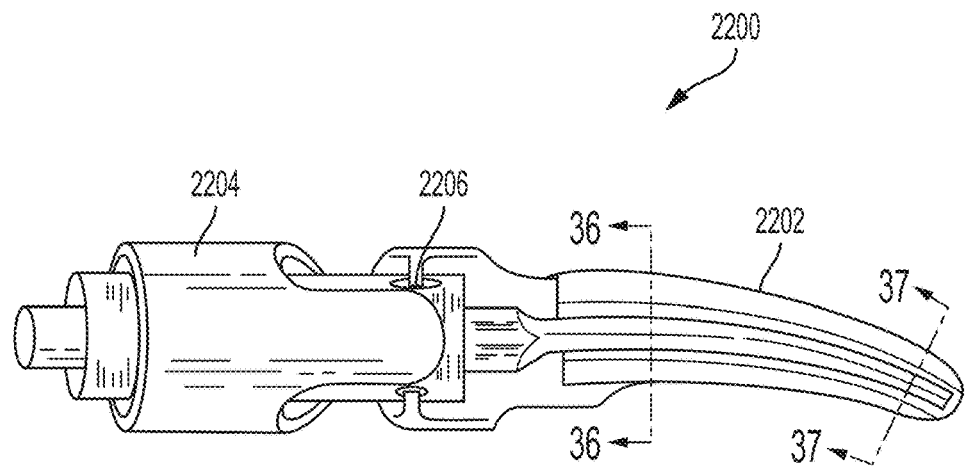
FIG. 33 is a plan view of one aspect of an end effector.
Figure 34:
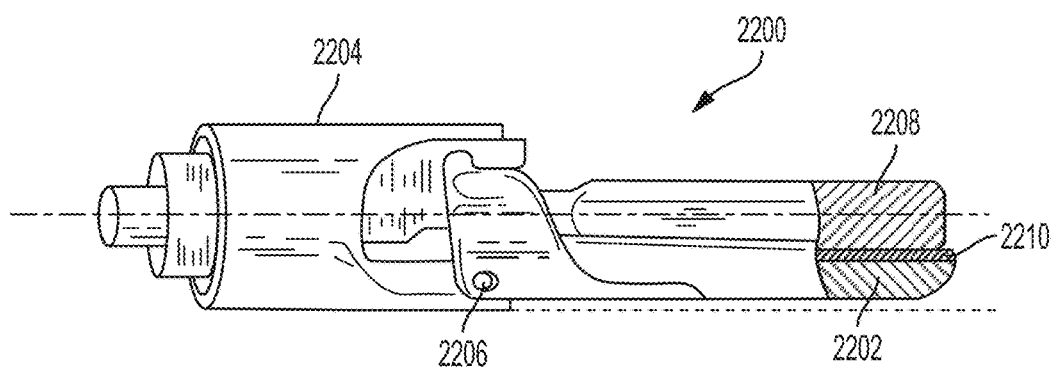
FIG. 34 is a side view of the end effector shown in FIG. 33 with a partial cut away view to expose the underlying structure of the clamp arm and an ultrasonic blade.
Figure 35:
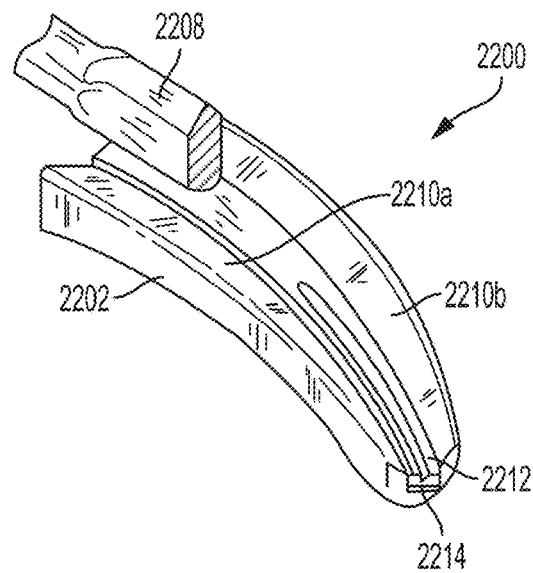
FIG. 35 is partial sectional view of the end effector shown in FIGS. 33, 34 to expose the ultrasonic blade and right and left electrodes, respectively.

FIG. 33 is a plan view of one aspect of an end effector 2200. The end effector 2200 comprises a clamp arm 2202 and a shaft 2204. The clamp arm 2202 pivots about pivot point 2206 and defines a pivot angle. FIG. 34 is a side view of the end effector 2200 shown in FIG. 33 with a partial cut away view to expose the underlying structure of the clamp arm 2202 and an ultrasonic blade 2208. An electrode 2210 is fixedly mounted to the clamp arm 2202. The electrode 2210 is electrically coupled to the generator and is configured to apply RF energy to tissue located between the clamp arm 2202 and the ultrasonic blade 2208. FIG. 35 is partial sectional view of the end effector shown in FIGS. 33, 34 to expose the ultrasonic blade and right and left electrodes 2210a, 2210b, respectively.

Figure 36:
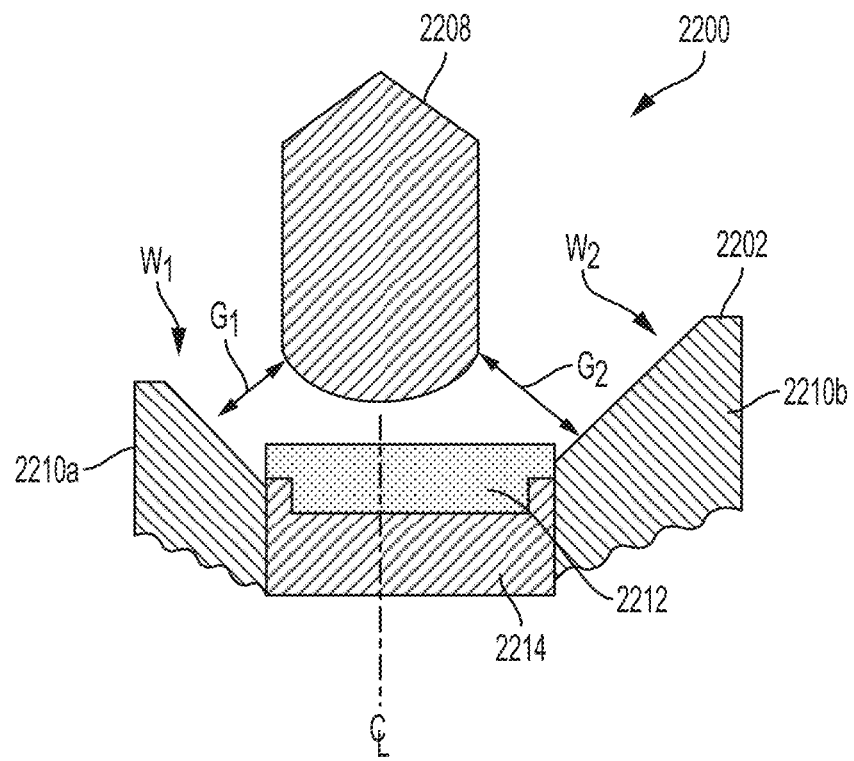
FIG. 36 is a cross-sectional view taken at section 36-36 of the end effector shown in FIG. 33.

FIG. 36 is a cross-sectional view taken at section 36-36 of the end effector 2200 shown in FIG. 33. The end effector 2200 comprises an ultrasonic blade 2208 acoustically coupled to an ultrasonic transducer which is electrically driven by the generator. The clamp arm 2202 comprises an electrode 2210a on the right side and an electrode 2210b on the left side (from the perspective of the operator). The right side electrode 2210a defines a first width $W_1$ and defines a first gap $G_1$ between the electrode 2210a and the ultrasonic blade 2208. The left side electrode 2210b defines a second width $W_2$ and defines a second gap $G_2$ between the electrode 2210b and the ultrasonic blade 2208. In one aspect the first width $W_1$ is less than the second width $W_2$ and the first gap $G_1$ is less than the second gap $G_2$. With reference also to FIG. 35, a soft polymeric pad 2212 is located between the ultrasonic blade 2208 and the clamp arm 2202. A high density polymeric pad 2214 is located adjacent the soft polymeric pad 2212 to prevent the ultrasonic blade 2208 from shorting the electrodes 2210a, 2210b. In one aspect, the soft polymeric pads 2212, 2214 can be made of polymers known under the tradename TEFLON (polytetrafluoroethylene polymers and copolymers), for example.

Figure 37:
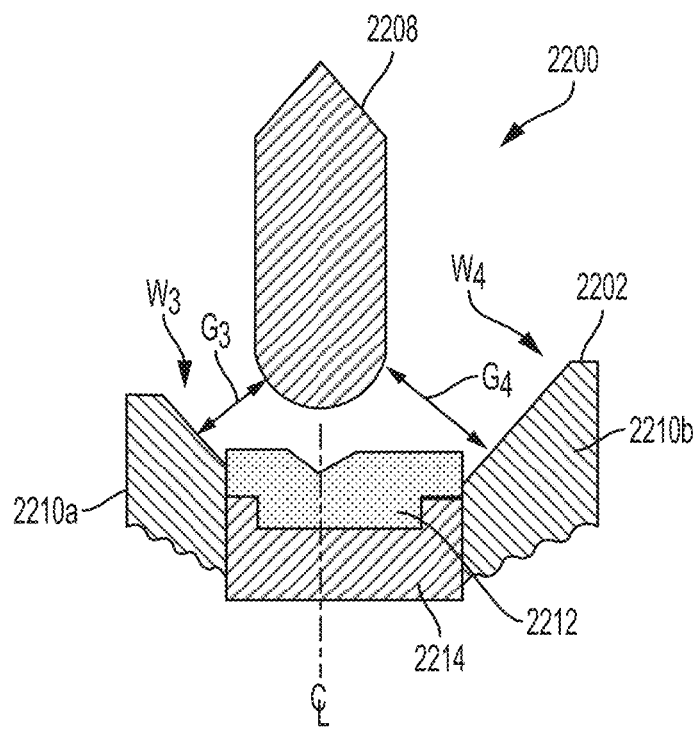
FIG. 37 is cross-sectional view taken at section 37-37 of the end effector shown in FIG. 33.

FIG. 37 is cross-sectional view taken at section 37-37 of the end effector 2200 shown in FIG. 33. At the plane where section 37-37 the end effector 2200 is thinner and has more curvature than section 36-36. The right side electrode 2210a defines a third width $W_3$ and defines a third gap $G_3$ between the electrode 2210a and the ultrasonic blade 2208. The left side electrode 2210b defines a fourth width $W_4$ and defines a fourth gap $G_4$ between the electrode 2210b and the ultrasonic blade 2208. In one aspect the third width $W_3$ is less than the fourth width $W_4$ and the third gap $G_3$ is less than the fourth gap $G_4$.

Figure 38:
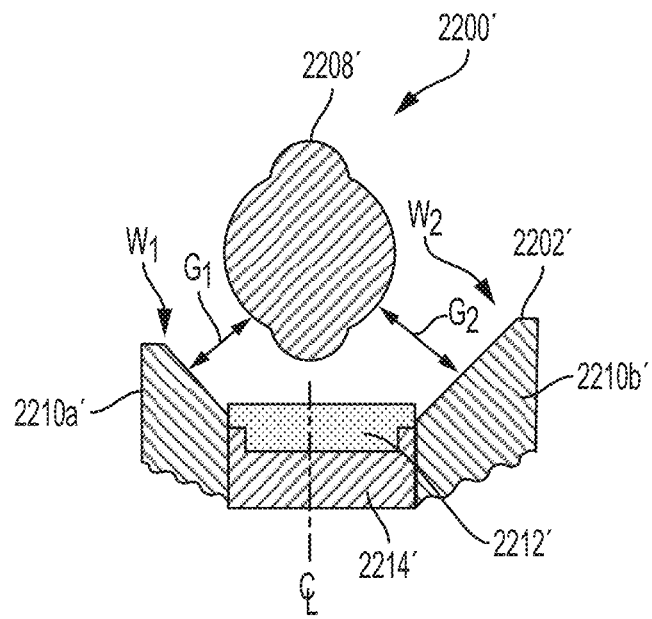
FIG. 38 is a cross-sectional view taken at section 36-36 of the end effector shown in FIG. 33, except that the ultrasonic blade has a different geometric configuration.

FIG. 38 is a cross-sectional view taken at section 36-36 of the end effector 2200 shown in FIG. 33, except that the ultrasonic blade 2208' has a different geometric configuration. The end effector 2200' comprises an ultrasonic blade 2208' cacoustically coupled to an ultrasonic transducer which is electrically driven by the generator. The clamp arm 2202' comprises an electrode 2210a' on the right side and an electrode 2210b' on the left side (from the perspective of the operator). The right side electrode 2210a' defines a first width $W_1$ and defines a first gap $G_1$ between the electrode 2210a' and the ultrasonic blade 2208'. The left side electrode 2210b' defines a second width $W_2$ and defines a second gap $G_2$ between the electrode 2210b' and the ultrasonic blade 2208'. In one aspect the first width $W_1$ is less than the second width $W_2$ and the first gap $G_1$ is less than the second gap $G_2$. A high density polymeric pad 2214' is located adjacent the soft polymeric pad 2212' to prevent the ultrasonic blade 2208' from shorting the electrodes 2210a', 2210b'. In one aspect, the soft polymeric pads 2212', 2214' can be made of polymers known under the tradename TEFLON (polytetrafluoroethylene polymers and copolymers), for example.

Figure 39:
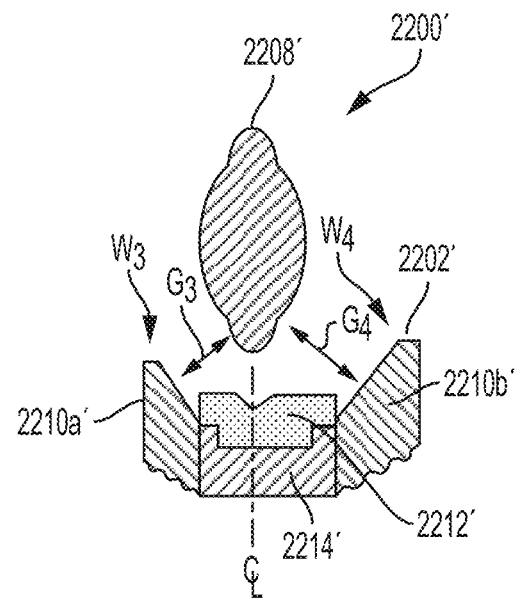
FIG. 39 is cross-sectional view taken at section 37-37 of the end effector shown in FIG. 33, except that the ultrasonic blade has a different geometric configuration.

FIG. 39 is cross-sectional view taken at section 37-37 of the end effector 2200 shown in FIG. 33, except that the ultrasonic blade 2208' has a different geometric configuration. At the plane where section 37-37 the end effector 2200' is thinner and has more curvature than the end effector 2200' at section 36-36. The right side electrode 2210a' defines a third width $W_3$ and defines a third gap $G_3$ between the electrode 2210a' and the ultrasonic blade 2208'. The left side electrode 2210b' defines a fourth width $W_4$ and defines a fourth gap $G_4$ between the electrode 2210b' and the ultrasonic blade 2208'. In one aspect the third width $W_3$ is less than the fourth width $W_4$ and the third gap $G_3$ is less than the fourth gap $G_4$.

Figure 40:
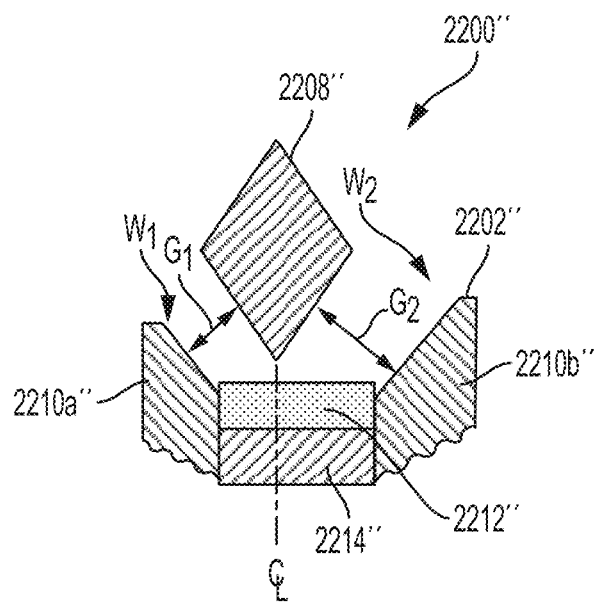
FIG. 40 is a cross-sectional view taken at section 36-36 of the end effector shown in FIG. 33, except that the ultrasonic blade has a different geometric configuration.

FIG. 40 is a cross-sectional view taken at section 36-36 of the end effector 2200 shown in FIG. 33, except that the ultrasonic blade 2208" has a different geometric configuration. The end effector 2200" comprises an ultrasonic blade 2208" cacoustically coupled to an ultrasonic transducer which is electrically driven by the generator. The clamp arm 2202" comprises an electrode 2210a" on the right side and an electrode 2210b" on the left side (from the perspective of the operator). The right side electrode 2210a" defines a first width $W_1$ and defines a first gap $G_1$ between the electrode 2210a" and the ultrasonic blade 2208". The left side electrode 2210b" defines a second width $W_2$ and defines a second gap $G_2$ between the electrode 2210b" and the ultrasonic blade 2208". In one aspect the first width $W_1$ is less than the second width $W_2$ and the first gap $G_1$ is less than the second gap $G_2$. A high density polymeric pad 2214" is located adjacent the soft polymeric pad 2212" to prevent the ultrasonic blade 2208" from shorting the electrodes 2210a", 2210b". In one aspect, the polymeric pads 2212", 2214" can be made of polymers known under the tradename TEFLON (polytetrafluoroethylene polymers and copolymers), for example.

Figure 41:
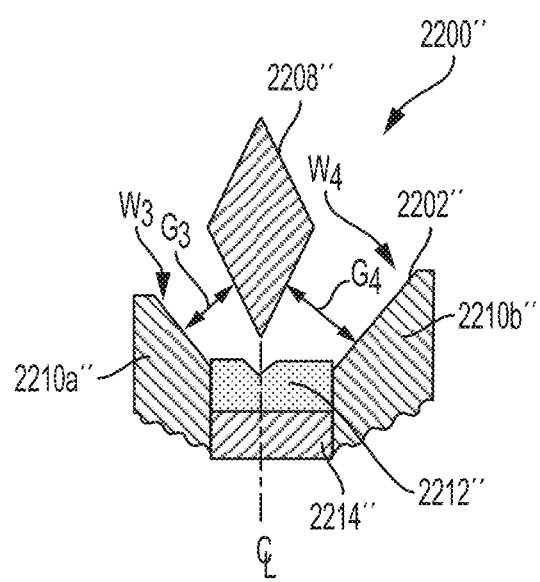
FIG. 41 is cross-sectional view taken at section 37-37 of the end effector shown in FIG. 33, except that the ultrasonic blade has a different geometric configuration.

FIG. 41 is cross-sectional view taken at section 37-37 of the end effector 2200 shown in FIG. 33, except that the ultrasonic blade 2208" has a different geometric configuration. At the plane where section 37-37 the end effector 2200" is thinner and has more curvature than the end effector 2200" at section 36-36. The right side electrode 2210a" defines a third width $W_3$ and defines a third gap $G_3$ between the electrode 2210a" and the ultrasonic blade 2208". The left side electrode 2210b" defines a fourth width $W_4$ and defines a fourth gap $G_4$ between the electrode 2210b" and the ultrasonic blade 2208". In one aspect the third width $W_3$ is less than the fourth width $W_4$ and the third gap $G_3$ is less than the fourth gap $G_4$.

The surgical instruments described herein also can include features to allow the energy being delivered by the generator to be dynamically changed based on the type of tissue being treated by an end effector of a surgical instrument and various characteristics of the tissue. In one aspect, a technique for controlling the power output from a generator, such as the generators 102, 200, 300, 400, 500 (FIGS. 1-3 and 4-8), that is delivered to the end effector of the surgical instrument can include an input that represents the tissue type to allow the energy profile from the generator to be dynamically changed during the procedure based on the type of tissue being effected by the end effector of the surgical instrument.

As disclosed herein, techniques for controlling a generator based on the tissue type may be provided. Various techniques can be used to select a power profile to allow the energy being delivered from the generator to dynamically change based on the tissue type being treated by the surgical instrument.

Figure 42A:
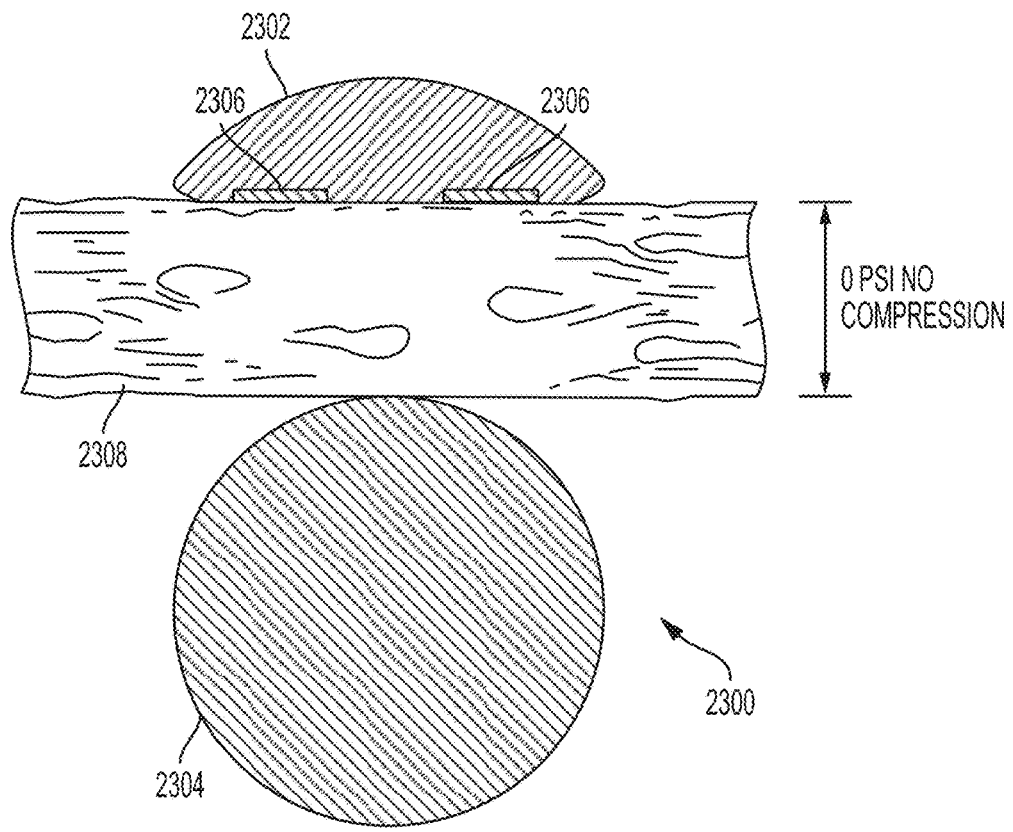
FIG. 42A is a graphical representation of one aspect of a medical device surrounding tissue.

FIG. 42A illustrates an end effector 2300 comprising a clamp arm 2302 and an ultrasonic blade 2304, where the clamp arm 2302 includes electrodes 2306. The end effector 2300 can be employed in one of the surgical instruments 104, 106, 108 referred to in FIGS. 1-3. In addition to the end effector 122, 124, 125, the surgical instruments 104, 106, 108 include a handpiece 105, 107, 109 and a shaft 126, 127, 129, respectively. The end effectors 122, 124, 125 may be used to compress, cut, and/or seal tissue. Referring to FIG. 42A, the end effector 2300, similar to the end effectors 122, 124, 125 shown in FIGS. 1-3, may be positioned by a physician to surround tissue 2308 prior to compression, cutting, or stapling. As shown in FIG. 42A, no compression may be applied to the tissue while preparing to use the end effector 2300. As shown in FIG. 42A, the tissue 2308 is not under compression between the clamp arm 2302 and the ultrasonic blade 2304.

Figure 42B:
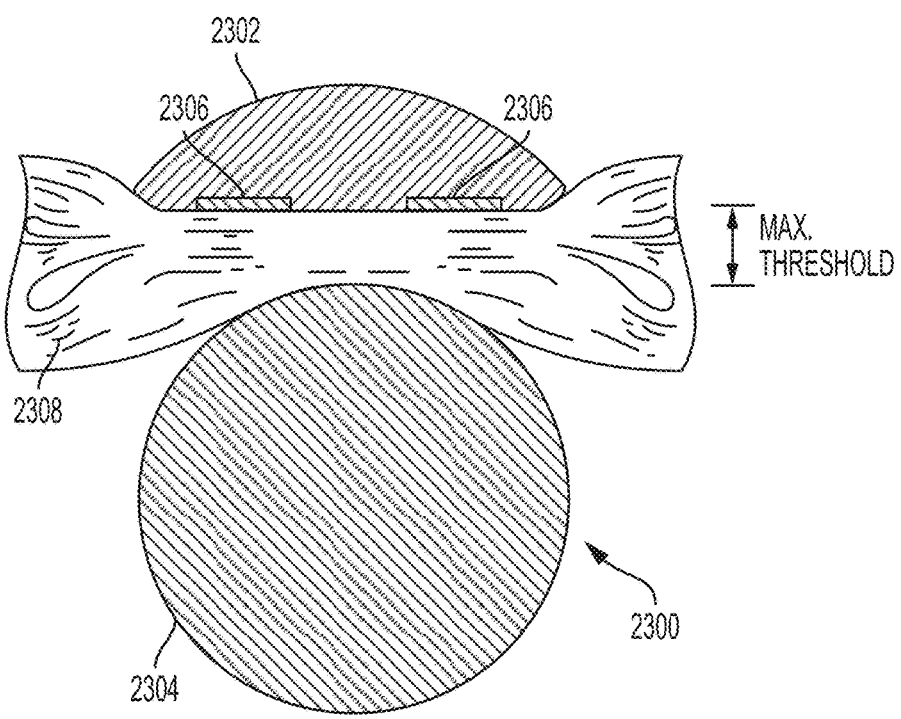
FIG. 42B is a graphical representation of one aspect of a medical device compressing tissue.

Referring now to FIG. 42B, by engaging the trigger on the handle of a surgical instrument, the physician may use the end effector 2300 to compress the tissue 2308. In one aspect, the tissue 2308 may be compressed to its maximum threshold, as shown in FIG. 42B. As shown in FIG. 42A, the tissue 2308 is under maximum compression between the clamp arm 2302 and the ultrasonic blade 2304.

Referring to FIG. 43A, various forces may be applied to the tissue 2308 by the end effector 2300. For example, vertical forces F1 and F2 may be applied by the clamp arm 2302 and the ultrasonic blade 2304 of the end effector 2300 as tissue 2308 is compressed between the two. Referring now to FIG. 43B, various diagonal and/or lateral forces also may be applied to the tissue 2308 when compressed by the end effector 2300. For example, a force F3 may be applied. For the purposes of operating a medical device such as the surgical instruments 104, 106, 108 it may be desirable to sense or calculate the various forms of compression being applied to the tissue by the end effector. For example, knowledge of vertical or lateral compression may allow the end effector to more precisely or accurately apply a staple operation or may inform the operator of the surgical instrument such that the surgical instrument can be used more properly or safely.

In one form, a strain gauge can be used to measure the force applied to the tissue 2308 by the end effector shown in FIGS. 42A-B and 43A-B. A strain gauge can be coupled to the end effector 2300 to measure the force on the tissue 2308 being treated by the end effector 2300. With reference now also to FIG. 44, in the aspect illustrated in FIG. 44, a system 2400 for measuring forces applied to the tissue 2308 comprises a strain gauge sensor 2402, such as, for example, a micro-strain gauge, is configured to measure one or more parameters of the end effector 2300 such as, for example, the amplitude of the strain exerted on a clamp arm of an end effector, such as the clamp arm 2302 of FIGS. 43A-B, during a clamping operation, which can be indicative of the tissue compression. The measured strain is converted to a digital signal and provided to a processor 2410 of a microcontroller 2408. A load sensor 2404 can measure the force to operate the ultrasonic blade 2304 to cut the tissue 2308 captured between the clamp arm 2302 and the ultrasonic blade 2304 of the end effector 2300. A magnetic field sensor 2406 can be employed to measure the thickness of the captured tissue 2308. The measurement of the magnetic field sensor 2406 also may be converted to a digital signal and provided to the processor 2410.

Further to the above, a feedback indicator 2414 also can be configured to communicate with the microcontroller 2408. In one aspect, the feedback indicator 2414 can be disposed in the handle of a surgical instrument, such as those shown in FIGS. 1-3. Alternatively, the feedback indicator 2414 can be disposed in a shaft assembly of a surgical instrument, for example. In any event, the microcontroller 2408 may employ the feedback indicator 2414 to provide feedback to an operator of the surgical instrument with regard to the adequacy of a manual input such as, for example, a selected position of a firing trigger that is used to cause the end effector to clamp down on tissue. To do so, the microcontroller 2408 may assess the selected position of the clamp arm 2302 and/or firing trigger. The measurements of the tissue 2308 compression, the tissue 2308 thickness, and/or the force required to close the end effector 2300 on the tissue, as respectively measured by the sensors 2402, 2404, 2406, can be used by the microcontroller 2408 to characterize the selected position of the firing trigger and/or the corresponding value of the speed of end effector. In one instance, a memory 2412 may store a technique, an equation, and/or a look-up table which can be employed by the microcontroller 2408 in the assessment.

The generators 102, 200, 300, 400, 500 (FIGS. 1-3 and 4-8), surgical instruments 104, 106, 108 (FIGS. 1-3), and end effectors 122, 124, 125, 700, 800, 900, 1000, 1100, 1200, 2200, 2200', 2200", 2300 (FIGS. 1-3, 14-22, 33-43B) described herein may be employed alone or in combination to perform surgical procedures in accordance with the techniques and processes described hereinbelow. Nevertheless, for conciseness and clarity, the surgical procedures are described with reference to the multifunction surgical instrument 108 and the generator 500. The multifunction surgical instrument 108 comprises an end effector 125 which includes a clamp arm 145 and an ultrasonic blade 149. The end effector 125 may be configured with any of the structural or functional features of any one of the end effectors 122, 124, 125, 700, 800, 900, 1000, 1100, 1200, 2200, 2200', 2200", 2300 to provide electrodes to apply RF energy to tissue, temperature sensors, force/pressure sensors, and gap measurement sensors, as described hereinabove.

Techniques for Sealing or Sealing and Cutting Large Vessels and Tissue-Bundles In one aspect, the present disclosure provides a technique for sealing or sealing and cutting large vessels/tissue bundles by controlling the power delivered to an end effector from a generator, such as any one of the generators 102, 200, 300, 400, 500 (FIGS. 1-3 and 4-8), or a surgical instrument, such as the surgical instrument 108 (FIGS. 1-3). In accordance with the resent technique, the power delivered to an end effector of a surgical instrument can be varied based on the size of vessels and tissue bundles interacting with the end effector. For conciseness and clarity of disclosure, the techniques for sealing or sealing and cutting large vessels/tissue bundles will be described with reference to the multifunction surgical instrument 108 of FIG. 2 coupled to the generator 500 of FIG. 8, although it will be appreciated that other configurations of instruments, generators, and end effectors described herein may be readily substituted without departing from the scope of the present disclosure.

A technique for controlling the power output from a generator 500 that is delivered to the end effector 125 of a surgical instrument 108 can include an input that represents a state of coagulation of the tissue to allow the energy profile from the generator 500 to be dynamically changed during the tissue treatment process between RF and ultrasonic energy based on the state of coagulation of the tissue being treated by the end effector 125 of the surgical instrument 108 or the size of the vessels or tissue interacting with the end effector 108. This allows the processor 502 to control the generator 500 to switch from RF energy (ENERGY2/RETURN) when a tissue seal is complete to ultrasonic energy (ENERGY1/RETURN) to cut the tissue and complete a procedure. Also, this technique allows the generator 500 to switch to ultrasonic energy at the initial stages of treatment when either the vessel or tissue bundle is too large to seal with RF energy alone. Thus, ultrasonic energy is applied until the size of the vessel or tissue bundle is sufficiently reduced to enable the RF to complete a proper seal. It will be appreciated that the switch between a first form of energy and a second form of energy, and vice versa, can be done by first turning OFF the first form of energy and thereafter turning on the second form of energy. Alternatively, the switch between a first form of energy and a second form of energy, and vice versa, can be done by transitioning from the first form of energy to the second form of energy, and vice versa, such that for brief period both the first and second forms of energy are turned ON simultaneously while one form ramps up and the other ramps down. Thus, according to the latter approach, the RF and ultrasonic energies can be blended during the transition rather than "one then the other" approach.

In one aspect, the present disclosure provides techniques to improve the capability of the generator 500 to quickly and efficiently seal or seal and cut large vessels or large tissue bundles that present an initial extremely low impedance to the generator 500. These techniques shorten transaction times when sealing or sealing and cutting big tissue bundles that present low RF impedance to the generator 500. When RF energy is applied to tissue with real low impedance, due to electrical current capacity limitations (maximum output current capability) of the generator 500, the maximum power that can be delivered into tissue is limited, which results in very long transaction cycles. Note that the current limitation is not unique to the generators described herein and are applicable to other generators.

In one aspect, the state of coagulation of the tissue can be determined using a variety of techniques, In one aspect, the state of coagulation of the tissue is determined using a calculated tissue impedance and comparing it to a threshold to find the termination impedance, as explained above. The calculated tissue impedance, as described herein, is used by a technique to control the energy being delivered from the generator 500 to the surgical instrument 108.

In another aspect, the state of coagulation is determined using a "vector machine" or other techniques. In another aspect, the state of coagulation is determined using neural networks that are configured to take a plurality of factors into account. As discussed herein, a neural network refers to a series of techniques that attempt to identify underlying relationships in a set of data by using a process that mimics the way the human brain operates. Neural networks have the ability to adapt to changing input so that the network produces the best possible result without the need to redesign the output criteria. For example, the neural networks can take into account the tissue impedance as measured using the RF signal, the initial tissue impedance as measured using the RF signal, the energy that went into the transection, for example, in joules, the transection time, the initial aperture of the jaw, the current aperture of the jaw, and/or the rate of change of the tissue impedance. One example of a neural network 4700 for controlling a generator is described hereinbelow in connection with FIG. 73.

FIG. 45 is a logic flow diagram 2500 of one aspect of a process for sealing or sealing and cutting large vessels or large tissue bundles. As described herein, the logic flow diagram 2500 may be implemented in the generator 500, the multifunction surgical instrument 108, or a combination thereof. With reference now to the logic flow diagram 2500 shown in FIG. 45 and the surgical system 10 of FIG. 1, the state of coagulation of the tissue is determined as described herein. The generator 500 is configured to deliver RF energy (ENERGY2/RETURN) and ultrasonic energy (ENERGY1/RETURN) to switch between the RF and ultrasonic energy according to various techniques. The end effector 125 of the surgical instrument 108 is advanced and the tissue is clamped 2502 between the clamp arm 145 and the ultrasonic blade 149. The end effector 125 is activated with RF energy from the generator 500 and RF energy is delivered 2504 to the tissue to effect a seal employing a process such as a composite load curve (CLC) control process described in connection with the logic diagram 4600 shown FIG. 72. With reference back to FIG. 45, the processor 502 determines 2506 the state of coagulation to determine if a state of completion of coagulation of the tissue has been achieved, at which time the processor 502 signals the waveform generator 504 and amplifier 506 to switch from RF energy for coagulating tissue to ultrasonic energy for cutting tissue. If the desired tissue of coagulation or seal has not been achieved, the processor 502 continues along the NO branch and RF energy is continued to be delivered. When the proper state of coagulation has been reached, the processor 502 continues along the YES branch and the RF energy is switched 2508 to ultrasonic energy to cut the tissue. The tissue is released 2510 from the end effector 215 once the tissue cut is completed with the ultrasonic energy.

Also disclosed herein are techniques for dynamically changing the energy delivered from a generator based on end effector aperture. According to one aspect, a technique for controlling the power output from a generator, such as the generator 500 of FIG. 8, that is delivered to the end effector of a surgical instrument, such as surgical instrument 108 (FIGS. 1-3) can include an input that represents the aperture of the end effector 125 of the surgical instrument 108. The energy profile from the generator 500 can be dynamically changed during the procedure between RF and ultrasonic energy based on the size of the aperture defined by the end effector 125 clamping the tissue. This allows the generator 500 to switch from RF energy to ultrasonic energy based on the amount that the end effector 125 is clamping on the tissue being treated by the surgical instrument 108. The aperture of the clamp arm 145 is related to the creation of a proper coagulation seal, for example, when RF energy is delivered from the generator 500 to the end effector 125 of the surgical instrument 108, such that RF energy is used when there is sufficient closure of the end effector 125 on the tissue. Thus, if the aperture defined by the end effector is too large and there is insufficient clamp on the tissue for proper coagulation, only ultrasonic energy is delivered to the end effector 125.

For example, false information regarding various tissue measurements and/or characteristics can be transmitted to the generator 500 for controlling the energy delivered depending on the aperture defined by the end effector 125. One such measurement that can be affected by the aperture defined by the end effector 125 is tissue impedance. An incorrect tissue impedance determination can lead to early termination of a coagulation "sealing" cycle as the generator 500 may switch from RF to ultrasonic energy before a proper coagulation seal has been achieved.

The aperture defined by the end effector 125 can be determined using a variety of techniques. In one form, the aperture defined by the end effector 125 is determined by detecting the pivot angle of the end effector 125. This can be accomplished using a potentiometer, a Hall effect sensor, an optical encoder, an optical IR sensor, an inductance sensor, or a combination thereof. In another form, the proximity of first and second components of an end effector 125 is measured to determine the aperture defined by the end effector 125 using, for example, a Hall effect sensor, an optical IR, inductance sensor, or combination thereof. In another form, a surgical instrument 125 is configured to detect the aperture defined by the end effector 125 by measuring a change in a tissue impedance of the tissue interacting with the end effector 125. In another form, a surgical instrument is configured to detect the aperture defined by the end effector 125 by measuring a load applied by the end effector 125 on the tissue as ultrasonic energy is pulsed to the end effector 125. In another form, the surgical instrument includes a switch or other mechanism for closing the end effector 125 that can detect the aperture defined by the end effector 125. As previously discussed, the tissue impedance is determined by the processor 502 by dividing the voltage applied to the end effector 125 by the current delivered to the end effector 125. For example, the processor 502 can determine the tissue impedance by dividing the voltage sensed by the second voltage sensing circuit 524 by the current sensed by the current sensing circuit 514.

FIG. 46 is a logic flow diagram 2600 of one aspect of a process for sealing or sealing and cutting large vessels or large tissue bundles by dynamically changing energy being delivered from the generator 500 during the treatment of the tissue based on the changing aperture defined by the end effector. As described herein, the logic flow diagram 2600 may be implemented in the generator 500, the multifunction surgical instrument 108, or a combination thereof. With reference now to the logic flow diagram 2600 shown in FIG. 46, the processor 502 determines the aperture defined by the end effector 125 as described above. The processor 502 then determines the state of coagulation of the tissue as described herein. The generator 500 or the surgical instrument 108 may be configured to deliver RF energy (ENERGY2/RETURN) and ultrasonic energy (ENERGY1/RETURN) to switch between the RF and ultrasonic energy according to various techniques. The end effector 125 of the surgical instrument 108 is advanced and the tissue and the end effector 125 of the surgical instrument 108 is closed 2602 on tissue and the end effector 125 is activated with energy from the generator 500. The processor 502 determines 2604 the aperture defined by the end effector 125 using any of the techniques described above. The processor 502 signals the energy delivered from the generator 500 to the end effector 125 and controls when the generator 500 switches between RF and ultrasonic energy based on the aperture defined by the end effector 125. Accordingly, the processor 502 selects 2606 the generator 500 power delivery profile based on the aperture defined by the end effector 125. The processor 502 monitors 2608 the aperture defined by the end effector 125 during the tissue treatment process to dynamically change 2610 the energy delivered from the generator 500 during the tissue treatment process based on the changing aperture defined by the end effector 125.

In another aspect, a technique for controlling the power delivered from the generator 500 to the end effector 125 of the surgical instrument 108 can include an input that includes energy parameters based on an aperture of the end effector 125 of the surgical instrument 108. During the tissue treatment process, the processor 502 can dynamically change the energy output profile of the generator 500 between RF energy and ultrasonic energy using energy parameters based on the aperture defined by the end effector 125 clamping the tissue. This allows the generator 500 to switch from RF energy to ultrasonic energy based on how much clamping force the end effector is applying to the tissue during the treatment process. As explained above, the aperture of the clamp arm 145 is related to creating a proper coagulation seal. For example, RF energy should be delivered by the generator 500 to the end effector 125 only when there is sufficient closure of the end effector 125 on the tissue. Thus, when the aperture defined by the end effector 125 is too large and there is insufficient clamping force on the tissue for proper coagulation, only ultrasonic energy should be delivered to the end effector 125.

The aperture defined by the end effector 125 can be determined using any of the methods described above. For example, the surgical instrument 108 can include an aperture sensor in the end effector 125 that can be fed through a connector to the ASIC in the handle 109 of the surgical instrument 108. The surgical instrument 108 also can include a sensor in the handle 109 of the surgical instrument 108 that is configured to detect the aperture defined by the end effector 125.

Energy parameters are configured to be loaded into the generator 500, and can include a plurality of different parameters, including but not limited to voltage, current, power, and one or more techniques for use in treating tissue. These parameters can be related to the RF energy and ultrasonic energy that can be delivered from the generator 500. The energy parameters can include information such as maximum and/or minimum values to be used to control the energy delivered from the generator 500. The energy parameters can be stored in a variety of locations, including an EEPROM on the surgical instrument 108 or some other non-volatile memory. In addition, there can be multiple sets of energy parameters. For example, the processor 502 can use a first set of energy parameters to optimize tissue transection, and a second set of energy parameters to optimize tissue spot coagulation. It will be understood that there can be any number of set of energy parameters that correspond to various types of tissue treatments to allow the generator 500 to switch between the various sets of energy parameters based on the necessary tissue treatments.

When the end effector 125 of the surgical instrument 108 is activated, the processor 502 utilizes the various techniques described above to detect the aperture defined by the end effector 125. In one aspect, when the end effector 125 is closed around the tissue, the generator 500 can utilize the energy parameters for optimizing tissue transection. When the end effector 125 has a larger aperture and is not clamped on the tissue, the generator 500 can utilize the energy parameters for optimizing spot coagulation of the tissue.

FIG. 47 is a logic flow diagram 2700 of one aspect of a process for sealing or sealing and cutting large vessels or large tissue bundles by dynamically communicating energy parameters to the generator 500 during the tissue treatment process based on the changing aperture defined by the end effector 125 of the surgical instrument 108. As described herein, the logic flow diagram 2700 may be implemented in the generator 500, the multifunction surgical instrument 108, or a combination thereof. With reference now to the logic flow diagram 2700 shown in FIG. 47, the processor 502 determines the aperture defined by the end effector 125 as described above. The generator 500 is configured to deliver RF energy (ENERGY2/RETURN) and ultrasonic energy (ENERGY1/RETURN) and to switch between the RF and ultrasonic energy according to various techniques. The end effector 125 of the surgical instrument 108 is advanced, the end effector 125 of the surgical instrument 108 is closed 2702 on the tissue and the end effector 125 is activated with energy from the generator 500. The processor 502 determines 2704 the aperture defined by the end effector 125 using any of the techniques described above. The processor 502 signals the energy delivered from the generator 500 and to switch between RF and ultrasonic energy based on the aperture defined by the end effector 125 based on sets of energy parameters previously loaded into the generator 500. Accordingly, energy parameters are communicated 2706 to the generator 500 based on the measured aperture defined by the end effector 125. The aperture defined by the end effector 125 is monitored 2708 during the tissue treatment process such that the energy delivered from the generator 500 can be dynamically changed during the tissue treatment process based on the changing aperture defined by the end effector 125. Accordingly, the processor 502 dynamically communicates 2710 energy parameters to the generator 500 based on the measured aperture defined by the end effector 125. This allows the generator 500 to dynamically switch between various sets of energy parameters based on the changing aperture defined by the end effector 125.

It will be understood that various combinations of information can be used to determine which set of energy parameters are to be used during the tissue treatment process. For example, the aperture defined by the end effector 125 and calculated tissue impedance can be used by the processor 502 to determine which set of energy parameters are needed to control the energy being delivered from the generator 500. As previously discussed, the tissue impedance is determined by the processor 502 by dividing the voltage applied to the end effector 125 by the current delivered to the end effector 125. For example, the processor 502 can determine the tissue impedance by dividing the voltage sensed by the second voltage sensing circuit 524 by the current sensed by the current sensing circuit 514.

In another aspect, a technique for controlling the power output from the generator 500 and delivered to the end effector 125 of the surgical instrument 108 can include an input that includes inputs related to the size of the tissue being treated by the end effector 125 of the surgical instrument 108. During the tissue treatment process, the processor 502 dynamically changes the energy delivered from the generator 500 between RF energy and ultrasonic energy to achieve dissection and coagulation of large vessels and large tissue bundles based on a determination of the effectiveness of the RF energy in coagulating the large vessels or large tissue bundles. A determination of the effectiveness of the RF energy in coagulating a tissue includes a calculation of tissue impedance, as explained above, of the large tissue interacting with the end effector 125, which is used to determine the type of energy delivered by the generator 500 to the end effector 125.

FIG. 48 is a logic flow diagram 2800 of a technique to seal or seal and cut vessels using RF and ultrasonic energy in conjunction with tissue impedance measurements and the aperture defined by the clamp arm measurements. As described herein, the logic flow diagram 2800 may be implemented in the generator 500, the multifunction surgical instrument 108, or a combination thereof. With reference now to the logic flow diagram 2800 shown in FIG. 48, the end effector 125 is advanced and the clamp arm 145 is closed 2802 on tissue located between the clamp arm 145 and the ultrasonic blade 149 of the end effector 125. The end effector 125 is then activated with RF energy (ENERGY2/RETURN) from the generator 500 to form a seal. The processor 502 determines 2804 the tissue impedance and the aperture defined by the end effector 125 as described herein. As previously discussed, the tissue impedance is determined by the processor 502 by dividing the voltage applied to the end effector 125 by the current delivered to the end effector 125. For example, the processor 502 can determine the tissue impedance by dividing the voltage sensed by the second voltage sensing circuit 524 by the current sensed by the current sensing circuit 514.

The aperture defined by the end effector 125 and the processor 502 determines 2804 the tissue impedance using any of the techniques described herein. The processor 502 compares 2806 the tissue impedance values to stored threshold values and determines 2808 whether or not these values are greater than the threshold values. If either the tissue impedance or the aperture defined by the end effector 125 is less than the threshold value, the processor 502 continuous along the NO branch and RF energy (ENERGY2/RETURN) continues to be delivered from the generator 500 to the end effector 125. If the tissue impedance and the aperture defined by the end effector 125 are greater than the threshold value, the processor 502 continues along the YES branch and switches 2810 to delivering ultrasonic energy (ENERGY1/RETURN) from the generator 500. This allows the large vessels and large tissue bundles to be reduced in size or shrunk with ultrasonic energy to a size that would allow the RF energy to form a more optimal seal.

The processor 502 determines 2812 the aperture defined by the end effector 125 using any of the techniques described herein. The processor 502 then compares 2814 these aperture values to stored threshold aperture values and determines whether or not these aperture values represent that the tissue has been shrunk by the ultrasonic energy to a size that would allow the RF energy to properly seal the tissue. If the processor 502 determines that tissue is too large for RF energy sealing, the processor 502 continues along the NO branch and ultrasonic energy continues to be delivered from the generator 500 to the end effector 125 to continue shrinking the tissue. If the processor 502 determines that the tissue is has been shrunk to an appropriate size suitable for sealing with RF energy, the processor 502 continues along the YES branch and switches 2816 the energy delivered from the generator 500 to RF energy. The processor 502 signals can optionally switch back 2818 to delivering ultrasonic energy upon determining that the RF energy has completed the tissue seal.

FIG. 49 is a logic flow diagram 2900 of one aspect of a process for sealing or sealing and cutting large vessels or large tissue bundles. As described herein, the logic flow diagram 2900 may be implemented in the generator 500, the multifunction surgical instrument 108, or a combination thereof. With reference now to the logic flow diagram 2900 shown in FIG. 49, tissue is initially grasped 2902 by the end effector 125 between the clamp arm 145 and the ultrasonic blade 149. RF energy (ENERGY2/RETURN) is delivered 2904 to the end effector 125. The processor 502 monitors 2906 the tissue impedance $Z_T$ and jaw aperture $A_j$ for a predetermined period $T_o$, which may be selected from a range of 0.5 to 2.0 seconds, and preferably about 1.5 seconds, for example. As previously discussed, the tissue impedance is determined by the processor 502 by dividing the voltage applied to the end effector 125 by the current delivered to the end effector 125. For example, the processor 502 can determine the tissue impedance by dividing the voltage sensed by the second voltage sensing circuit 524 by the current sensed by the current sensing circuit 514.

Until the predetermined period $T_o$ elapses 2908, the processor 502 continues along the NO branch and the generator 500 continues to deliver RF energy and the processor 502 continues to monitor (measure) tissue impedance $Z_T$ and jaw aperture $A_j$. At the end of the time period $T_o$, if tissue impedance $Z_T$ has not increased to a value equal to or greater than a predetermined threshold and the jaw aperture is equal to or less than a predetermined threshold, the processor 502 proceeds along the YES branch and switches 2910 the generator 500 to ultrasonic energy mode. Ultrasonic energy is delivered 2912 to the tissue while the processor 502 monitors the tissue impedance $Z_T$ and jaw aperture $A_j$ until the tissue shrinks to a size that is suitable for sealing with RF energy. The processor 502 compares 2914 the jaw aperture $A_j$ to a threshold jaw aperture and if it is less than or equal to the threshold the processor 502 continues along the YES branch assuming that the tissue is sized for sealing by RF energy. The processor 502 switches the generator 500 to RF energy mode and delivers 2916 RF energy to complete the seal while the processor 502 monitors the tissue impedance $Z_T$ to determine 2918 if the seal is complete. If the seal is complete and seal-only is desired, the processor 502 completes 2920 the operation. If the seal is complete and seal and cut is desired, the processor 502 switches the generator 500 to ultrasonic energy mode and delivers 2922 ultrasonic energy to cut the sealed tissue. Upon cutting the tissue, the processor 502 completes 2920 the operation.

FIG. 50 is a logic flow diagram 3000 of a technique to seal or seal and cut vessels using RF and ultrasonic energy in conjunction with tissue impedance measurements. As described herein, the logic flow diagram 3000 may be implemented in the generator 500, the multifunction surgical instrument 108, or a combination thereof. With reference now to the logic flow diagram 3000 shown in FIG. 50, tissue is clamped between the clamp arm 145 and the ultrasonic blade 149 of the end effector 125 of the surgical instrument 108. The processor 502 signals the waveform generator 504 and amplifier 506 to deliver 3002 RF energy (ENERGY2/RETURN) to the end effector 125 of the surgical instrument 108 interacting with tissue to create a tissue seal using the RF energy. The processor 502 calculates 3004 a first tissue impedance $Z_{T1}$ of the tissue interacting with the end effector 125 at the start of the period $T_o$ of the delivery of the RF energy and then calculates 3006 a second tissue impedance $Z_{T2}$ of the tissue interacting with the end effector after the RF energy is delivered for a predetermined period $T_1$. As previously discussed, the tissue impedance is determined by the processor 502 by dividing the voltage applied to the end effector 125 by the current delivered to the end effector 125. For example, the processor 502 can determine the tissue impedance by dividing the voltage sensed by the second voltage sensing circuit 524 by the current sensed by the current sensing circuit 514.

The processor 502 compares $Z_{T1}$ to $Z_{T2}$. If $Z_{T2}$ is less than or equal to $Z_{T1}$ after RF energy is delivered for a period of $T_1$, there may be a short circuit or the tissue impedance is too low for RF energy to deliver power to the tissue. Accordingly, the processor 502 proceeds along the YES branch and controls the waveform generator 504 and amplifier 506 to stop 3010 delivering RF energy to the end effector 125 and start delivering 3012 ultrasonic energy to the end effector 125 until $Z_{T2}$ is greater than $Z_{T1}$. Once $Z_{T2}$ exceeds $Z_{T1}$, the processor 502 continues along the NO branch and controls the waveform generator 504 and amplifier 506 to continue 3014 delivering RF energy to the end effector 125 until the tissue is sealed 3016. Once the tissue is sealed, the processor 502 continues along the YES branch and the controls the waveform generator 504 and amplifier 506 to stop delivering RF energy to the end effector 125 and to start delivering 3020 ultrasonic energy to cut the tissue. If the tissue is not sealed, the processor 502 continues along the NO branch and the generator 500 continues delivering RF energy to the end effector until the tissue seal is completed.

In another aspect, a technique for controlling the power output from the generator 500 delivered to the end effector 125 of the surgical instrument 108 can include an input that includes inputs related to the size of the tissue being treated by the end effector 125 of the surgical instrument 108. The energy delivered from the generator 500 can be dynamically changed during the procedure between RF and ultrasonic energy to achieve dissection and coagulation of a large tissue based on a determination of the effectiveness of the RF energy in coagulating the large tissue. A determination of the effectiveness of the RF energy in coagulating a tissue includes a calculation of tissue impedance, as explained above, of the large tissue interacting with the end effector 125, which is used to determine the type of energy being delivered by the generator 500 to the end effector 125.

FIG. 51 is a logic flow diagram 3100 of a technique to seal or seal and cut vessels using RF and ultrasonic energy in conjunction with tissue impedance measurements and the aperture defined by the clamp jaw measurements. As described herein, the logic flow diagram 3100 may be implemented in the generator 500, the multifunction surgical instrument 108, or a combination thereof. With reference now to the logic flow diagram 3100 shown in FIG. 51, tissue is clamped between the clamp arm 145 and the ultrasonic blade 149 of the end effector 125 of the surgical instrument 108. The processor 502 signals the waveform generator 504 and amplifier 506 to deliver 3102 RF energy (ENERGY2/RETURN) to the end effector 125 of the surgical instrument 108 interacting with tissue to create a tissue seal using the RF energy. The processor 502 calculates 3104 a first tissue impedance $Z_{T1}$ of the tissue interacting with the end effector 125 at the start of a period $T_o$ of delivery of the RF energy and then calculates 3106 a second tissue impedance $Z_{T2}$ of the tissue interacting with the end effector 125 after the RF energy is delivered for a predetermined period $T_1$ and measures the aperture $A_j$ defined by the clamp arm 145. As previously discussed, the tissue impedance is determined by the processor 502 by dividing the voltage applied to the end effector 125 by the current delivered to the end effector 125. For example, the processor 502 can determine the tissue impedance by dividing the voltage sensed by the second voltage sensing circuit 524 by the current sensed by the current sensing circuit 514.

The processor 502 compares $Z_{T1}$ to $Z_{T2}$. If $Z_{T2}$ is less than or equal to $Z_{T1}$ after RF energy is delivered for a period of $T_1$, the processor 502 determines that there may be a short circuit or extremely low the tissue impedance present at the end effector 125 that is too low for RF energy to deliver any power to the tissue. Accordingly, the processor 502 proceeds along the YES branch and the generator 500 and compares the measured aperture $A_j$ defined by the clamp arm 145 to a predetermined threshold aperture $A_{jo}$ defined by the clamp arm 145, where the predetermined threshold aperture $A_{jo}$ d corresponds to a thick vessel or a thick tissue bundle located between the clamp arm 145 and the ultrasonic blade 149. If the measured aperture $A_j$ defined by the clamp arm 145 is less than or equal to the predetermined threshold aperture $A_{jo}$, the processor 502 continues along the NO branch and controls the waveform generator 504 and amplifier 506 to continue delivering RF energy to the end effector 125 until the tissue impedance $Z_{T2}$ is less than the initial tissue impedance $Z_{T1}$. If the measured aperture $A_j$ defined by the clamp arm 145 is greater than the predetermined threshold aperture $A_{jo}$, the processor 502 continues along the YES branch and controls the generator to stop 3110 delivering RF energy to the end effector 125 and start delivering 3112 ultrasonic energy (ENERGY1/RETURN) to the end effector 125 until $Z_{T2}$ is greater than $Z_{T1}$. Once $Z_{T2}$ is greater than $Z_{T1}$, the processor 502 continues along the NO branch and controls the waveform generator 504 and amplifier 506 to continue 3114 delivering RF energy to the end effector 125 until the tissue is sealed 3116. Once the tissue is sealed, the processor 502 continues along the YES branch and controls the waveform generator 504 and amplifier 506 to stop delivering RF energy and start delivering 3120 ultrasonic energy to the end effector 125 to cut the tissue. If the tissue is not sealed, the processor 502 continues along the NO branch and controls the waveform generator 504 and amplifier 506 to continue delivering RF energy to the end effector 125 until the tissue seal is complete.

Techniques for Switching Between RF and Ultrasonic Energy Based on the State of Coagulation of Tissue In one aspect, the present disclosure provides a technique for switching between RF and ultrasonic energy based on the state of coagulation of tissue by controlling the power delivered to an end effector from a generator, such as any one of the generators 102, 200, 300, 400, 500 (FIGS. 1-3 and 4-8), or a surgical instrument, such as the surgical instrument 108 (FIGS. 1-3). In accordance with the present technique, the power delivered to an end effector of a surgical instrument can be switched between RF and ultrasonic based on the state of coagulation of tissue interacting with the end effector. For conciseness and clarity of disclosure, the techniques for switching between RF and ultrasonic energy based on the state of coagulation of tissue will be described with reference to the multifunction surgical instrument 108 of FIG. 2 coupled to the generator 500 of FIG. 8, although it will be appreciated that other configurations of instruments, generators, and end effectors described herein may be readily substituted without departing from the scope of the present disclosure.

To address these issues, in some aspects, a generator 500 capable of handling both ultrasonic and RF electrosurgical systems may include a completely nested neural network to identify whether the generator 500 is presented with a true short circuit vs. a low impedance tissue. In addition, in some aspects, to assist in the detection of short circuits, the neural network may be configured to track and store at least the following factors: a. Measured resistance/impedance; b. Drive current (RMS); c. Drive Voltage (RMS); and d. Moving average of measured impedance. In some aspects, the neural network will be thought to in order to be capable of discerning between a true short and low impedance tissue.

Furthermore, in some aspects, methods for detecting a short circuit may utilize the ultrasonic functionality to cut low impedance tissue and to identify a true short circuit. For example, instead of faulting, the generator 500 may send in an exploratory pulse to the ultrasonic transducer 120. The tissue properties initially assessed by the ultrasonic blade 149 touching a metal short would result in a higher output drive voltage and resulting impedance. This level of impedance may be measured to determine whether the material was actually metal versus low impedance tissue. If the processor 502 determines that metal is not present in the end effector 125, the generator 500 continues to deliver ultrasonic energy to the end effector 125 and cut through the load. Thus, if the impedance is too low for the application of RF energy to seal the tissue in a timely manner, ultrasonic energy could be applied cut through non-metal low impedances without difficulty.

FIG. 52 is a logic flow diagram 3200 of one aspect of a technique for distinguishing a short circuit from low impedance tissue while utilizing RF energy by measuring voltage properties of an exploratory ultrasonic pulse. As described herein, the logic flow diagram 3200 may be implemented in the generator 500, the multifunction surgical instrument 108, or a combination thereof. With reference now to FIG. 52, the logic flow diagram 3200 provides a method for distinguishing a short circuit from low impedance tissue. With reference to the surgical instrument 108 of FIG. 2 coupled to the generator 500 of FIG. 8, tissue is clamped between the clamp arm 145 and the ultrasonic blade 149 of the end effector 125 of the surgical instrument 108. In accordance with the method, the processor 502 signals the waveform generator 504 and amplifier 506 to transition 3202 from delivering RF energy (ENERGY2/RETURN) to delivering ultrasonic energy (ENERGY1/RETURN). The processor 502 then controls the waveform generator 504 and amplifier 506 to transmit 3204 an exploratory pulse to the ultrasonic transducer 120 to apply ultrasonic energy to the short circuit area in question. The processor 502 then measures 3206 the output drive voltage and drive current and determines the impedance. As previously discussed, the tissue impedance is determined by the processor 502 by dividing the voltage applied to the end effector 125 by the current delivered to the end effector 125. For example, the processor 502 can determine the tissue impedance by dividing the voltage sensed by the second voltage sensing circuit 524 by the current sensed by the current sensing circuit 514. At this juncture, the processor 502 determines 3208 whether the impedance is consistent with low impedance tissue. When the impedance is consistent with low impedance tissue, the processor 502 proceeds along the YES branch and controls the waveform generator 504 and amplifier 506 to continue 3210 delivering ultrasonic energy to cut through tissue. When the impedance is not consistent with low impedance tissue, the processor 502 proceeds along the NO branch and controls the waveform generator 504 and amplifier 506 to stop 3212 the application of ultrasonic energy.

Additionally, in some aspects, if a short is detected while in RF mode and delivering RF energy to the end effector 125, the processor 502 signals the waveform generator 504 and amplifier 506 to transmit an ultrasonic pulse to the ultrasonic transducer 120. A microphone and ultrasonic application can be configured to detect the sound of characteristic ultrasonic vibrations against metal, since it would be very apparent and instantly or easily recognizable. Using knowledge in acoustics and waveform engineering, the processor 502 can account for what frequencies are heard due to the ultrasonic blade 149 acting on metal and on other non-tissue materials.

FIG. 53 is a logic flow diagram 3300 of a technique for distinguishing a short circuit from low impedance tissue while delivering RF energy and measuring acoustic properties of an exploratory ultrasonic pulse, according to some aspects. As described herein, the logic flow diagram 3300 may be implemented in the generator 500, the multifunction surgical instrument 108, or a combination thereof. With reference now to FIG. 53, the logic flow diagram 3300 provides a method for distinguishing a short circuit from low impedance tissue. The tissue is clamped between the clamp arm 145 and the ultrasonic blade 149 of the end effector 125 of the surgical instrument 108. In accordance with the method, the processor 502 signals the waveform generator 504 and amplifier 506 to transition 3302 from delivering RF energy (ENERGY2/RETURN) to delivering ultrasonic energy (ENERGY1/RETURN). The processor 502 then controls the waveform generator 504 and amplifier 506 to transmit 3304 an exploratory pulse to the ultrasonic transducer 120 to apply ultrasonic energy to the short circuit area in question. The processor 502 measures 3306 the acoustic properties of the area in question based on applied ultrasonic vibrations. At this juncture, the processor 502 determines 3308 whether the acoustic properties are consistent with the low impedance tissue. When the processor 502 determines acoustic properties are consistent with low impedance tissue, the processor 502 proceeds along the YES branch and controls the waveform generator 504 and amplifier 506 to continue 3210 delivering ultrasonic energy to cut through tissue. When the processor 502 determines that the acoustic properties are consistent with low impedance tissue, the processor 502 proceeds along the NO branch and controls the waveform generator 504 and amplifier 506 to stop 3312 delivering ultrasonic energy.

In some aspects, a neural network, such as neural network 4700 for controlling a generator shown in FIG. 73, may be programmed to identify these properties in metal, tissues, and other non-tissue materials. The neural network also may be configured to transmit the exploratory pulse to the ultrasonic transducer. In addition, new developments or additional programs, including receiving feedback from the attempts to detect short circuits, may be incorporated back into the neural network to increase its situational awareness and effectively better learn how to detect a true short circuit. With confirmation of a short circuit both by RF and ultrasonic functionality, this can allow for less time spent getting repeat errors on RF and faster transection on low impedance tissue.

Also disclosed herein are techniques for combining RF energy and ultrasonic energy to seal tissue without cutting. In some aspects, the surgical system including the generator of the present disclosures may be configured to implement a method for sealing tissue at a surgical site without cutting, by using a combination of ultrasonic energy and RF energy. In some aspects, the method includes superimposing the ultrasonic drive signal together with a fixed low RF signal (e.g., ultrasonic at 55.5 KHz and RF at 330 KHz). For example, during a sealing procedure, the ultrasonic drive signal may be configured to dynamically change in order to: (1) track the resonance of the ultrasonic drive signal, and (2) provide the desired strength or amplitude of vibrations in order to achieve the desired tissue effect. The fixed low RF signal will be provided in order to measure the tissue impedance and modify the ultrasonic drive to achieve the desired seal without cutting.

The RF signal may be superimposed in several non-exhaustive ways. In one way, the RF drive signal may be superimpose on top of the ultrasonic drive signal in a continuous fashion. In another way, the ultrasonic drive signal may be time sliced in such way that periodically or aperiodically, e.g., every 250 mSec, the ultrasonic drive signal will cease and a short burst of the RF drive signal of, e.g., 50 mSec, will be driving the output at a sub-therapeutic level which will still be sufficient to measure tissue impedance. After this burst, the processor 502 will control the waveform generator 504 and the amplifier 506 to switch the output of the generator 500 back to delivering the ultrasonic drive signal. The overall control loop may be configured to monitor the RF tissue impedance and adjust the ultrasonic drive signal output to achieve a tissue seal without cutting the tissue.

FIG. 54 is a logic flow diagram 3400 of a technique for conducting a tissue sealing technique without cutting by using a combination of ultrasonic energy and RF energy, according to some aspects. As described herein, the logic flow diagram 3400 may be implemented in the generator 500, the multifunction surgical instrument 108, or a combination thereof. With reference now to FIG. 54, the logic flow diagram 3400 provides an example iterative technique for cyclically combining RF energy (ENERGY2/RETURN) and ultrasonic energy (ENERGY1/RETURN) to seal tissue without cutting, according to some aspects. Tissue is clamped between the clamp arm 145 and the ultrasonic blade 149 of the end effector 125 of the surgical instrument 108. In accordance with the method, the processor 502 signals the waveform generator 504 to deliver 3402 an ultrasonic drive signal during a first interval of time to seal tissue at a surgical site. The processor 502 then controls the waveform generator 504 and the amplifier 506 to cease 3404 the ultrasonic drive signal after the first interval. The processor 502 then controls the waveform generator 504 and the amplifier 506 to deliver an RF drive signal at a sub-therapeutic amplitude during a second interval of time to measure tissue impedance. The processor 502 then controls the waveform generator 504 and the amplifier 506 to cease 3408 the RF drive signal after the second interval of time. The processor 502 then adjusts 3410 an ultrasonic drive signal based on the measured impedance from the RF drive signal. The processor 502 repeats 3412 the procedure until the surgical site is sealed.

The input to this control system to reduce/modify the ultrasonic drive signal and at eventually completely terminate the ultrasonic drive signal can utilize the following non-exhaustive methods: follow a power reduction and termination technique based on regular logic, fuzzy logic, vector machine, or neural network utilizing the following example: initial tissue impedance, initial jaws-aperture, current tissue impedance, rate of change of tissue impedance, energy driven into tissue, and transection time.

In some aspects, the surgical system may be configured to measure these terms through one or more sensors. Example methods for monitoring these terms and the ultrasonic functionality of the combination RF and ultrasonic surgical system may be based on methods described in U.S. Pat. No. 9,017,326, titled "Impedance Monitoring Apparatus, System, And Method For Ultrasonic Surgical Instruments," which is hereby incorporated by reference in its entirety.

FIG. 55 is a logic flow diagram 3500 of a technique for conducting a tissue sealing technique without cutting by using a combination of ultrasonic energy and RF energy, according to some aspects. As described herein, the logic flow diagram 3500 may be implemented in the generator 500, the multifunction surgical instrument 108, or a combination thereof. With reference now to FIG. 55, the logic flow diagram 3500 provides an example iterative technique for cyclically combining RF energy (ENERGY2/RETURN) and ultrasonic energy (ENERGY1/RETURN) to seal tissue without cutting, according to some aspects. Tissue is clamped between the clamp arm 145 and the ultrasonic blade 149 of the end effector 125 of the surgical instrument 108. In accordance with the method, the processor 502 signals the waveform generator 504 to deliver 3502 an ultrasonic drive signal to the tissue during a first interval of time $T_1$. The processor 502 then controls the waveform generator 504 and the amplifier 506 to cease 3504 the ultrasonic drive signal after the first interval $T_1$. The processor 502 then controls the waveform generator 504 and the amplifier 506 to deliver 3506 an RF drive signal at a sub-therapeutic amplitude during a second interval $T_1$ of time to measure the tissue impedance. The processor 502 then controls the waveform generator 504 and the amplifier 506 to cease 3508 the RF drive signal after the second time interval $T_2$. The processor 502 then controls the waveform generator 504 and the amplifier 506 to iteratively adjust 3510 the ultrasonic drive signal based on the measured tissue impedance until the processor 502 determines that the tissue is sealed. As previously discussed, the tissue impedance is determined by the processor 502 by dividing the voltage applied to the end effector 125 by the current delivered to the end effector 125. For example, the processor 502 can determine the tissue impedance by dividing the voltage sensed by the second voltage sensing circuit 524 by the current sensed by the current sensing circuit 514.

Techniques for Improving Short Circuit Detection in a Combination Ultrasonic/RF Surgical Instrument In one aspect, the present disclosure provides a technique for detecting extremely low impedances or actual short circuits in the end effector by controlling the power delivered to an end effector from a generator, such as any one of the generators 102, 200, 300, 400, 500 (FIGS. 1-3 and 4-8), or a surgical instrument, such as the surgical instrument 108 (FIGS. 1-3). In accordance with the present technique, the power delivered to an end effector of a surgical instrument can be varied based on whether a very low impedance or actual short circuit condition is present at the end effector. For conciseness and clarity of disclosure, the techniques for detecting extremely low impedances or actual short circuits in the end effector will be described with reference to the multifunction surgical instrument 108 of FIG. 2 coupled to the generator 500 of FIG. 8, although it will be appreciated that other configurations of instruments, generators, and end effectors described herein may be readily substituted without departing from the scope of the present disclosure.

Disclosed herein are techniques for detecting short circuits, including implementing detection methods in a neural network. In some aspects, the ultrasonic generator 500 of the present disclosures includes components configured to accurately and reliably detect short circuits. Particularly when performing surgeries on body tissue typical with use of the end effectors described herein, detecting a short circuit can be difficult for a number of reasons. For example, many times tissue presents itself as a short circuit, thereby fooling the detection software and at low signal magnitudes, which are inherent when driving signals with a short circuit, the measurement(s) error(s) is/are substantial and can result in making the wrong decision whether the generator is presented with a true short circuit. In addition, in some aspects of the generator described herein, low impedance tissue or metal shorts cause the generator to fault while in RF mode. In general, it may be difficult for the generator to distinguish between low impedance tissue and metal, where one may result in a true short circuit while the other is merely based on low impedance tissue.

FIG. 56 is logic flow diagram 3600 of a technique for detecting low impedance tissue or metal shorts that may cause false short circuits in RF mode. As described herein, the logic flow diagram 3600 may be implemented in the generator 500, the multifunction surgical instrument 108, or a combination thereof. With reference now to FIG. 56, the logic flow diagram 3600 provides an example technique for detecting low impedance tissue or metal shorts that may cause false short circuits in RF mode. Tissue is clamped between the clamp arm 145 and the ultrasonic blade 149 of the end effector 125 of the surgical instrument 108. In accordance with the method, if the processor 502 cannot distinguish low impedance tissue from metal located between the clamp arm 145 and the ultrasonic blade 149 of the end effector 125, the processor 502 signals the waveform generator 504 to deliver ultrasonic energy (ENRGY1/RETURN) to cut low impedance tissue and to identify a true short circuit, such as metal to metal contact between the clamp arm 145 and the ultrasonic blade 149. In accordance with the method, the processor 502 signals the waveform generator 504 to deliver 3602 RF energy (ENERGY2/RETURN) with the end effector 125 to the target surgical site. The processor 502 then controls the waveform generator 504 and the amplifier 506 to transition 3604 from delivering RF energy to delivering ultrasonic energy to the end effector 125. The processor 502 signals the waveform generator 504 to transmit 3606 an exploratory ultrasonic pulse to the end effector 125 and then measures 3608 an ultrasonic property of the ultrasonic pulse upon transmission to the end effector 125.

Techniques for Delivering Pulsed RF and Ultrasonic Energy in a Combination Ultrasonic/RF Surgical Instrument In one aspect, the present disclosure provides a technique for delivering RF and ultrasonic energy to an end effector of a surgical instrument by controlling the power delivered to an end effector from a generator, such as any one of the generators 102, 200, 300, 400, 500 (FIGS. 1-3 and 4-8), or a surgical instrument, such as the surgical instrument 108 (FIGS. 1-3). In accordance with the present technique, the power delivered to an end effector of a surgical instrument can be varied based on properties or parameters of tissue interacting with the end effector. For conciseness and clarity of disclosure, the techniques for delivering RF and ultrasonic energy to the end effector will be described with reference to the multifunction surgical instrument 108 of FIG. 2 coupled to the generator 500 of FIG. 8, although it will be appreciated that other configurations of instruments, generators, and end effectors described herein may be readily substituted without departing from the scope of the present disclosure.

FIGS. 57-66 illustrate aspects of timing diagrams of energy pulses for delivering different energy modalities to tissue. In one aspect the first energy modality is RF energy and the second energy modality is ultrasonic energy. There are many benefits to a surgical device that is capable of delivering both RF and ultrasonic energy. A surgical instrument capable of delivering both modalities provides stronger seals and can cut tissue without the need of a separate knife. The following disclosure provides multiple pulsing techniques than can be utilized for vessel sealing. These techniques employ tissue impedance measurements, current measurements, can seal only, and can seal and cut tissue. These techniques may be implemented using multiple generators, one generator configured to deliver RF energy and another generator configured to deliver ultrasonic energy. Alternatively, these techniques may be implemented with a single generator configured to deliver both RF and ultrasonic energy. In other aspects, these techniques may be implemented with a single generator that is configured to deliver RF and ultrasonic energy simultaneously through a single output port.

These techniques comprise pulsing between RF and ultrasonic energy modalities to create strong seals. Multiple configurations of pulsing are disclosed. The pulse sequence timing diagrams illustrated in FIGS. 57-63 and the logic flow diagrams shown in FIGS. 64-66 will be described with reference to the surgical instrument 108 of FIG. 2 coupled to the generator 500 of FIG. 8. Tissue is clamped between the clamp arm 145 and the ultrasonic blade 149 of the end effector 125 of the surgical instrument 108 and then the generator 500 delivers the pulse sequences discussed below.

FIG. 57 is a timing diagram of a seal only pulse sequence 3700 illustrating a basic configuration of pulsing RF and ultrasonic energy for "Seal Only" mode. The horizontal axis is time (t) in seconds that the energy is delivered or "pulsed." The vertical axis is the current pulse amplitude in milliamps (mA) that the pulse is capable of sourcing. The ultrasonic energy pulses 3702 are shown in dashed line and the RF pulses 3704 are shown in solid line. As shown in FIG. 57, the generator 500 switches between the ultrasonic energy pulses 3702 and RF energy pulses 3704 at fixed time intervals. During a first half cycle, the pulse sequence starts with the RF energy pulse 3704 ON for about 1 mS at a current pulse of about 750 mA amplitude while the ultrasonic energy pulse 3702 is OFF for about 1 mS at 0 mA current amplitude. During the next half cycle, the RF energy pulse 3704 is OFF for about 1 mS at 0 mA current amplitude while ultrasonic energy pulse 3702 is ON for about 1 ms at a current pulse of about 350 mA amplitude. The cycle is repeated until a strong tissue seal is developed. It will be appreciated that the application of the sequence of ultrasonic energy pulses 3702 and RF energy pulses 3704 shown in the pulse sequence 3700 is suitable for effecting a tissue seal only. This configuration of pulse sequence can start either with an RF energy pulse 3704 or an ultrasonic energy pulse 3702. Ultimately energy delivery for a "Seal Only" mode would be stopped based on the tissue impedance measured on the RF pulses 3704.

In order to reduce the risk of cutting tissue with the ultrasonic energy pulses 3702, the number of ultrasonic energy pulses 3702 should be minimized. This configuration is shown in FIG. 58, which is a timing diagram of a seal only pulse sequence 3710 illustrating a basic configuration of pulsing RF and ultrasonic energy for "Seal Only" mode. As shown, the pulse sequence 3700 starts with an active RF energy pulse 3704. After two ultrasonic energy pulses 3702, or other predetermined limited number of ultrasonic energy pulses 3702, no more ultrasonic energy pulses 3702 are delivered after the last ultrasonic energy pulse 3702' and the RF energy pulse 3704' is delivered for an extended period to effect a seal only. To avoid cutting the tissue with the ultrasonic energy pulse 3704 the last RF energy pulse 3704' remains ON at high amplitude while the ultrasonic energy pulse 3702 remains OFF.

It can be appreciated that the seal on the clamp arm 145 side may be wider and more complete than a seal on the ultrasonic blade 149 side. This may be caused by insufficient heating on the ultrasonic blade 149 side due to the higher thermal mass of the ultrasonic blade 149. In order to address this issue, the ultrasonic energy pulse 3702 could be left ON longer at the beginning to get the ultrasonic blade 149 up to the sealing temperature. FIG. 59 is a timing diagram of a seal only pulse sequence 3720 illustrating a basic configuration of pulsing RF and ultrasonic energy to preheat the ultrasonic blade 149. FIG. 59 is a timing diagram of a seal only pulse sequence 3720. As shown in FIG. 59, the first energy pulse delivered is an ultrasonic energy pulse 3702, which is left ON for an extended period sufficient to preheat the ultrasonic blade 149 prior to applying the RF energy pulses 3704. To avoid cutting the tissue with the ultrasonic energy pulse 3704 the last RF energy pulse 3704' remains ON at high amplitude while the ultrasonic energy pulse 3702 remains OFF.

FIG. 60 is a timing diagram of a seal only pulse sequence 3730. One of the main benefits to having more than one pulse of ultrasonic energy 3702 is to maintain the ultrasonic blade 149 temperature. In order to maintain ultrasonic blade 149 temperature and reduce the risk of cutting tissue with the ultrasonic blade 149, the pulse sequence 3730 shown in FIG. 60 provides the first ultrasonic energy pulse 3702 at a high amplitude and then the subsequent ultrasonic energy pulses 3702', 3702" at lower amplitudes. To avoid cutting the tissue with the ultrasonic energy pulse 3704 the last RF energy pulse 3704' remains ON at high amplitude while the ultrasonic energy pulse 3702 remains OFF.

The conditions for switching between the RF energy pulse 3704 and the ultrasonic energy pulse 3702 could be based on a fixed time or it could be based on tissue impedance. For example, when a "Seal Only" mode is desired, as shown in FIGS. 57-60, if a certain Impedance threshold is reached, the technique would not switch over to ultrasonic energy to minimize the risk of cutting through the tissue. The frequency slope could also be used as a trigger to switch from ultrasonic energy pulse 3702 delivery to RF energy pulse 3704 delivery.

If a "Seal and Cut" energy modality is desired, an ultrasonic energy pulse 3702 step could be added to the end of any of the techniques described in connection with FIGS. 57-60. This could occur once a certain impedance threshold is met. FIGS. 61 and 62 illustrate timing diagrams for seal and cut pulse sequences 3740, 3750 for issue seal and cut modes.

FIG. 61 is a timing diagram of a seal and cut pulse sequence 3740, which begins and ends with ultrasonic energy pulses 3702 delivered at the same amplitude during the sealing a cutting cycles. A first ultrasonic energy pulse 3702 is delivered at a predetermined amplitude and subsequent ultrasonic energy pulses 3702 are delivered at the same predetermined amplitude. The RF energy pulses 3704 are delivered until the tissue is sealed or until the tissue impedance is equal to or greater than a predetermined threshold. After the last delivered RF energy pulse 3704' is turned OFF, the last ultrasonic energy pulse 3702' is turned ON to cut tissue.

FIG. 62 is a timing diagram of a seal and cut pulse sequence 3750, which begins and ends with ultrasonic energy pulses 3702 delivered at variable amplitude during the sealing a cutting cycles. A first ultrasonic energy pulse 3702 is delivered at a predetermined amplitude and subsequent ultrasonic energy pulses 3702 are delivered at different amplitudes, and in one example as a stepped down amplitude. As shown, for example, a second ultrasonic energy pulse 3702' is delivered at an amplitude lower than the first amplitude and a third ultrasonic energy pulse 3702" is delivered at an amplitude that is lower the second predetermined amplitude. The RF energy pulses 3704 are delivered until the tissue is sealed or until the tissue impedance is equal to or greater than a predetermined threshold. After the last delivered RF energy pulse 3704' is turned OFF, the last ultrasonic energy pulse 3702'" is turned ON to cut tissue. The last ultrasonic energy pulse 3702'" may be delivered at an amplitude that either the same as the first amplitude, may be different than previous amplitudes, or may be equal to one of the intermittent amplitudes.

For the seal and cut pulse sequences 3740, 3750, on thick tissue applications, the ultrasonic modality take approximately 250 ms to seek, meaning that low pulse widths result in a short amount of therapeutic time. In some aspects, pulse widths longer than 500 ms, for example, may provide certain benefits.

FIG. 63 is a timing diagram of a seal only pulse sequence 3760 where the ultrasonic energy pulse 3702 current is be set based on the impedance measured with the preceding RF energy pulse 3704. The right vertical axis is tissue impedance in Ohms. The ultrasonic energy pulse 3702 current could be set based on the impedance measured with the preceding RF energy pulse 3704. It would be preferred to have the ultrasonic energy pulse 3702 current high when the preceding RF impedance was low. As the RF impedance increases the ultrasonic energy pulse 3702 current of the next pulse would decrease. This would allow the technique to compensate for the amount of tissue positioned within the jaws of the end effector 125, where thick tissue/bundle applications would stay at lower impedance for a longer period of time and would require more energy/heat to seal. As shown in FIG. 63, based on the first two low tissue impedance 3706 measurements the ultrasonic energy pulse 3702 current amplitude remains the same. After the third tissue impedance 3706' measurement, the amplitude of the ultrasonic energy pulse 3702' current is reduced until the tissue impedance exceeds a predetermined threshold and the RF energy pulse 3704' current remains ON while the ultrasonic energy pulse 3702 current amplitude remains at 0 mA.

In one aspect the first energy modality is RF energy and the second energy modality is ultrasonic energy. In one aspect, the process depicted by the logic flow diagram 3800 may be repeated until the tissue is sealed. As discussed in connection with FIGS. 57-60, in a seal only method, the ultrasonic energy modality may be turned off after a few predetermined number of cycles or based on tissue impedance measurements to avoid cutting the tissue while the RF energy modality is delivered to make a tissue seal. The ultrasonic and/or the RF energy modalities may be delivered at the same amplitude or at variable amplitudes. For example, the RF energy modality may be delivered at the same amplitude whereas the amplitude of the ultrasonic energy modality is stepped down. As discussed in connection with FIGS. 61 and 62, during a seal and cut cycle, the ultrasonic energy modality is delivered last to effect a tissue after the tissue is sealed. As previously discussed, during the sealing cycle, the amplitude of the ultrasonic energy modality may be the same or may be stepped down. A discussed in connection with FIG. 63, in a seal only method, the amplitude of the ultrasonic energy modality is adjusted base don the previous tissue impedance measurement utilizing the RF energy modality. In any of the seal or seal and cut methods discussed above, the ultrasonic energy may be delivered first to preheat the ultrasonic blade 149 because of the higher thermal mass of the ultrasonic blade 149 with respect to the thermal mass of the clamp arm 145.

FIG. 64 is a logic flow diagram 3800 of a technique for delivering pulses of different energy modalities to tissue. As described herein, the logic flow diagram 3800 may be implemented in the generator 500, the multifunction surgical instrument 108, or a combination thereof. With reference now to the logic flow diagram 3800 of FIG. 64, initially, tissue is clamped between the clamp arm 145 and the ultrasonic blade 149 of the end effector 125 of the surgical instrument 108 and then the processor 502 signals the waveform generator 504 to deliver the pulse sequences discussed below. In accordance with the method, the processor 502 activates 3802 a first energy modality of the surgical instrument 108. After a first period, the processor 502 deactivates 3804 the first energy modality and activates 3806 a second energy modality for a second period. The second energy modality is activated 3806 independent of the first energy modality. After the second period expires, the processor 502 deactivates 3808 the second energy modality.

FIG. 65 is a logic flow diagram 3900 of a technique for delivering pulses of different energy modalities to tissue. As described herein, the logic flow diagram 3900 may be implemented in the generator 500, the multifunction surgical instrument 108, or a combination thereof. With reference now to the logic flow diagram 3900 of FIG. 65, initially, tissue is clamped between the clamp arm 145 and the ultrasonic blade 149 of the end effector 125 of the surgical instrument 108 and then the processor 502 signals the waveform generator 504 to deliver the pulse sequences discussed herein. In accordance with the method, the processor 502 activates 3902 an RF energy modality of the surgical instrument 108 to drive RF energy through electrodes located in the clamp arm 145 of the end effector 125. The processor 502 deactivates 3904 the RF energy modality upon detecting a first predetermined tissue impedance $Z_{T1}$ measured at the end effector 125 of the surgical instrument 108. The generator 500 then activates 3906 an ultrasonic energy modality of the surgical instrument 108 to drive the ultrasonic blade 149. The processor 502 deactivates 3908 the ultrasonic energy modality upon detecting a second predetermined tissue impedance $Z_{T2}$ at the end effector 125 of the surgical instrument 108. As previously discussed, the tissue impedance is determined by the processor 502 by dividing the voltage applied to the end effector 125 by the current delivered to the end effector 125. For example, the processor 502 can determine the tissue impedance by dividing the voltage sensed by the second voltage sensing circuit 524 by the current sensed by the current sensing circuit 514.

FIG. 66 is a logic flow diagram 4000 of a technique for delivering pulses of different energy modalities to tissue. As described herein, the logic flow diagram 4000 may be implemented in the generator 500, the multifunction surgical instrument 108, or a combination thereof. With reference now to the logic flow diagram 4000 of FIG. 66, initially, tissue is clamped between the clamp arm 145 and the ultrasonic blade 149 of the end effector 125 of the surgical instrument 108 and then the processor 502 signals the waveform generator 504 to deliver the pulse sequences discussed herein. In accordance with the method, the processor 502 activates 4002 an RF energy modality of the surgical instrument 108 to drive RF energy through electrodes located in the clamp arm 145 of the end effector 125. The processor 502 deactivates 4004 the RF energy modality upon the expiration of a first predetermined period $T_1$. The processor 502 activates 4006 an ultrasonic energy modality of the surgical instrument 108 to drive the ultrasonic blade 149. The processor 502 deactivates 4008 the ultrasonic energy modality upon the expiration of a second predetermined period $T_2$.

Techniques for Simultaneously Delivering Blasts of Ultrasonic and RF Energy in a Combination Ultrasonic/RF Surgical Instrument In one aspect, the present disclosure provides a technique for delivering a combination simultaneous blast of RF and ultrasonic energy to an end effector of a surgical instrument by controlling the power delivered to an end effector from a generator, such as any one of the generators 102, 200, 300, 400, 500 (FIGS. 1-3 and 4-8), or a surgical instrument, such as the surgical instrument 108 (FIGS. 1-3). In accordance with the present technique, a combination simultaneous blast of RF and ultrasonic energy can be delivered to an end effector of a surgical instrument can be varied based on properties or parameters of tissue interacting with the end effector. For conciseness and clarity of disclosure, the techniques for delivering a combination simultaneous blast of RF and ultrasonic energy to the end effector will be described with reference to the multifunction surgical instrument 108 of FIG. 2 coupled to the generator 500 of FIG. 8, although it will be appreciated that other configurations of instruments, generators, and end effectors described herein may be readily substituted without departing from the scope of the present disclosure.

FIGS. 67-71 illustrate aspects of delivering multiple energy modalities to tissue. In one aspect the first energy modality is RF energy and the second energy modality is ultrasonic energy. There are many benefits to a surgical device that is capable of delivering both RF and ultrasonic energy. A surgical instrument capable of delivering both modalities provides stronger seals and can cut tissue without the need of a separate knife. The following disclosure provides multiple pulsing techniques than can be utilized for vessel sealing. These techniques employ tissue impedance measurements, current measurements, can seal only, and can seal and cut tissue.

The various aspects described below provide simultaneous activation of multiple energy modalities such as RF and ultrasonic energy modalities. Initially both RF and ultrasonic modalities are delivered to tissue. The RF energy modality is utilized for the first portion of the seal. After a set amount of time $T_1$, based off the RF impedance $Z_T$ detected, the ultrasonic modality is terminated. A short blast of ultrasonic energy at the beginning of the seal cycle provides benefits to sealing, as it aids in heating the ultrasonic blade and subsequently the tissue surface in contact with the blade while the electrode is simultaneously heating the tissue surface in contact with the RF electrodes.

These techniques may be implemented using multiple generators, one generator configured to deliver RF energy and another generator configured to deliver ultrasonic energy. Alternatively, these techniques may be implemented with a single generator configured to deliver both RF and ultrasonic energy. In other aspects, these techniques may be implemented with a single generator that is configured to deliver RF and ultrasonic energy simultaneously through a single output port. These techniques comprise simultaneous pulsing of RF and ultrasonic energy modalities to create strong seals. Multiple configurations of pulsing are disclosed. Multiple configurations of the simultaneous techniques are disclosed.

FIG. 67 is a logic flow diagram 4100 of one aspect of a process of applying simultaneous activation of different energy modalities to tissue. As described herein, the logic flow diagram 4100 may be implemented in the generator 500, the multifunction surgical instrument 108, or a combination thereof. With reference now to the logic flow diagram 4100 of FIG. 67, tissue is clamped between the clamp arm 145 and the ultrasonic blade 149 of the end effector 125 of the surgical instrument 108 and then the generator 500 delivers the simultaneous energy modalities. The total seal time 4102 is shown along a vertical axis.

Once tissue is clamped between the clamp arm 145 and the ultrasonic blade 149 of the end effector 125 of the surgical instrument 108, the processor 502 signals the waveform generator 504 to deliver the pulse sequences discussed herein. In accordance with the logic flow diagram 4100 of FIG. 67, the RF energy modality application process 4104 is shown on the left and ultrasonic energy modality application process 4116 is shown on the right. The processor 502 activates 4196 the RF energy modality at the same time that the ultrasonic energy modality is activated 4118. Once the RF energy modality is activated 4106, the processor 502 signals the waveform generator 504 to deliver 4108 RF energy in accordance with a variety of RF sealing techniques, including RF sealing techniques described herein in connection with the logic diagram 4600 shown FIG. 72. Turning back to FIG. 67, the processor 502 activates 4120 the ultrasonic energy modality at a constant power level. During the simultaneous application of the RF and ultrasonic energy modalities, the processor 502 measures the RF tissue impedance $Z_{tissue}$ and when the RF tissue impedance $Z_{tissue}$ meets ore exceeds an ultrasonic termination impedance $Z_{US-term}$ (see FIG. 68) it is provided 4110 as feedback to the processor 502 to signal 4122 the waveform generator 504 and amplifier 506 to terminate 4124 delivery of ultrasonic energy to the end effector 125. Meantime, the RF energy modality is continuously delivered until an RF termination impedance $Z_{RF-term}$ is reached 4112 at which point the processor 502 signals the waveform generator 504 to terminate 4114 delivery of RF energy. The short blast of the ultrasonic energy at the beginning of the seal cycle provides benefits to sealing, as it aids in heating the ultrasonic blade 149 and subsequently the tissue surface in contact with the blade 149 while the electrode in the clamp arm 145 is simultaneously heating the tissue surface in contact with the electrode. As previously discussed, the tissue impedance is determined by the processor 502 by dividing the voltage applied to the end effector 125 by the current delivered to the end effector 125. For example, the processor 502 can determine the tissue impedance by dividing the voltage sensed by the second voltage sensing circuit 524 by the current sensed by the current sensing circuit 514.

FIG. 68 is a graphical representation of RF Impedance versus Time in connection with the logic flow diagram 4100 of FIG. 67 to illustrate the ultrasonic termination impedance. The horizontal axis is time (ms) and the vertical axis is RF impedance (Ohms). The tissue impedance $Z_{tissue}$ curve 4202 is monitored during the sealing period utilizing the RF energy. When the tissue impedance $Z_{tissue}$ reaches the ultrasonic termination impedance $Z_{US-term}$ 4204 the ultrasonic power is terminated and when the tissue impedance $Z_{tissue}$ reaches the RF termination impedance $Z_{RF-term}$ 4206 the RF energy is terminated.

FIG. 69 illustrates an example of the quality of a seal 4302 made in a vessel 4300 using the simultaneous activation of RF and ultrasonic energy modalities as described in connection with FIGS. 67 and 68. The main advantage of simultaneous activation of RF and ultrasonic energy modalities is that the ultrasonic energy heats up the ultrasonic blade 149 and helps to create a reduction in the difference in thermal mass between the ultrasonic blade 149 and the electrode in the clamp arm 145. During a non-simultaneous activation seal cycle utilizing both RF and ultrasonic modalities, a challenge is posed to create a strong seal with varying thermal masses on either side of the end effector 125 jaw.

FIG. 70 is a graphical representation 4400 of seal burst pressure of carotid bundles versus an RF only seal and a simultaneous RF/ultrasonic seal as described in connection with FIGS. 67-69. The horizontal axis is an RF seal only boxplot 4402 and a simultaneous RF/ultrasonic boxplot 4404. The boxplots 4402, 4404 demonstrate the tissue effect advantages described ion connection with the simultaneous RF/ultrasonic energy modality activation process 4100 shown in connection with FIG. 67 where simultaneously heating the ultrasonic blade and electrode provides a high quality 4302 in a vessel as shown in FIG. 69.

FIG. 71 is a logic flow diagram 4500 of a process of simultaneous activation of RF and ultrasonic energy modalities. As described herein, the logic flow diagram 4500 may be implemented in the generator 500, the multifunction surgical instrument 108, or a combination thereof. With reference now to the logic flow diagram 4500 of FIG. 71, initially, tissue is clamped between the clamp arm 145 and the ultrasonic blade 149 of the end effector 125 of the surgical instrument 108 and then the processor 502 signals the waveform generator 504 to deliver the pulse sequences discussed herein. In accordance with the logic flow diagram 4500, the processor 502 simultaneously activates 4502 an RF energy modality and an ultrasonic energy modality of the surgical instrument 108. The processor 502 monitors 4504 the tissue impedance using RF energy modality. When the tissue impedance is equal to or greater than a first termination impedance, the generator 500 deactivates 4506 the ultrasonic energy modality of the surgical instrument 108. The RF energy modality is delivered until the tissue impedance is equal to or greater than a second termination impedance, at which time the processor 502 deactivates 4508 the RF energy modality of the surgical instrument 108 and the tissue seal is complete.

In some aspects utilizing a pulsed drive signal, a generator, such as, for example, one of generators 102, 200, 300, 400, 500 described in connection with FIGS. 1-3 and 5-8, may apply one or more composite load curves to the drive signal, and ultimately to the tissue. Composite load curves may define a level of power to be delivered to the tissue as a function of a measured tissue property or properties (e.g., impedance). Composite load curves may, additionally, define pulse characteristics, such as pulse width, in terms of the measured tissue properties.

FIG. 72 illustrates one aspect of a logic diagram 4600 for the selection and application of composite load curves by any one of generators 102, 200, 300, 400, 500. It will be appreciated that the logic diagram 4600 may be implemented with any suitable type of generator or surgical device. According to various aspects, the logic diagram 4600 may be implemented utilizing an electrosurgical instrument, such as the electrosurgical instrument 106 described above with respect to FIG. 1, an ultrasonic surgical instrument 104 described above with respect to FIG. 1, or a combination surgical instrument 108 described above with respect to FIGS. 1-3.

Referring back to FIG. 72, a control process 4602 may be executed, for example by a digital device of the generator 102 to select and apply composite load curves 4606, 4608, 4610, 4612. The control process 4602 may receive a time input from a clock 4604 and may also receive loop input 4624 from sensors 4618. The loop input 4624 may represent properties or characteristics of the tissue that may be utilized in the control process 4602 to select and/or apply a composite load curve. Examples of such characteristics may comprise, for example, current, voltage, temperature, reflectivity, force delivered to the tissue, resonant frequency, rate of change of resonant frequency, etc. The sensors 4618 may be dedicated sensors (e.g., thermometers, pressure sensors, etc.) or may be software implemented sensors for deriving tissue characteristics based on other system values (e.g., for observing and/or calculating voltage, current, tissue temperature, etc., based on the drive signal). The control process 4602 may select one of the composite load curves 4606, 4608, 4610, 4612 to apply, for example based on the loop input 4624 and/or the time input from the clock 4604. Although four composite load curves are shown, it will be appreciated that any suitable number of composite load curves may be used.

The control process 4602 may apply a selected composite load curve in any suitable manner. For example, the control process 4602 may use the selected composite load curve to calculate a power level and one or more pulse characteristics based on tissue impedance (e.g., currently measured tissue impedance may be a part of, or may be derived from, the loop input) or resonant frequency characteristics of a ultrasonic surgical instrument 104. Examples of pulse characteristics that may be determined based on tissue impedance according to a composite load curve may include pulse width, ramp time, and off time.

At set point 4614, the derived power and pulse characteristics may be delivered to the drive signal. In various aspects, a feedback loop 4622 may be implemented to allow for more accurate modulation of the drive signal. At the output of the set point 4614, the drive signal may be provided to an amplifier 4616, which may provide suitable amplification. The amplified drive signal may be provided to a load 4620 (e.g., via sensors 4618). The load 4620 may comprise the tissue, the surgical instrument 104, 106, 108, and/or any cable electrically coupling a generator with the surgical instrument 104, 106, 108 (e.g., cables 142, 144, 146).

In various aspects the state of coagulation may be determined using neural networks that are configured to take a plurality of factors into account. In some aspects, a generator may be configured to drive both ultrasonic and electrosurgical systems and include a nested neural network to identify whether the generator is presented with a true short circuit vs. a low impedance tissue. In addition, in some aspects, to assist in the detection of short circuits, the neural network may be configured to track and store at least the following factors: a. Measured resistance/impedance; b. Drive current (RMS); c. Drive Voltage (RMS); and d. Moving average of measured impedance. In some aspects, the neural network will be thought to in order to be capable of discerning between a true short and low impedance tissue. In other aspects, a neural network may be programmed to identify properties in metal, tissues, and other non-tissue elements. The neural network also may be configured to transmit the exploratory pulse to the transducer. In addition, new developments or additional programs, including receiving feedback from the attempts to detect short circuits, may be incorporated back into the neural network to increase its situational awareness and effectively better learn how to detect a true short circuit. With confirmation of a short circuit both by RF and ultrasonic functionality, this can allow for less time spent getting repeat errors on RF and faster transection on low impedance tissue. An example of a neural network is described in connection with FIG. 73.

FIG. 73 illustrates one aspect of a neural network 4700 for controlling a generator. FIG. 73 illustrates one aspect of an artificial neural network 4700 for generating an estimated temperature $T_{est}$ resulting from an application of ultrasonic energy using an ultrasonic surgical instrument, such as the ultrasonic surgical instruments 104, 106, 108 (FIGS. 1-3). In certain aspects, the neural network 4700 may be implemented in the processor and/or the programmable logic device of the generator 102 (FIG. 1). The neural network 4700 may comprise an input layer 4702, one or more nodes 4704 defining a hidden layer 4706, and one or more nodes 4708 defining an output layer 4710. For the sake of clarity, only one hidden layer 4706 is shown. In certain aspects, the neural network 4700 may comprise one or more additional hidden layers in a cascaded arrangement, with each additional hidden layer having a number of nodes 4704 that may be equal to or different from the number of nodes 4704 in the hidden layer 4706.

Each node 4704, 4708 in the layers 4702, 4710 may include one or more weight values w 4712, a bias value b 4714, and a transform function f 4716. In FIG. 73, the use of different subscripts for these values and functions is intended to illustrate that each of these values and functions may be different from the other values and functions. The input layer 4702 comprises one or more input variables p 4718, with each node 4704 of the hidden layer 4706 receiving as input at least one of the input variables p 4718. As shown in FIG. 73, for example, each node 4704 may receive all of the input variables p 4718. In other aspects, less than all of the input variables p 4718 may be received by a node 4704. Each input variable p 4718 received by a particular node 4704 is weighted by a corresponding weight value w 4712, then added to any other similarly weighted input variables p 4718, and to the bias value b 4712. The transform function f 4716 of the node 4704 is then applied to the resulting sum to generate the node's output. In FIG. 73, for example, the output of node 4704-1 may be given as $f_1(n_1)$, where $n_1=(w_{1,1} \cdot p_1+w_{1,2} \cdot p_2+ \ldots +w_{1,j} \cdot p_{1,j}+b_1$.

A particular node 4708 of the output layer 4710 may receive an output from one or more of the nodes 4704 of the hidden layer 4706 (e.g., each node 4708 receives outputs $f_1(\bullet), f_2(\bullet), \ldots, f_i(\bullet)$ from respective nodes 4704-1, 4704-2, ..., 4704-$i$ in FIG. 73), with each received output being weighted by a corresponding weight value w 4712 and subsequently added to any other similarly weighted received outputs, and to a bias value b 4714. The transform function f 4716 of the node 4708 is then applied to the resulting sum to generate the node's output, which corresponds to an output of the neural network 4700 (e.g., the estimated temperature $T_{est}$ in the aspect of FIG. 73). Although the aspect of the neural network 4700 in FIG. 73 comprises only one node 4708 in the output layer 4710, in other aspects the neural network 4700 may comprise more than one output, in which case the output layer 4710 may comprise multiple nodes 4708.

In certain aspects, the transform function f 4716 of a node 4704, 4708 may be a nonlinear transfer function. In one aspect, for example, one or more of the transform functions f 4716 may be a sigmoid function. In other aspects, the transform functions f 4716 may include a tangent sigmoid, a hyperbolic tangent sigmoid, a logarithmic sigmoid, a linear transfer function, a saturated linear transfer function, a radial basis transfer function, or some other type of transfer function. The transform function f 4716 of a particular node 4704, 4708 may be the same as, or different from, a transform function f 4716 in another node 4704, 4708.

In certain aspects, the input variables p 4718 received by the nodes 4704 of the hidden layer 4706 may represent, for example, signals and/or other quantities or conditions known or believed to have an effect on the temperature or heating resulting from an application of ultrasonic energy. Such variables may comprise, for example, one or more of: drive voltage output by the generator 102, drive current output by the generator 102, drive frequency of the generator output 102, drive power output by the generator 102, drive energy output by the generator 102, impedance of the ultrasonic transducer 120, and time duration over which ultrasonic energy is delivered. Additionally, one or more of the input variables p 4718 may be unrelated to outputs of the generator 102 and may comprise, for example, characteristics of the end effector 122, 125 (e.g., blade tip size, geometry, and/or material) and a particular type of tissue targeted by the ultrasonic energy.

The neural network 4700 may be trained (e.g., by changing or varying the weight values w 4712, the bias values b 4714, and the transform functions f 4716) such that its output (e.g., estimated temperature $T_{est}$ in the aspect of FIG. 73) suitably approximates a measured dependency of the output for known values of the input variables p 4718. Training may be performed, for example, by supplying known sets of input variables p 4718, comparing output of the neural network 4700 to measured outputs corresponding to the known sets of input variables p 4718, and modifying the weight values w 4712, the bias values b 4714, and/or the transform functions f 4716 until the error between the outputs of the neural network 4700 and the corresponding measured outputs is below a predetermined error level. For example, the neural network 4700 may be trained until the mean square error is below a predetermined error threshold. In certain aspects, aspects of the training process may be implemented by the neural network 4700 (e.g., by propagating errors back through the network 4700 to adaptively adjust the weight values w 4712 and/or the bias values b 4714).

While various details have been set forth in the foregoing description, it will be appreciated that the various aspects of the serial communication protocol for medical device may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, a technique refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one form," or "an form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

It is worthy to note that any reference to "one aspect," "an aspect," "one form," or "an form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

Although various forms have been described herein, many modifications, variations, substitutions, changes, and equivalents to those forms may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed forms. The following claims are intended to cover all such modification and variations.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one form, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely example, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Although various forms have been described herein, many modifications, variations, substitutions, changes, and equivalents to those forms may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed forms. The following claims are intended to cover all such modification and variations.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A method for distinguishing a short circuit from a low impedance measurement in tissue in a surgical system configured to apply radio frequency energy and ultrasonic energy to a target surgical site, the method comprising:

delivering, by a radio frequency (RF) drive circuit, RF energy to an electrode of a surgical instrument, wherein the electrode is in contact with tissue at the target surgical site;

receiving a low impedance measurement from the target surgical site consistent with the short circuit;

in response to the low impedance measurement, transitioning from delivering, by the RF drive circuit, the RF energy to delivering, by an ultrasonic drive circuit, ultrasonic energy to an ultrasonic blade of the surgical instrument;

delivering, by the ultrasonic drive circuit, an exploratory ultrasonic pulse to the ultrasonic blade;

measuring, by a processor, in the tissue at the target surgical site, an acoustic response to the exploratory ultrasonic pulse;

determining, by the processor, that the target surgical site is consistent with a low impedance area and not the short circuit by determining that the acoustic response is not consistent with the exploratory ultrasonic pulse contacting metal or other material that would cause the short circuit; and based on the determination, delivering, by the ultrasonic drive circuit, ultrasonic energy to the ultrasonic blade to cut the tissue.

2. The method of claim 1, wherein the exploratory ultrasonic pulse is a first exploratory ultrasonic pulse and the acoustic response is a first acoustic response, the method further comprising:

delivering, by the ultrasonic drive circuit, a second exploratory ultrasonic pulse to the ultrasonic blade;

measuring, by the processor, in the tissue at the target surgical site, a second acoustic response to the second exploratory ultrasonic pulse;

determining, by the processor, that the short circuit has occurred based on determining that the second acoustic response measured by the processor is consistent with the second exploratory ultrasonic pulse contacting metal or other material that would cause the short circuit; and upon determining, by the processor, that the short circuit has occurred, ceasing delivery of the ultrasonic energy to the surgical instrument.

3. The method of claim 1, wherein determining that the target surgical site is consistent with the low impedance area and not the short circuit comprises utilizing a nested neural network of the surgical system.

4. The method of claim 3, further comprising: measuring, by the nested neural network, at least one of: a tissue impedance of the tissue, a drive current, or a moving average of tissue impedance of the tissue when the exploratory ultrasonic pulse is delivered to the ultrasonic blade; and continuing to deliver ultrasonic energy to cut the tissue based on the at least one of the tissue impedance, the drive current, or the moving average of tissue impedance.

5. A surgical instrument for coagulating and dissecting tissue, the surgical instrument comprising:

a processor;

an end effector at a distal end of the surgical instrument, the end effector configured to interact with tissue, the end effector comprising:

a clamp arm comprising an electrode; and an ultrasonic blade; and an ultrasonic transducer acoustically coupled to the ultrasonic blade and configured to receive a drive signal from a generator to cause ultrasonic motion of the ultrasonic blade and deliver ultrasonic energy to the ultrasonic blade;
wherein the processor is configured to:
control delivery of radio frequency (RF) energy to the electrode;
when the electrode is in contact with the tissue at a surgical site, receive a low impedance measurement from the surgical site consistent with a short circuit;
in response to the low impedance measurement, transition from delivery of the RF energy to the electrode to delivery of the ultrasonic energy to the ultrasonic blade;
control delivery of an exploratory ultrasonic pulse to the ultrasonic transducer;
measure in the tissue, an acoustic response to the exploratory ultrasonic pulse;
determine that the surgical site is consistent with a low impedance area and not the short circuit by determining that the acoustic response is not consistent with the exploratory ultrasonic pulse contacting metal or other material that would cause the short circuit; and
based on the determination, control delivery of the ultrasonic energy to the ultrasonic blade to cut the tissue.

6. The surgical instrument of claim 5, wherein the exploratory ultrasonic pulse is a first exploratory ultrasonic pulse and the acoustic response is a first acoustic response, and wherein the processor is further configured to:
cause delivery of a second exploratory ultrasonic pulse to the ultrasonic blade;
measure in the tissue a second acoustic response to the second exploratory ultrasonic pulse; determine that the short circuit has occurred based on determining that the second acoustic response measured by the processor is consistent with the second exploratory ultrasonic pulse contacting metal or other material that would cause the short circuit; and upon determining that the short circuit has occurred, cease delivery of the ultrasonic energy to the ultrasonic blade.

7. The surgical instrument of claim 5, further comprising a nested neural network, and wherein the processor is configured to determine that the surgical site is consistent with the low impedance area and not the short circuit using the nested neural network.

8. The surgical instrument of claim 7, wherein the processor is configured to use the nested neural network to measure at least one of: a tissue impedance of the tissue, a drive current, or a moving average of tissue impedance of the tissue when the exploratory ultrasonic pulse is delivered to the ultrasonic blade, and wherein the processor is configured to continue to control delivery of the ultrasonic energy to the ultrasonic blade to cut the tissue based on the at least one of: the tissue impedance of the tissue, the drive current, or the moving average of tissue impedance of the tissue when the exploratory ultrasonic pulse is delivered to the ultrasonic blade.

9. A generator for delivering energy to a surgical instrument for coagulating and dissecting tissue, the surgical instrument comprising an end effector at a distal end thereof, the end effector configured to interact with the tissue, the end effector comprising a clamp arm, an ultrasonic blade, an ultrasonic transducer acoustically coupled to the ultrasonic blade and configured to receive a drive signal from the generator to cause ultrasonic motion of the ultrasonic blade and deliver ultrasonic energy to the ultrasonic blade, the generator comprising:
a first drive circuit configured to deliver a drive signal to the ultrasonic transducer;
a second drive circuit configured to deliver radio frequency (RF) energy to an electrode; and
a processor configured to control the first drive circuit and the second drive circuit, and wherein the processor is configured to:
control the second drive circuit to deliver the RF energy to the electrode;
when the electrode is in contact with the tissue at a surgical site, receive a low impedance measurement from the surgical site consistent with a short circuit;
in response to the low impedance measurement, transition from the second drive circuit delivering the RF energy to the electrode to the first drive circuit delivering the drive signal to the ultrasonic transducer;
control the first drive circuit to deliver the drive signal comprising an exploratory ultrasonic pulse to the ultrasonic transducer;
measure in the tissue, an acoustic response to the exploratory ultrasonic pulse;
determine that the surgical site is consistent with a low impedance area and not the short circuit by determining that the acoustic response is not consistent with the exploratory ultrasonic pulse contacting metal or other material that would cause the short circuit; and
based on the determination, control the first drive circuit to deliver the drive signal to the ultrasonic transducer to cut the tissue.

10. The generator of claim 9, wherein the exploratory ultrasonic pulse is a first exploratory ultrasonic pulse and the acoustic response is a first acoustic response, and wherein the processor is further configured to:
cause delivery of a second exploratory ultrasonic pulse to the ultrasonic blade;
measure in the tissue a second acoustic response to the second exploratory ultrasonic pulse;
determine that the short circuit has occurred based on determining that the second acoustic response measured by the processor is consistent with the second exploratory ultrasonic pulse contacting metal or other material that would cause the short circuit; and
upon determining that the short circuit has occurred, control the first drive circuit to cease delivery of the drive signal to the ultrasonic transducer.

11. The generator of claim 9, further comprising a nested neural network, and wherein the processor is configured to determine that the surgical site is consistent with the low impedance area and not the short circuit using the nested neural network.

12. The generator of claim 11, wherein the processor is configured to use the nested neural network to measure at least one of: a tissue impedance of the tissue, a drive current, or a moving average of tissue impedance of the tissue when the exploratory ultrasonic pulse is delivered to the ultrasonic transducer, and wherein the processor is configured to continue to control the first drive circuit to deliver the drive signal to the ultrasonic transducer to cut the tissue based on the at least one of: the tissue impedance of the tissue, the drive current, or the moving average of tissue impedance of the tissue when the exploratory ultrasonic pulse is delivered to the ultrasonic transducer.

* * * * *